(12) United States Patent
Modak et al.

(10) Patent No.: US 9,981,069 B2
(45) Date of Patent: May 29, 2018

(54) BIO-FILM RESISTANT SURFACES

(71) Applicant: THE TRUSTEES OF COLUMBIA UNIVERSITY IN THE CITY OF NEW YORK, New York, NY (US)

(72) Inventors: Shanta Modak, River Edge, NJ (US); Arnab Kumar Ghosh, Fort Lee, NJ (US); Ronald Citron, Blandon, PA (US); Santoshkumar Hanmantrao Dongre, Maharashtra (IN); Nayana Baiju, Kerala (IN)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 116 days.

(21) Appl. No.: 14/564,920

(22) Filed: Dec. 9, 2014

(65) Prior Publication Data
US 2015/0118275 A1 Apr. 30, 2015

Related U.S. Application Data

(63) Continuation-in-part of application No. 12/134,911, filed on Jun. 6, 2008, now Pat. No. 8,932,624, and a continuation-in-part of application No. 14/194,381, filed on Feb. 28, 2014, which is a continuation of application No. PCT/US2012/052793, filed on Aug. 29, 2012.

(60) Provisional application No. 60/945,288, filed on Jun. 20, 2007, provisional application No. 61/529,661, filed on Aug. 31, 2011, provisional application No. 61/529,703, filed on Aug. 31, 2011.

(51) Int. Cl.
| | |
|---|---|
| *A61L 29/16* | (2006.01) |
| *A61L 29/08* | (2006.01) |
| *A61L 27/54* | (2006.01) |
| *A61L 26/00* | (2006.01) |
| *A61L 27/26* | (2006.01) |
| *A01N 47/44* | (2006.01) |
| *A61L 15/46* | (2006.01) |
| *A01N 25/10* | (2006.01) |
| *A01N 31/02* | (2006.01) |
| *A01N 37/36* | (2006.01) |

(52) U.S. Cl.
CPC .............. *A61L 29/16* (2013.01); *A01N 25/10* (2013.01); *A01N 31/02* (2013.01); *A01N 37/36* (2013.01); *A01N 47/44* (2013.01); *A61L 15/46* (2013.01); *A61L 26/0052* (2013.01); *A61L 26/0066* (2013.01); *A61L 27/26* (2013.01); *A61L 27/54* (2013.01); *A61L 29/085* (2013.01); *A61L 2300/104* (2013.01); *A61L 2300/206* (2013.01); *A61L 2300/216* (2013.01); *A61L 2300/404* (2013.01); *A61L 2420/06* (2013.01)

(58) Field of Classification Search
CPC ...................................................... A61L 29/16
See application file for complete search history.

(56) References Cited

U.S. PATENT DOCUMENTS

| | | | |
|---|---|---|---|
| 3,566,874 | A | 3/1971 | Shepherd et al. |
| 3,674,901 | A | 7/1972 | Shepherd et al. |
| 3,695,921 | A | 10/1972 | Shepherd et al. |
| 3,699,956 | A | 10/1972 | Kitrilakis et al. |
| 3,705,938 | A | 12/1972 | Hyman et al. |
| 3,987,797 | A | 10/1976 | Stephenson |
| 4,022,605 | A | 5/1977 | Konya et al. |
| 4,024,871 | A | 5/1977 | Stephenson |
| 4,049,802 | A | 9/1977 | Fox, Jr. |
| 4,054,139 | A | 10/1977 | Crossley |
| 4,064,238 | A | 12/1977 | Bocher et al. |
| 4,070,713 | A | 1/1978 | Stockum |
| 4,143,109 | A | 3/1979 | Stockum |
| 4,243,657 | A | 1/1981 | Okumura et al. |
| 4,273,873 | A | 6/1981 | Sugitachi et al. |
| 4,318,947 | A | 3/1982 | Joung |
| 4,330,531 | A | 5/1982 | Alliger |
| 4,381,380 | A | 4/1983 | LeVeen et al. |
| 4,404,197 | A | 9/1983 | Fox, Jr. et al. |
| 4,432,766 | A | 2/1984 | Bellotti et al. |
| 4,499,154 | A | 2/1985 | James et al. |
| 4,563,485 | A | 1/1986 | Fox, Jr. et al. |
| 4,579,731 | A | 4/1986 | Fox, Jr. et al. |

(Continued)

FOREIGN PATENT DOCUMENTS

| | | |
|---|---|---|
| CH | 654327 | 2/1986 |
| DE | 4140474 | 6/1993 |

(Continued)

OTHER PUBLICATIONS

U.S. Appl. No. 12/134,918 (US 2009/0004122), filed Jun. 6, 2008 (Jan. 1, 2009).

(Continued)

*Primary Examiner* — Benjamin Packard
(74) *Attorney, Agent, or Firm* — Tarter Krinsky & Drogin LLP

(57) ABSTRACT

The present invention relates to methods and compositions for rendering a surface resistant to bio-film formation by a combination of an alkanediol and an antimicrobial agent (and, optionally, an organic hydroxy acid). The invention provides for compositions which may be used to render surfaces bio-film resistant, articles having bio-film resistant surfaces, and methods for their preparation. The present invention may be advantageously applied to medical articles as well as articles used in non-medical contexts, such as child care or food preparation.

23 Claims, No Drawings

(56) References Cited

U.S. PATENT DOCUMENTS

| | | |
|---|---|---|
| 4,581,028 A | 4/1986 | Fox, Jr. et al. |
| 4,592,920 A | 6/1986 | Murtfeldt |
| 4,597,108 A | 7/1986 | Momose |
| 4,603,152 A | 7/1986 | Laurin et al. |
| 4,605,564 A | 8/1986 | Kulla et al. |
| 4,612,337 A | 9/1986 | Fox, Jr. et al. |
| 4,623,329 A | 11/1986 | Drobish et al. |
| 4,675,347 A | 6/1987 | Mochizuki et al. |
| 4,677,143 A | 6/1987 | Laurin et al. |
| 4,723,950 A | 2/1988 | Lee |
| 4,738,668 A | 4/1988 | Bellotti et al. |
| 4,769,013 A | 9/1988 | Lorenz et al. |
| 4,771,482 A | 9/1988 | Shlenker |
| 4,853,978 A | 8/1989 | Stockman |
| 4,859,359 A | 8/1989 | DeMatteo et al. |
| 4,867,898 A | 9/1989 | Spaulding et al. |
| 4,919,837 A | 4/1990 | Gluck |
| 4,925,668 A | 5/1990 | Khan et al. |
| 4,956,170 A | 9/1990 | Lee |
| 4,956,354 A | 9/1990 | Gutierrez |
| 4,975,217 A | 12/1990 | Brown-Skrobot et al. |
| 4,994,047 A | 2/1991 | Walker et al. |
| 4,999,210 A | 3/1991 | Solomon et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,024,232 A | 6/1991 | Smid et al. |
| 5,031,245 A | 7/1991 | Milner |
| 5,033,488 A | 7/1991 | Curtis et al. |
| 5,059,416 A | 10/1991 | Cherukuri et al. |
| 5,061,254 A | 10/1991 | Karakelle et al. |
| 5,061,738 A | 10/1991 | Solomon et al. |
| 5,073,366 A | 12/1991 | Beck |
| 5,089,205 A | 2/1992 | Huang et al. |
| 5,091,442 A | 2/1992 | Milner |
| 5,100,652 A | 3/1992 | Kross et al. |
| 5,102,401 A | 4/1992 | Lambert et al. |
| 5,133,090 A | 7/1992 | Modak et al. |
| 5,135,747 A | 8/1992 | Faryniarz et al. |
| 5,165,952 A | 11/1992 | Solomon et al. |
| 5,176,665 A | 1/1993 | Watanabe et al. |
| 5,180,605 A | 1/1993 | Milner |
| 5,196,205 A | 3/1993 | Borody |
| 5,200,194 A | 4/1993 | Edgren et al. |
| 5,208,031 A | 5/1993 | Kelly |
| 5,209,251 A | 5/1993 | Curtis et al. |
| 5,217,493 A | 6/1993 | Raad et al. |
| 5,236,422 A | 8/1993 | Eplett, Jr. |
| 5,261,421 A | 11/1993 | Milner |
| 5,263,930 A | 11/1993 | Ensminger |
| 5,310,546 A | 5/1994 | Douglas |
| 5,334,588 A | 8/1994 | Fox, Jr. et al. |
| 5,335,373 A | 8/1994 | Dresdner, Jr. et al. |
| 5,357,636 A | 10/1994 | Dresdner, Jr. et al. |
| 5,403,864 A | 4/1995 | Bruch et al. |
| 5,420,197 A | 5/1995 | Lorenz et al. |
| 5,451,424 A | 9/1995 | Solomon et al. |
| 5,516,510 A | 5/1996 | Beilfuss et al. |
| 5,567,495 A | 10/1996 | Modak et al. |
| 5,591,442 A | 1/1997 | Diehl et al. |
| 5,614,538 A | 3/1997 | Nelson, Jr. |
| 5,616,338 A | 4/1997 | Fox, Jr. et al. |
| 5,624,704 A | 4/1997 | Darouiche et al. |
| 5,688,516 A | 11/1997 | Raad et al. |
| 5,705,532 A | 1/1998 | Modak et al. |
| 5,707,366 A | 1/1998 | Solomon et al. |
| 5,708,023 A | 1/1998 | Modak et al. |
| 5,736,574 A | 4/1998 | Burnier et al. |
| 5,756,145 A | 5/1998 | Darouiche |
| 5,763,412 A | 6/1998 | Khan et al. |
| 5,772,640 A | 6/1998 | Modak et al. |
| 5,776,430 A | 7/1998 | Osbourne et al. |
| 5,830,488 A | 11/1998 | Suzuki et al. |
| 5,854,266 A | 12/1998 | Nelson, Jr. |
| 5,866,527 A | 2/1999 | Mertens |
| 5,885,562 A | 3/1999 | Lowry et al. |
| 5,891,422 A | 4/1999 | Pan et al. |
| 5,902,283 A | 5/1999 | Darouiche et al. |
| 5,928,671 A | 7/1999 | Domenico |
| 5,968,539 A | 10/1999 | Beerse et al. |
| 5,980,477 A | 11/1999 | Kelly |
| 5,985,819 A | 11/1999 | Lu et al. |
| 5,985,918 A | 11/1999 | Modak et al. |
| 5,985,931 A | 11/1999 | Modak et al. |
| 5,989,531 A | 11/1999 | Schamper et al. |
| 6,022,551 A | 2/2000 | Jampani et al. |
| 6,037,386 A | 3/2000 | Modak et al. |
| 6,040,347 A | 3/2000 | Cupferman et al. |
| 6,045,817 A | 4/2000 | Anathapadmanabhan |
| 6,075,056 A | 6/2000 | Quigley, Jr. et al. |
| 6,083,208 A | 7/2000 | Modak et al. |
| 6,106,505 A | 8/2000 | Modak et al. |
| 6,107,261 A | 8/2000 | Taylor et al. |
| 6,120,758 A | 9/2000 | Siddiqui et al. |
| 6,136,771 A | 10/2000 | Taylor et al. |
| 6,187,327 B1 | 2/2001 | Stack |
| 6,204,230 B1 | 3/2001 | Taylor et al. |
| 6,211,243 B1 | 4/2001 | Johnson |
| 6,224,579 B1 | 5/2001 | Modak et al. |
| 6,258,368 B1 | 7/2001 | Beerse et al. |
| 6,261,271 B1 | 7/2001 | Solomon et al. |
| 6,270,811 B1 | 8/2001 | Fregonese |
| 6,280,758 B1 | 8/2001 | Warren et al. |
| 6,287,583 B1 | 9/2001 | Warren et al. |
| 6,312,675 B1 | 11/2001 | Deane |
| 6,319,958 B1 | 11/2001 | Johnson et al. |
| 6,323,166 B1 | 11/2001 | Kamiya |
| 6,323,171 B1 | 11/2001 | Fonsny et al. |
| 6,348,501 B1 | 2/2002 | Holt et al. |
| 6,387,357 B1 | 5/2002 | Chopra et al. |
| 6,397,224 B1 | 5/2002 | Zubeldia et al. |
| 6,414,032 B1 | 7/2002 | Johnson |
| 6,416,546 B1 | 7/2002 | Kimura et al. |
| 6,416,548 B2 | 7/2002 | Chinn et al. |
| 6,420,326 B1 | 7/2002 | Maile et al. |
| 6,420,431 B1 | 7/2002 | Johnson |
| 6,426,062 B1 | 7/2002 | Chopra et al. |
| 6,451,748 B1 | 9/2002 | Taylor et al. |
| 6,537,955 B1 | 3/2003 | Raso et al. |
| 6,582,719 B2 | 6/2003 | Modak et al. |
| 6,616,922 B2 | 9/2003 | Taylor et al. |
| 6,626,873 B1 | 9/2003 | Modak et al. |
| 6,630,163 B1 | 10/2003 | Murad |
| 6,632,784 B2 | 10/2003 | Massaux et al. |
| 6,635,676 B2 | 10/2003 | Baker, Jr. et al. |
| 6,696,399 B1 | 2/2004 | Chernin et al. |
| 6,699,825 B2 | 3/2004 | Rees et al. |
| 6,706,024 B2 | 3/2004 | Modak et al. |
| 6,716,883 B1 | 4/2004 | Casper et al. |
| 6,719,991 B2 | 4/2004 | Darouiche et al. |
| 6,723,689 B1 | 4/2004 | Hoang et al. |
| 6,733,745 B2 | 5/2004 | Rozzi et al. |
| 6,753,305 B2 | 6/2004 | Raso et al. |
| 6,846,846 B2 | 1/2005 | Modak et al. |
| 6,858,317 B2 | 2/2005 | Aamodt et al. |
| 6,872,195 B2 | 3/2005 | Modak et al. |
| 6,887,270 B2 | 5/2005 | Miller et al. |
| 6,921,745 B2 | 7/2005 | Yamada et al. |
| 6,951,833 B2 | 10/2005 | O'Neil |
| 6,969,522 B2 | 11/2005 | Bessette et al. |
| 6,974,584 B2 | 12/2005 | Bessette |
| 7,247,295 B2 | 7/2007 | Schmaus et al. |
| 7,329,412 B2 | 2/2008 | Modak et al. |
| 7,435,429 B2 | 10/2008 | Modak et al. |
| 7,537,779 B2 | 5/2009 | Modak et al. |
| 7,563,461 B2 | 7/2009 | Modak et al. |
| 7,563,462 B2 | 7/2009 | Modak et al. |
| 7,572,469 B2 | 8/2009 | Santo et al. |
| 7,745,425 B2 | 6/2010 | Modak et al. |
| 7,820,145 B2 | 10/2010 | Tamarkin et al. |
| 7,829,029 B2 | 11/2010 | Zumeris et al. |
| 7,871,649 B2 | 1/2011 | Modak et al. |
| 7,985,773 B2 | 7/2011 | Greten et al. |
| 8,003,673 B2 | 8/2011 | Alder et al. |

(56) References Cited

U.S. PATENT DOCUMENTS

| | | |
|---|---|---|
| 8,383,143 B2 | 2/2013 | Modak et al. |
| 8,641,686 B2 | 2/2014 | Stephan |
| 8,932,624 B2 | 1/2015 | Modak et al. |
| 2001/0010016 A1 | 7/2001 | Modak et al. |
| 2001/0024661 A1 | 9/2001 | Modak et al. |
| 2002/0022660 A1 | 2/2002 | Jampani et al. |
| 2002/0122876 A1 | 9/2002 | Modak et al. |
| 2002/0165130 A1 | 11/2002 | Johnson et al. |
| 2002/0173775 A1 | 11/2002 | Modak et al. |
| 2002/0192256 A1 | 12/2002 | Wu et al. |
| 2003/0113388 A1 | 6/2003 | Phan |
| 2003/0152644 A1 | 8/2003 | Modak et al. |
| 2003/0168077 A1 | 9/2003 | Brown et al. |
| 2003/0180233 A1 | 9/2003 | Anderson et al. |
| 2003/0195263 A1 | 10/2003 | Schmaus et al. |
| 2003/0213168 A1 | 11/2003 | Hesse et al. |
| 2004/0052831 A1 | 3/2004 | Modak et al. |
| 2004/0092482 A1 | 5/2004 | Gupta |
| 2004/0102429 A1 | 5/2004 | Modak et al. |
| 2004/0132667 A1 | 7/2004 | Lintner |
| 2004/0192551 A1 | 9/2004 | Bessette et al. |
| 2004/0208908 A1 | 10/2004 | Modak et al. |
| 2004/0247685 A1 | 12/2004 | Modak et al. |
| 2004/0253275 A1 | 12/2004 | Eini et al. |
| 2005/0019431 A1 | 1/2005 | Modak et al. |
| 2005/0026802 A1 | 2/2005 | Kilkenny et al. |
| 2005/0048139 A1 | 3/2005 | Modak et al. |
| 2005/0063939 A1* | 3/2005 | Ameer .................. C08G 63/06 424/78.37 |
| 2005/0187124 A1 | 8/2005 | Li et al. |
| 2005/0196450 A1 | 9/2005 | Touitou |
| 2005/0222276 A1 | 10/2005 | Schmaus et al. |
| 2005/0238602 A1 | 10/2005 | Modak et al. |
| 2006/0018867 A1 | 1/2006 | Kawasaki et al. |
| 2006/0051384 A1 | 3/2006 | Scholz et al. |
| 2006/0099237 A1 | 5/2006 | Modak et al. |
| 2006/0198800 A1 | 9/2006 | Dilallo et al. |
| 2006/0216246 A1 | 9/2006 | Belanger et al. |
| 2006/0233901 A1 | 10/2006 | Jamieson et al. |
| 2006/0293201 A1 | 12/2006 | Simon et al. |
| 2006/0293214 A1 | 12/2006 | Cheng et al. |
| 2007/0003538 A1 | 1/2007 | Madhyastha |
| 2007/0014823 A1 | 1/2007 | Iwata et al. |
| 2007/0020342 A1 | 1/2007 | Modak et al. |
| 2007/0027119 A1 | 2/2007 | Ahmed et al. |
| 2007/0190094 A1 | 8/2007 | Bessette et al. |
| 2007/0275070 A1 | 11/2007 | Ahmed et al. |
| 2007/0286813 A1 | 12/2007 | Toutounghi |
| 2008/0008729 A1 | 1/2008 | Swaine et al. |
| 2008/0038219 A1 | 2/2008 | Mosbaugh et al. |
| 2008/0063607 A1 | 3/2008 | Tamarkin et al. |
| 2008/0166314 A1 | 7/2008 | Jochim et al. |
| 2008/0226568 A1 | 9/2008 | Rozsa et al. |
| 2008/0234173 A1 | 9/2008 | Warr et al. |
| 2008/0253976 A1 | 10/2008 | Scott et al. |
| 2008/0260708 A1 | 10/2008 | Hall |
| 2008/0299220 A1 | 12/2008 | Tamarkin et al. |
| 2008/0311231 A1 | 12/2008 | Modak et al. |
| 2008/0317737 A1 | 12/2008 | Patel et al. |
| 2008/0318784 A1 | 12/2008 | Koo et al. |
| 2009/0004122 A1 | 1/2009 | Modak et al. |
| 2009/0028751 A1 | 1/2009 | Robbins |
| 2009/0029961 A1* | 1/2009 | Modak .................. A01N 47/44 514/184 |
| 2009/0035228 A1 | 2/2009 | Modak et al. |
| 2009/0068255 A1 | 3/2009 | Yu et al. |
| 2009/0088358 A1 | 4/2009 | Roso et al. |
| 2009/0165812 A1 | 7/2009 | Resnick et al. |
| 2009/0175806 A1 | 7/2009 | Modak et al. |
| 2009/0191288 A1 | 7/2009 | Squires et al. |
| 2009/0255536 A1 | 10/2009 | Av-Gay et al. |
| 2009/0300864 A1 | 12/2009 | Adkins et al. |
| 2010/0034871 A1 | 2/2010 | Mikkelsen et al. |
| 2010/0140368 A1 | 6/2010 | De Lame et al. |
| 2010/0172847 A1 | 7/2010 | Modak et al. |
| 2010/0172848 A1 | 7/2010 | Modak et al. |
| 2010/0183524 A1 | 7/2010 | Zielinski et al. |
| 2010/0196494 A1 | 8/2010 | Van Beek |
| 2010/0216889 A1 | 8/2010 | Modak et al. |
| 2010/0234460 A1 | 9/2010 | Foret et al. |
| 2010/0248962 A1 | 9/2010 | Wilczynski et al. |
| 2010/0317743 A1 | 12/2010 | Macinga et al. |
| 2010/0323043 A1 | 12/2010 | Perla et al. |
| 2011/0028563 A1 | 2/2011 | Found |
| 2011/0070376 A1 | 3/2011 | Wales et al. |
| 2011/0142899 A1 | 6/2011 | Lagaron Abello et al. |
| 2012/0100231 A1 | 4/2012 | Marc et al. |
| 2012/0129950 A1 | 5/2012 | Macinga et al. |
| 2012/0171156 A1 | 7/2012 | Basketter et al. |
| 2012/0201902 A1 | 8/2012 | Modak et al. |
| 2012/0207862 A1 | 8/2012 | Morre et al. |
| 2012/0258058 A1 | 10/2012 | Herrmann et al. |
| 2013/0052250 A1 | 2/2013 | Burgess et al. |
| 2013/0150452 A1 | 6/2013 | Modak et al. |
| 2013/0230609 A1 | 9/2013 | Modak et al. |
| 2014/0079819 A1 | 3/2014 | Debaun et al. |
| 2014/0178447 A1 | 6/2014 | Modak et al. |
| 2014/0242198 A1 | 8/2014 | Modak et al. |
| 2014/0243417 A1 | 8/2014 | Modak et al. |
| 2014/0287072 A1 | 9/2014 | Modak et al. |
| 2014/0322147 A1 | 10/2014 | Modak et al. |

FOREIGN PATENT DOCUMENTS

| | | |
|---|---|---|
| DE | 4240674 | 5/1996 |
| DE | 202008002718 U1 | 7/2009 |
| EP | 0 054 205 | 6/1982 |
| EP | 0 106 266 | 4/1984 |
| EP | 0 231 080 A1 | 8/1987 |
| EP | 0 313 302 | 4/1989 |
| EP | 0 328 421 | 8/1989 |
| EP | 0 379 271 | 7/1990 |
| EP | 0 472 413 | 2/1992 |
| EP | 0 604 848 | 7/1994 |
| EP | 0 663 212 | 7/1995 |
| EP | 0 882 461 | 12/1998 |
| EP | 1108419 | 6/2001 |
| EP | 1 146 112 | 10/2001 |
| EP | 1206933 | 5/2002 |
| EP | 1 288 285 | 3/2003 |
| FR | 2729050 | 7/1996 |
| FR | 2771632 | 6/1999 |
| FR | 2874928 | 3/2006 |
| GB | 1 060 447 | 3/1967 |
| GB | 2218617 | 11/1989 |
| JP | 1997-323910 | 12/1997 |
| JP | 11049625 | 2/1999 |
| JP | 2002-193717 | 7/2002 |
| JP | 2002-370958 | 12/2002 |
| JP | 2004-217615 | 8/2004 |
| JP | 04250331 | 9/2004 |
| JP | 2004277554 | 10/2004 |
| JP | 2004-322078 | 11/2004 |
| JP | 2006-225289 | 8/2006 |
| JP | 2007-291049 | 11/2007 |
| JP | 2010-083806 | 4/2010 |
| JP | 2010-184987 | 8/2010 |
| KR | 10-2004-077206 | 9/2004 |
| SU | 513676 | 5/1976 |
| WO | WO 1984/004556 | 11/1984 |
| WO | WO 1985/0001208 | 3/1985 |
| WO | WO 1989/0006962 | 8/1989 |
| WO | WO 1990/01956 | 3/1990 |
| WO | WO 1992/0004029 | 3/1992 |
| WO | WO 1993/002717 | 2/1993 |
| WO | WO 1993/06881 | 4/1993 |
| WO | WO 1993/017746 | 9/1993 |
| WO | WO 1996/22114 | 7/1996 |
| WO | WO 1997/025085 | 7/1997 |
| WO | WO 1998/051273 | 11/1998 |
| WO | WO 1999/022718 | 5/1999 |
| WO | WO 2000/037042 | 6/2000 |
| WO | WO 2000/057933 | 10/2000 |
| WO | WO 2000/065011 | 11/2000 |

(56) References Cited

FOREIGN PATENT DOCUMENTS

| WO | WO 2001/072262 | 10/2001 |
|----|----------------|---------|
| WO | WO 01/91555 | 12/2001 |
| WO | WO 2002/022060 | 3/2002 |
| WO | WO 2003/000303 | 1/2003 |
| WO | WO 2003/018498 | 3/2003 |
| WO | WO 2003/018743 | 3/2003 |
| WO | WO 2003/034994 | 5/2003 |
| WO | WO 2003/066001 | 8/2003 |
| WO | WO 2003/077856 | 9/2003 |
| WO | WO 2003/078367 | 9/2003 |
| WO | WO 2004/004631 | 1/2004 |
| WO | WO 2004/014416 | 2/2004 |
| WO | WO 2006/010269 | 2/2006 |
| WO | WO 2006/023349 | 3/2006 |
| WO | WO 2006/099359 | 9/2006 |
| WO | WO 2007/069214 | 6/2007 |
| WO | WO 2007/071089 | 6/2007 |
| WO | WO 2007/077573 | 7/2007 |
| WO | WO 2007/095041 | 8/2007 |
| WO | WO 2007/0101848 | 9/2007 |
| WO | WO 2007/123790 | 11/2007 |
| WO | WO 2007/126651 | 11/2007 |
| WO | WO 2008/031087 | 3/2008 |
| WO | WO 2008/042197 | 4/2008 |
| WO | WO 2008/061187 | 5/2008 |
| WO | WO 2008/119841 | 10/2008 |
| WO | WO 2008/154395 | 12/2008 |
| WO | WO 2008/157847 | 12/2008 |
| WO | WO 2009/062746 | 3/2009 |
| WO | WO 2009/049208 | 4/2009 |
| WO | WO 2010/091415 | 8/2010 |
| WO | WO 2010/119369 | 10/2010 |
| WO | WO 2011/002929 | 1/2011 |
| WO | WO 2011/151835 | 12/2011 |
| WO | WO 2012/017349 | 2/2012 |
| WO | WO 2012/051204 | 4/2012 |
| WO | WO 2013/066403 A1 | 5/2013 |
| WO | WO 2013/103556 A1 | 7/2013 |
| WO | WO 2014/092999 | 6/2014 |

OTHER PUBLICATIONS

U.S. Appl. No. 12/694,119 (US 2010/0172847), filed Jan. 26, 2010 (Jul. 8, 2010).
U.S. Appl. No. 12/016,788 (US 2009/0035228), filed Jan. 18, 2008 (Feb. 5, 2009).
U.S. Appl. No. 12/134,918, Apr. 22, 2015 Non-Final Office Action.
U.S. Appl. No. 12/694,119, May 8, 2015 Final Office Action.
U.S. Appl. No. 12/016,788, Mar. 6, 2015 Non-Final Office Action.
U.S. Appl. No. 12/016,788, Jun. 2, 2015 Response to Non-Final Office Action.
Baratta, et al., "Antimicrobial and antioxidant properties of some commercial essential oils", Flavour Fragr. J., 13, 235±244 (1998).
Biosource Naturals, product sheet for Lemongrass oil. Downloaded Apr. 5, 2015, from http://www.biosourcenaturals.com/lemongrass-essential-oil.htm.
Fact Sheet on Basil oil from Chemical Book, Downloaded Apr. 5, 2015, from http://www.chemicalbook.com/ChemicalProductProperty_US_CB3405198.aspx.
Prabuseenivasan, et al., "In vitro antibacterial activity of some plant essential oils", BMC Complementary and Alternative Medicine 2006, 6:39, pp. 1-8.
Skin Care, retrieved from URL:<https://web.archive.org/web/20050119140921/http://www.morganics.com/store/page8.html>, Jan. 19, 2005.
Subba, et al., "Antimicrobial Action of Citrus Oils" J. Food Sci. 1967, vol. 32, pp. 225-227.
Wilson, et al., "The quantification of citral in lemongrass and lemon oils by near-infrared spectroscopy", Journal of Pharmacy and Pharmacology 2002, 54: 1257-1263.
"Research on microbial biofilms (PA-03-047)." NIH, National Heart, Lung, and Blood Institute. Dec. 20, 2002.
Costerton, et al., "Biofilm in implant infections: Its production and regulation", J Artif Organs. Nov. 2005 vol. 28, Issue 11. pp. 1062-1068.
Darouiche, et al., "Efficacy of combination of chlorhexidine and protamine sulphate against device-associated pathogens", J Antimicrob Chemother, vol. 61, Issue 3 pp. 651-657 (Mar. 2008).
Gaonkar, et al., "Efficacy of a silicone urinary catheter impregnated with chlorhexidine and triclosan against colonization with Proteus mirabilis and other uropathogens", Infect Control Hosp Epidemiol, vol. 28, Issue 5 pp. 596-598. (May 2007).
Hall-Stoodley L. et al., "Bacterial biofilms: from the natural environment to infectious diseases", Nature Reviews Microbio. Feb. 2004 vol. 2, Issue 2. pp. 95-108.
Høiby N. et al., "Antibiotic resistance of bacterial biofilms", International Journal of Antimicrobial Agents, vol. 35, Issue 4 pp. 322-332 (Apr. 2010).
Høiby N. et al., "The clinical impact of bacterial biofilms", Int J Oral Sci. Apr. 2011 vol. 3, Issue 2 pp. 55-65.
Koopman, et al., "Inhibition of *Salmonella enterica* biofilm formation using small-molecule adenosine mimetics", Antimicrob Agents Chemother, vol. 59, Issue 1 pp. 76-84 (Oct. 2014).
Reid, G., "Biofilms in infectious disease and on medical devices", International Journal of Antimicrobial Agents, vol. 11, Issue 3-4 pp. 223-226 (May 1999).
Stensballe J. et al., "Infection Risk with Nitrofurazone-Impregnated Urinary Catheters in Trauma Patients: A Randomized Trial", Ann Intern Med, vol. 147, Issue 5 pp. 285-293 (Sep. 2007).
Stickler DJ, "Bacterial biofilms in patients with indwelling urinary catheters", Nature Reviews: Urology, vol. 5, Issue 11 pp. 598-608 (Nov. 2008).
U.S. Appl. No. 11/327,677 (U.S. Pat. 7,745,425), filed Jan. 6, 2006 (Jun. 29, 2010).
U.S. Appl. No. 12/136,530 (US 2008/0311231), filed Jun. 10, 2008 (Dec. 18, 2008).
U.S. Appl. No. 12/367,851 (US 2009/0175806), filed Feb. 9, 2009 (Jul. 9, 2009).
U.S. Appl. No. 12/694,141 (US 2010/0172848), filed Jan. 26, 2010 (Jul. 8, 2010).
U.S. Appl. No. 13/335,363 (US 2012/0201902), filed Dec. 22, 2011 (Aug. 9, 2012).
U.S. Appl. No. 13/412,464 (US 2013/0230609), filed Mar. 5, 2012 (Sep. 5, 2013).
U.S. Appl. No. 14/267,606 (US 2014/0242198), filed May 1, 2014 (Aug. 28, 2014).
U.S. Appl. No. 14/267,403 (US 2014/0243417), filed May 1, 2014 (Aug. 28, 2014).
U.S. Appl. No. 14/294,933 (US 2014-0287072), filed Jun. 3, 2014 (Sep. 25, 2014).
U.S. Appl. No. 14/323,843 (US 2014/0322147), filed Jul. 3, 2014 (Oct. 30, 2014).
U.S. Appl. No. 12/367,851, Feb. 5, 2010 Notice of Abandonment.
U.S. Appl. No. 12/136,530, Feb. 1, 2012 Notice of Abandonment.
U.S. Appl. No. 12/136,530, Sep. 22, 2009 Non-Final Office Action.
U.S. Appl. No. 12/136,530, Dec. 11, 2009 Response to Non-Final Office Action.
U.S. Appl. No. 12/136,530, Jun. 29, 2011 Non-Final Office Action.
U.S. Appl. No. 12/136,530, May 19, 2011 Amendment and Request for Continued Examination (RCE).
U.S. Appl. No. 12/136,530, Nov. 19, 2010 Final Office Action.
U.S. Appl. No. 12/136,530, Sep. 15, 2010 Response to Non-Final Office Action.
U.S. Appl. No. 12/136,530, Jun. 16, 2010 Non-Final Office Action.
U.S. Appl. No. 12/136,530, Jun. 2, 2010 RCE and Response to Final Office Action.
U.S. Appl. No. 12/136,530, Mar. 2, 2010 Final Office Action.
U.S. Appl. No. 11/327,677, Jun. 1, 2009 Non-Final Office Action.
U.S. Appl. No. 11/327,677, Aug. 27, 2009 Response to Non-Final Office Action.
U.S. Appl. No. 11/327,677, Nov. 2, 2009 Notice of Allowance.
U.S. Appl. No. 12/016,788, Oct. 24, 2011 Non-Final Office Action.
U.S. Appl. No. 12/016,788, Apr. 24, 2012 Response to Non-Final Office Action.
U.S. Appl. No. 12/016,788, Aug. 24, 2012 Final Office Action.

(56) References Cited

OTHER PUBLICATIONS

U.S. Appl. No. 12/016,788, Feb. 22, 2013 Amendment and Request for Continued Examination (RCE).
U.S. Appl. No. 12/016,788, Aug. 1, 2013 Non-Final Office Action.
U.S. Appl. No. 12/016,788, Jun. 19, 2014 Final Office Action.
U.S. Appl. No. 12/016,788, Dec. 18, 2014 Amendment and Request for Continued Examination.
U.S. Appl. No. 12/694,119, Oct. 12, 2011 Non-Final Office Action.
U.S. Appl. No. 12/694,119, Dec. 21, 2012 Amendment and Request for Continued Examination (RCE).
U.S. Appl. No. 12/694,119, Jun. 26, 2014 Non-Final Office Action.
U.S. Appl. No. 12/694,119, Dec. 18, 2014 Response to Non-Final Office Action.
U.S. Appl. No. 12/134,918, Mar. 28, 2012 Response to Non-Final Office Action.
U.S. Appl. No. 12/134,918, Nov. 15, 2011 Non-Final Office Action.
U.S. Appl. No. 12/134,918, Jul. 31, 2012 Final Office Action.
U.S. Appl. No. 12/134,918, Jan. 31, 2013 Amendment and Request for Continued Examination (RCE).
U.S. Appl. No. 12/134,918, Nov. 7, 2013 Non-Final Office Action.
U.S. Appl. No. 12/134,918, May 7, 2014 Response to Non-Final Office Action.
U.S. Appl. No. 12/134,918, Jan. 26, 2015 Amendment and Request for Continued Examination.
U.S. Appl. No. 12/694,141, Mar. 1, 2013 Notice of Abandonment.
U.S. Appl. No. 12/694,141, Mar. 28, 2012 Response to Non-Final Office Action.
U.S. Appl. No. 12/694,141, Nov. 28, 2011 Non-Final Office Action.
U.S. Appl. No. 12/694,141, Jul. 24, 2012 Final Office Action.
U.S. Appl. No. 13/335,363, Feb. 19, 2013 Non-Final Office Action.
U.S. Appl. No. 13/335,363, Nov. 1, 2013 Final Office Action.
U.S. Appl. No. 13/335,363, Aug. 15, 2013 Response to Non-Final Office Action.
U.S. Appl. No. 13/335,363, Apr. 1, 2014 Amendment and Request for Continued Examination (RCE).
U.S. Appl. No. 13/335,363, Dec. 18, 2014 Response to Non-Final Office Action.
U.S. Appl. No. 13/335,363, Mar. 4, 2015 Final Office Action.
U.S. Appl. No. 13/335,363, Apr. 21, 2015 Advisory Action.
U.S. Appl. No. 13/335,363, Apr. 28, 2015 Amendment and Request for Continued Examination (RCE).
U.S. Appl. No. 13/412,464, Feb. 8, 2013 Restriction Requirement.
U.S. Appl. No. 13/412,464, Sep. 19, 2013 Notice of Non-Compliant.
U.S. Appl. No. 13/412,464, Aug. 8, 2013 Response to Restriction Requirement.
U.S. Appl. No. 13/412,464, Jul. 7, 2014 Response to Non-Final Office Action.
U.S. Appl. No. 13/412,464, Feb. 17, 2015 Amendment and Request for Continued Examination (RCE).
U.S. Appl. No. 13/412,464, Apr. 20, 2015 Non-Final Office Action.
U.S. Appl. No. 13/412,464, Jun. 8, 2015 Response to Non-Final Office Action.
U.S. Appl. No. 13/412,464, Jun. 22, 2015 Final Office Action.
Entry for Lemongrass oil, downloaded Jul. 15, 2012 from internet site: https://www.essentialoils.co.za/essential-oils/lemongrass.htm.
Entry for Orange Oil, downloaded Jul. 15, 2012 from internet site: https://www.essentialoils.co.za/essential-oils/orange.htm.
Judžentiené, et al., "Characterisites of essential oil composition in the needles of young Scots pine (*Pinus sylvestris* L.) stands growing along an aerial ammonia gradient", *Chemija*, 17(4):67-73, 2006.
Kurita, et al., "Synergistic Antimicrobial Effect of Ethanol, Sodium Chloride, Acetic Acid and Essential Oil Components", *Agricultural Biology Chemistry*, 47(1):67-75, 1983.
Mohammad Najmul Ghani Khan; Khazaain-al-Advia, vol. II (20th century AD), Nadeem Yunus Printer/Sheikh Mohd Basheer & Sons, Lahore, 1911 AD p. 656.
Mohammad Najmul Ghani Khan; Qaraabaadeen Najm-al-Ghani (20th century AD), Munshi Nawal Kishore, Lucknow, (Second Edition) 1928 AD p. 566.
Mohammad Azam Khan; Muheet Azam vol. II (Part II) (19th century AD), Matba Nizami, Kanpur, 1898 AD p. 3.
Susruta; Susruta Samhita—Edited & translated by P.V. Sharma, vol. III: Chaukhamba Visvabharati, Varanasi, Edn. Ist, 2001. [Time of origin 1000 BC—5th century] p. 10.
Mohammad Azam Khan; Muheet-e-Azam vol. III (19th century AD), Matba Nizami, Kanpur, 1887 AD p. 261.
Mohammad Shareef Khan; Ilaaj-al-Amraaz (18th century AD), Afzal-al-Matabe, Barqi Press, Delhi, 1921 AD p. 357.
Siddhayogasamgrahah—Compiled by Yadavji Trikamji Acharya, Sri Baidyanath Ayurved Bhawan, Allahabad, Edn. 1st 1978 pp. 131-132.
Mohammad Najmul Ghani Khan; Khazaain-al-Advia, vol. III (20th century AD), Nadeem Yunus Printer/Sheikh Mohd Basheer & Sons, Lahore, 1926 AD p. 568.
Sarngadharacarya; Saringadhara Samhita—Translated by Smt. Shailaja Srivastava: Chaukhamba Orientalia, Varansai, Edn. 2nd, 1998. [Time of origin 13th century] pp. 431-432.
Ziya Al-Din Abdullah Ibn Al-Baitar; Al-Jaam'e-li-Mufradaat-al-Advia-wal-Aghzia, vol. IV (13th century AD), Matba Amra, Cario, Egypt, 1874 AD p. 57.
Abu Bakr Mohammad, Bin Zakariyya Al-Razi; Kitaab-al-Haawi-fil-Tibb, vol. ii (9th century AD), Dayerah-Al-Ma'aarof Is,amoa. Juderabad. 1976 AD p. 434.
Mohammad Shareef Khan; Ilaaj-al-Amraaz (18th century AD), Afzal-al-Matabe, Barqi Press, Delhi, 1921 AD p. 335.
Mohammad Azam Khan; Muheet-e-Azam vol. III (19th century AD), Matba Nizami Kanpur, 1887 AD p. 69.
Mohammad Najmul Ghani Khan; Khazaain-al-Advia, vol. II (20th century AD), Nadeem Yunus Printer/Sheikh Mohd Basheer & Sons, Lahore, 1911 AD p. 657.
Mohammad Azam Khan; Muheet-e-Azam vol. I (19th century AD), Matba Nizami, Kanpur, 1896 AD p. 257
Cakrapanidattah; Cakradattah—Translated by Indradeva Tripathi; Chaukhamba Sanskrit Samsthan (Varanasi), Ed. 4th 2002, p. 260.
Khazaain-al-advia, vol. III ($20^{th}$ Century AD) by Mohammad Najmul Ghani Khan; Nadeem Yunus Printer, Sheikh Mohd Basheer & Sons, Lahore, 1926 AD p. 1050.
Qaraabaadeen Najm-al-Ghani ($20^{th}$ Century AD) by Mohammad Najmul Ghani Khan; Munshi Nawal Kishore, Lucknow, (Second Edition) 1928 AD p. 492.
Khazaain-al-advia, vol. II ($20^{th}$ Century AD) by Mohammad Najmul Ghani Khan; Nadeem Yunus Printer, Sheikh Mohd Basheer & Sons, Lahore, 1911 AD p. 657.
Kitaab-al-Umdah-fil-Jeraahat, Part I ($13^{th}$ Century AD) by Aminud-daulah Abul Farj Ibn Al-Quff Maseehi; Dayerah-al-Ma'aarif Usmania, Hyberabad, 1937 AD pp. 234-235.
Kitaab-al-Umdah-fil-Jeraahat, Part I ($13^{th}$ Century AD) by Aminud-daulah Abul Farj Ibn Al-Quff Maseehi; Dayerah-al-Ma'aarif Usmania, Hyberabad, 1937 AD pp. 235-236.
Ziya Al-Din Abdullah Ibn Al-Baitar; Al-Jaam'e-li-Mufradaat-al-Advia-wal0Aghzia, vol. II ($13^{th}$ Century AD) Matba Amra, Cairo, Egypt, 1874 AD p. 84.
Sodhalanighantauh—(Namasangraha Va Gunasamgraha) by Sodhala; Edited by P.V. Sharma, Oriental Institute, Baroda, Edn., $1^{st}$, 1978 p. 116.
Khazaain-al-advia, vol. II ($20^{th}$ Century AD) by Mohammad Najmul Ghani Khan; Nadeem Yunus Printer, Sheikh Mohd Basheer & Sons, Lahore, 1911 AD pp. 342-343.
Kitaab-al-Haawi-fil-Tibb, vol. IX ($9^{th}$ Century AD) by Abu Bakr Mohammad Bin Zakariyya Al-Razi; Dayerah0al-Ma'aarif Usmania, Hyberabad, (First Edition) 1960 AD p. 194.
Khazaain-al-Advia, vol. I ($20^{th}$ Century AD) by Mohammad Najmul Ghani Khan; Nadeem Yunus Printer; Sheik Mohd Basheer & Sons, Lahore, 1911 AD p. 669.
Vagabhata; Astanga Hrdaya—(commentary by Arunadutta) edited by Bhisagacrya Harisastri Paradakara Vaidya: Chaukhamba Orientalia, Varanasi, Edn. $8^{th}$, 1998 [Time of origin $5^{th}$ Century] p. 890.
Mohammad Azam Khan; Muheet-e-Azam, vol. I ($19^{th}$ Century AD), Matba Nizami, 1896 AD p. 197.
Baiju, et al., "Development of a Novel Surface Disinfectant Composition Containing Essential Oils and Fruit Acid Against Nosoco-

(56) References Cited

OTHER PUBLICATIONS mial Pathogens Commonly Associated with Environmental Surfaces", *International Journal of Essential Oil Therapeutics*, vol. 2:9-14 (2008).

Bezic, et al., "Composition and antimicrobial activity of *Achillea clavennae* L. essential oil." *Phytother. Res.* 17(9):1037-1040 (2003).

Bion, 2008, "Acne Treatment Products" http://www.bion-research.com/acne_treatment_products.htm.

Bion, 2008, "Moderate to Severe Acne" http://www.bion-research.com/moderate_to_severe_acne.htm.

Brehm-Stecher et al., "Sensitization of *Staphylococcus aureus* and *Escherichia coli* to antibiotics by the sesquiterpenoids nerolidol, farnesol, bisabolol, and apritone", *Antimicrobial Agents and Chemotherapy*; 47(10):3357-3360 (2003).

de Abreu Gonzaga et al., "Composition and antibacterial activity of the essential oils from Zanthoxylum rhoifolium", Planta Med. 69(8):773-775 (2003).

Garcia, et al.; "Virucidal activity of essential oils from aromatic plants of San Luis, Argentina", *Phytother. Res.*, 17(9):1073-1075 (2003).

Gershon, et al., "Antifungal Properties of n-Alkanols, α, w-n-Alkanedoils, and w-Chloro-α-alkanols", *J. Pharm. Sci.*, 64(4):381-384 (2006).

Goren, et al., "Analysis of essential oil of *Coridothymus capitatus* (L.) and its antibacterial and antifungal activity", Z. Naturforsch., 58(9-10):687-690 (2003).

Hajhashemi, et al., "Anti-inflammatory and analgesic properties of the leaf extracts and essential oil of Lavandula angustifolia Mill", *J. Ethnopharmacol.* 89(1):67-71 (2003).

Kupferwasser, et al., "Acetylsalicylic Acid Reduces Vegetation Bacterial Density, Hematogenous Bacterial Dissemination, and Frequency of Embolic Events in Experimental *Staphylococcus aureus* Endocarditis Through Antiplatelet and Antibacterial Effects", *Circulation*, vol. 99:2791-2797 (1999).

Kupferwasser, et al., "Salicylic Acid Attenuates Virulence in Endovascular Infections by Targeting Global Regulatory Pathways in *Staphylococcus aureus*," *Clin. Invest.*, 112(2):222-233 (2003).

Minami et al., "The inhibitory effect of essential oils on herpes simplex virus type-1 replication in vitro", *Microbial Immunol.* 47(a):681-684 (2003).

Paranagama et al., "Fungicidal and anti-aflatoxigenic effects of the essential oil of *Cymbopogon citratus* (DC.) Stapf. (lemongrass) against *Aspergillus flavus* Link. isolated from stored rice", *Lett. Appl. Microbiol.*; 37(1):86-90 (2003).

Schuhmacher, et al., "Virucidal effect of peppermint oil on the enveloped viruses herpes simplex virus type 1 and type 2 in vitro", *Phytomedicine.*, 10:504-510 (2003).

Shin, "Anti-Aspergillus activities of plant essential oils and their combination effects with ketoconazole or amphotericin B", *Arch. Pharm. Res.*, 26(5):389-393 (2003).

Silva et al.,"Analgesic and anti-inflammatory effects of essential oils of Eucalyptus", *J. Ethnopharmacol.*, 89(2-3);277-283 (2003).

Valero, et al.,, "Antibacterial activity of 11 essential oils against Bacillus cereus in tyndallized carrot broth", Int. J. Food Microbiol., 85(1-2):73-81 (2003).

Velluti, et al., "Inhibitory effect of cinnamon, clove, lemongrass, oregano and palmarose essential oils on growth and fumonisin B1 production by Fusarium proliferatum in maize grain." *Int. J. Food Microbiol.*, 89:145-154 (2003).

Ayliffe, et al., "Hand disinfection: A comparison of various agents in laboratory and ward studies", *Journal of Hospital Infection*, 11(3):226-243 (1988).

Bettini Mercia de Fatima M., "Purification of Orange Peel Oil and Oil Phase by Vacuum Distillation", *Functional Food Ingredients and Nutraceuticals, Processing Technologies*, Edited by john Shi, CRC Press 2006, pp. 157-172.

Nazer, et al., "Combinations of food antimicrobials at low levels to inhibit the growth of *Salmonella* sv. Typhimurium: a synergistic effect?", *Food Microbiology*, 22:391-398 (2005).

Fang, et al., "Prospective clinical study of Hydron, a synthetic dressing, in delivery of an antimicrobial drug to second-degree burns", *J. Burn Care Rehabil.*, 8(3):206-209 (1987).

Fox, et al., "Comparative evaluation of zinc sulfadiazine and silver sulfadiazine in burn wound infection", *J. Burn Care Rehabil.*, 11(2):112-117 (1990).

Gaonkar, et al., "In vivo efficacy of an alcohol-based surgical hand disinfectant containing a synergistic combination of ethylhexylglycerin and preservatives", *Journal of Hospital Infection*, 63(4):412-417 (2006).

Gaonkar, et al., "An alcohol hand rub containing a synergistic combination of an emollient and preservatives: prolonged activity against transient pathogens", *Journal of Hospital Infection*, 59(1):12-18 (2005).

European Supplementary Search Report for EP 08780771.5, dated Dec. 17, 2012.

International Search Report and Written Opinion for PCT/US2012/052793, dated Nov. 19, 2012.

International Search Report and Written Opinion for PCT/US2012/063013, dated Jan. 4, 2013.

International Search Report and Written Opinion for PCT/US2012/037135, dated Oct. 16, 2012.

Choudhary, et al., "Solvent-free selective oxidation of benzyl alcohol and benzaldehyde by tert-butyl hydroperoxide using $MnO_4$-exchanged Mg-Al-hydrotalcite catalsysts", *Catalysis Letters*, 86(4):229-233 (2003).

Zhang, et al., "Antifungal Activities of Major Tea Leaf Volatile Constituents toward Colletorichum Camelliae Massea", *Journal of Agricultural and Food Chemistry*, 54(11):3936-3940 (2006).

"Sheer Moisturizer Hand Sanitizer", *Mintel Global New Products Database*, pp. 1-4 (2010) Retrieved from the Internet: URL:www.gnpd.com [Retrieved on Aug. 34, 2013].

"Antibacterial Wet Wipes", *Mintel Global New Products Database*, pp. 1-2 (2008) Retrieved from the Internet: URL:www.gnpd.com [Retrieved on Sep. 24, 2013].

Cowan, "Plant product as antimicrobial agents", *Clinical Microbiology Reviews*, 12(4):564-582 (1999).

Nannapaneni et al., "Antimicrobial activity of commercial citrus-based natural extracts against *Escherichia coli* O157:H7 isolates and mutant strains", *Foodborne Pathog Dis.*, 5(5):695-699 (2008).

International Search Report and Written Opinion for PCT/US2013/071731, dated Feb. 12, 2014.

International Search Report and Written Opinion for PCT/US2014/029486, dated Oct. 10, 2014.

Keeven et al., "Evaluating the preservative effectiveness of RGP lens care solutions", *The Contact Lens Association of Ophthalmologists Journal*, 21(4):238-241 (1995).

El-Zemity et al., "Antifungal activity of some essential oils and their major chemical constituents against some phytopathogenic fungi", *Journal of Pest Control and Enviromental Science*, 13(1):87-99 (2005).

"Parfums, Cosmetiques, Aromes: Japan approves sale of new cosmetics ingredient," Chemical Business Newsbase, Jan. 16, 2001.

(2000) "A-Z of exhibitors; at Central European Coatings Show." PPCJ. Polymers Paint Colour Journal, No. 4433, vol. 190: 42.

"Fraicheur de Peau Fresh Skin Body Mist," International Product Alert, No. 9, vol. 14, May 5, 1997.

"Happi, Household & Personal Products Industry: New ingredients galore at SCC supplier's day," Chemical Business Newsbase, Aug. 1, 2000.

"Schwarzkopf cares," European Cosmetic Markets, No. 5, vol. 13, May 1, 1996.

"Schwarzkopf: Moving into a new area," European Cosmetic Markets, No. 9, Sep. 1, 1996.

"Specific, Soap Perfumery and Cosmetics: New for deodorants: Sensiva SC 50," Chemical Business Newsbase, Aug. 12, 1999.

"Vichy launches oil-free moisturizer," Chemist & Druggist, p. 792, Jun. 8, 1996.

Beilfuss. (1998) "A multifunctional ingredient for deodorants." SOFW Journal, 1998, vol. 124: 360, 362-364, 366.

Bleasel, N. et al. (2002) "Allergic contact dermatitis following exposure to essential oils." Australian Journal of Dermatology. 43: 211-213.

(56) References Cited

OTHER PUBLICATIONS

Brehm-Stecher, et al. (2003) "Sensitization of *Staphylococcus aureus* and *Escherichia coli* to Antibiotics by the Sesquiterpenoids Nerolidol, Farnesol, Bisabolol, and Apritone." Antimicrob Agents and Chemotherapy vol. 47: 3357-3360.

Modak et al. (2005) "A Topical Cream Containing a Zinc Gel (Allergy Guard) as a Prophylactic against Latex Glove-Related Contact Dermatitis" Dermatitis, vol. 16:1-16.

Modak, S. M. et al. (1997) "A Topical Zinc Gluconate Gel Composition for the Prevention of latex/Starch Glove Related Allergic Reactions: Pilot Study in Volunteers." Programs and Abstracts of the 37th Interscience Conference on Antimicrobial Agents and Chemotherapy, Toronto: American Society for Microbiology Washington DC. Abstract J-52.

Robinson K "Heat beating technology; deodorant market," Soap Perfumery and Cosmetics, v. 69 No. 7 p. 34, Jul. 1996.

Sensiva® SC 50 product description from manufacturer website (www.schuelke-mayr.com), Schülke & Mayr, manufacturer, printed Apr. 4, 2001.

Woodruff, J "Mixed feelings," Soap Perfumery & Cosmetics, No. 9, vol. 73, p. 39, Sep. 1, 2000.

Raad, I. "Intravascular-catheter-related infections," *The Lancet*, 351:893-898 (1998).

Addy et al., "In vitro studies into the relaes of chlorohexidine acetate, predisolone sodium phosphate, and prednisolone alcohol from cold cure denture base acrylic", *Journal of Biomedical Materials Research*, 16:145-157 (1982).

Brook et al., "Controlling drug release from acrylic polymers: In Vitro studies with potential oral inserts", *Biomaterials*, 7:292-296 (1986).

Coventry et al., "Experimental use of a slow release device employing chlorhexidine gluconate in areas of acute periodontal inflamation", *J. of Clinical Periodontology*, 9:129-133 (1982).

Harper et al., "Simple additives to increase the activity of chlorhexidine digluconate against urinary pathogens", *Paraplegia*, 21:86-93 (1983).

Inman et al., "Prospective comparison of silver sulfadiazine 1 percent plus chlorhexidine digluconate 0.2 percent (Slivazine) and silver sulfadiazine 1 percent (Flazine) as prophylaxis against burn wound infection", *Burns*, 11:35-40 (1984).

Messing et al., "Antibiotic-Lock Technique is an Effective Treatment of Bacterial Catheter-Related Sepsis During Parenteral Nutrition", *Clinical Nutrition*, 9:220-225 (1990).

Mitchell et al., "Instrumental Bacteraemia and its prevention", *British Journal of Urology*, 34:454-458 (1962).

Nakano et al., "Efficacy of a latex foley catheter with sustained release of chlorohexidine: 1st Report, clinical Trials for Prevention of Urinary Tract Infection", *Hinyokika Kiyo*, 32(4):567-574 (1986).

Quesnel et al., "Synergism between chlorhexidine and sulphadiazine", *Appl. Bact.*, 45:397-405 (1978).

Paterson et al., "Urinary infection after colporrhapy: its incidence, causation and prevention", *Journal of Obstetrics and Gynecology*, 67:394-401 (1960).

Segura et al., "In Vitro Bacteriological Study of a New Hub Model for Intravascular Catheters and Infusion Equipment", *Journal of Clinical Microbiology*, 27(12):2656-2659 (1989).

Snelling et al., "Comparison of 1 percent silver sulfadiazine with and without 1 percent chlorhexidine digluconate for topical antibacterial effect in the burnt infected rat", *J. Burn Cap and Rehab*, 9(1):35-40 (1988).

Tuominen et al., "The effect of local antiseptic, chlorhexidine, in preventing infection from central venous catherization", *Abnnals of Clinical Research*, 13:425-428 (1981).

Huang et al., "Reduction of polysaccharide production in pseudomonas aeruginosa biofilms by bismuth dimercaprol (BisBAL) treatment", J. antimicorb. Chemother., 44:601-605 (1999).

Domenico et al., "Enhancement of bismuth antibacterial activity with lipophilic thiol chelators", Antimicrob Ag Chemother, 41:1697-1703 (1997).

Domenico et al., "Bismuth-dimercaprol exposes surface components of Klebsiella pneumoniae camouflaged by the polysaccharide capsule", Ann. NY Acad. Sci., 797:269-270 (1996).

Sheretz et al., "Efficacy of antibiotic-coated catheters in preventing subcutaneous *Staphylococcus aureus* infection in rabbits", J. Infect. Dis., 167:98-106 (1993).

Domenico et al., "Reduction of capsular polysaccharide and potentiation of aminoglycoside inhibition in gram-negative bacteria by bismuth subsalicylate", J. Antimicrob., 28:801-810 (1991).

Bierer, "Bismuth subsalicylate: history, chemistry, and safety", Rev. Inf. Dis., 12 Suppl 1:S3-S8 (1990).

Leon-Barau et al., "In vitro and in vivo effects of three bismuth compounds in fermentation by colonic bacteria", Rev. Inf. Dis., 12 Suppl 1:S24-S29 (1990).

Goodmand and Gillman's, The Pharmacological Basis of Therapeutics, Gilman et al., editors, Seventh Edition, 1985, Macmillan Publishing Company, New York, pp. 959-960, 1066-1067, 1171.

Mar. 8, 2000 Food and Drug Administration 510(k) Premarket Notification letter.

"Manufacturing Chemist: Japan approve Schülke & Mayr's Sensiva SC 50," Chemical Business Newsbase, Jul. 14, 2000.

"S & M in Japan—Schülke & Mayr's Sensiva SC 50 deodorant active ingredient received approval for use in the Japanese market," SPC Asia No. 21, p. 35, May 2000.

"SPC, Soap Perfumery and Cosmetics: New for deodorants: Sensiva SC 50," Chemical Business Newsbase, Aug. 12, 1999.

Baker, "Controlled Release of Biologically Active Agents", John Wiley & Sons, 1987, 279 pages (Table of Contents).

Gaonkar, et al. (2003) "Comparison of microbial adherence to antiseptic and antibiotic central venous catheters using a novel agar subcutaneous infection model." J. Antimicrobial Chemotherapy 52:389-396.

Greenfield, et al. (1995) "Decreased bacterial adherence and biofilm formation on chlorhexidine and silver sulfadiazine-impregnated central venous catheters implanted in swine." Crit Care Med. 23(5): 894-900.

Pacheco,-Fowler et al. (2004) "Antiseptic impregnated endotracheal tubes for the prevention of bacterial colonization." J Hospital Infection 57: 170-174.

Sampath, et al. (2001) "In vitro and in vivo efficacy of catheters impregnated with antiseptics or antibiotics: evaluation of the risk of bacterial resistance to the antimicrobials in the catheters." Infection Control and Hospital Epidemiology 22(10): 640-646.

Sampath, et al. (1995) "Infection resistance of surface modified catheters with either short-lived or prolonged activity" Journal of Hospital Infection vol. 30, 201-210.

Sampath, et al. (2001) "Safety and efficacy of an improved antiseptic catheter impregnated intraluminally with chlorhexidine." J of Infusion Nursing 24(6): 395-403.

Biosecur Lab. Inc., BiosecurTM Product Line Receives Self-Affirmed Gras Status for Use As an Antioxidant and Nutrient Supplement, News Release, Mar. 10, 2011, available at http://www.biosecur.com/news-rel ease/2011/BIOSECUR-GRAS-RELEASE-030811.pdf, accessed on Sep. 15, 2014.

Hazan et al., "Benzoic acid, a weak organic acid food preservative, exerts specific effects on intracellular membrane trafficking pathways in *Saccharomyces cerevisiae*", Applied and environmental Microbiology, 70(8):4449-4457 (2004).

Gaonkar et al., "Evaluation of the antimicrobial efficacy of urinary catheters impregnated with antiseptics in an in vitro urinary tract model", Infection Control and Hospital Epidemiology, 24:506-513 (2003).

Song et al., "Volatiles from Ficus hispida and their attractiveness to fig wasps", Journal of Chemical Ecology, 27:1929-1942 (Abstract only) (2001).

Komthong et al., "Ascending bubble extraction of terpenes from freshly squeezed orange juice", Food Research International, 39:53-58 (2006).

Kumar et al., "Assessment of *Thymus vulgaris* L. essential oil as a safe botanical preservative against post harvest fungal infestation of food commodities", Innovative Food Science & Emerging Technologies, 9(4):575-580 (Oct. 2008).

(56) References Cited

OTHER PUBLICATIONS

Gemeda et al., "Effect of essential oils on aspergillus spore germination, growth and mycotoxin production: a potential source of botanical food preservative", APJTB, 4(Suppl. 1):S373-381 (May 2014).
Pommier, et al, "Phase III Randomized Trial of Calendula Officinalis Compared With Trolamine for the Prevention of Acute Dermatitis During Irradiation for Breast Cancer," *J. Clin. Oncol*: 1447-1453, Apr. 15, 2004, p. 1447, Results, Conclusion.
U.S. Appl. No. 12/016,788, Oct. 22, 2015 Final Office Action.
U.S. Appl. No. 12/134,918, Jul. 31, 2015 Response to Non-Final Office Action.
U.S. Appl. No. 12/134,918, Nov. 4, 2015 Final Office Action.
U.S. Appl. No. 13/335,363, Jul. 8, 2015 Non-Final Office Action.
U.S. Appl. No. 12/134,911, Sep. 8, 2014 Notice of Allowance.
U.S. Appl. No. 12/134,911, Dec. 8, 2014 Issue Fee Payment.
"Lemongrass Oil: Lighten Up Your Mood with This All-Around Oil", Herbal Oil: Lemongrass Oil Benefits and Uses, 4 pages, 2015. http://articles.mercola.com/herbal-oils/lemongrass-oil.aspx.
Anand, et al., "Biological activities of curcumin and its analogues (Congeners) made by man and Mother Nature" Biochemical Pharmacology, 2008, vol. 76, pp. 1590-1611.
Bagamboula, et al., "Inhibitory effect of thyme and basil essential oils, carvacrol, thymol, estragol, linalool and p-cymene towards Shigella sonnei and S. flexneri" Food Microbiology 21 (2004) 33-42.
Chalchat, et al., Chemical Composition of Essential Oil of *Calendula oficinalis* L. (Pot Marigold). Flavour and Fragrance Journal, vol. 6, 189-192 (1991).
Chang, et al., Resources and bioactive substances from Taiwania (*Taiwania cryptomerioides*). J. Wood Sci (2003) 49:1-4.
Collins, et al., "A review of alternatives to organophosphorus compounds for the control of storage mites", Journal of Stored Products Research, vol. 42, No. 4, Jan. 1, 2006, pp. 395-426, XP028024314.
DailyMed Antiseptic skin cleanser—Chlorhexidine gluconate, Drug Label Information, updated Sep. 2012.
Nerio, et al., "Repellant activity of essential oils: A review", Biosource Technology, vol. 101, No. 1, Jan. 1, 2010, pp. 372-378, XP026624017.
Panchatcharam, et al., "Curcumin improves wound healing by modulating collagen and decreasing reactive oxygen species", Molecular and Cellular Biochemistry, vol. 290, No. 1-2, Jun. 13, 2006, pp. 87-96, XP019436632.
Reagor, et al., "The Effectiveness of Processed Grapefruit-Seed Extract as an Antibacterial Agent: I. An *In Vitro* Agar Assay" The Journal of Alternative and Complementary Medicine, 2002, vol. 8, pp. 325-332.
Supplementary Partial European Search Report dated Aug. 12, 2015 in Application No. 12846062.3.
Table of Acids with Ka and pKa, Downloaded Sep. 28 from the site: Downloaded Sep. 28, 2015, from http://clas.sa.ucsb.edu/staff/Resource%20folder/Chem109ABC/Acid,%20Base%20Strength/Table%20of%20Acids%20w%20Kas%20and%20pKas.pdf
Zeus Quimica, "Zemea Propanediol", Information sheet, downloaded Jun. 24, 2015.
U.S. Appl. No. 12/134,911 (U.S. Pat. No. 8,932,624), filed Jun. 6, 2008 (Jul. 13, 2015).
U.S. Appl. No. 14/194,381, filed Feb. 28, 2014.
U.S. Appl. No. 12/134,911, Feb. 18, 2011 Non-Final Office Action.
U.S. Appl. No. 12/134,911, Aug. 18, 2011 Response to Non-Final Office Action.
U.S. Appl. No. 12/134,911, Dec. 2, 2011 Final Office Action.
U.S. Appl. No. 12/134,911, May 2, 2012 Amendment and Request for Continued Examination (RCE).
EP Office Action dated Dec. 2, 2014 in EP Application No. 10 794 733.5.
U.S. Appl. No. 12/694,119, Feb. 2, 2016 Applicant Initiated Interview Summary.
U.S. Appl. No. 12/694,119, Jan. 20, 2016 Non-Final Office Action.
U.S. Appl. No. 14/267,606, Jan. 29, 2016 Non-Final Office Action.
Tecophilic TPU—LifeScience Polymers—The Lubrizol Corporation; "Tecophilic TPU"; https://web.archive.org/web/20140923074123/http://www.lubrizol.com/LifeScience/Products/Tecophilic.html; Sep. 23, 2014 [downloaded from internet Jan. 12, 2016]: entire document.
U.S. Appl. No. 12/955,432 (US 2011/0070316), filed Nov. 29, 2010 (Mar. 24, 2011).
U.S. Appl. No. 14/735,051 (US 2015/0265666), filed Jun. 9, 2015 (Sep. 24, 2015).
U.S. Appl. No. 14/194,381 (US 2014/0178447), filed Feb. 28, 2014 (Jun. 26, 2014).
U.S. Appl. No. 12/694,119, Nov. 5, 2015 Amendment and Request for Continued Examination (RCE).
U.S. Appl. No. 13/412,464, Sep. 11, 2015 Notice of Appeal Filed.
U.S. Appl. No. 14/194,381, Jan. 4, 2016 Non-Final Office Action.
U.S. Appl. No. 14/267,403, Nov. 17, 2015 Non-Final Office Action.
U.S. Appl. No. 14/294,933, Dec. 17, 2015 Non-Final Office Action.
Klaric et al., "Antifungal activity of thyme (*Thymus vulgaris* L.) essential oil and thymol against moulds from damp dwellings", 2006, The Society for Applied Microbiology, Letters in Applied Microbiology 44 (2007) 36-42.
Tayyem et al., "Curcumin Content of Turmeric and Curry Powders", Nutrition and Cancer, 55(2), 126-131, 2006.
U.S. Appl. No. 14/853,070 (US 2016/0000094), filed Sep. 14, 2015 (Jan. 7, 2016).
U.S. Appl. No. 14/294,933, Oct. 11, 2016 Issue Fee Payment.
U.S. Appl. No. 14/294,933, Jul. 18, 2016 Notice of Allowance.
U.S. Appl. No. 14/294,933, Jun. 2, 2016 Response to Non-Final Office Action.
U.S. Appl. No. 14/194,381, Jul. 28, 2016 Notice of Abandonment.
U.S. Appl. No. 12/955,432, Jul. 18, 2016 Issue Fee Payment.
U.S. Appl. No. 12/955,432, Apr. 19, 2016 Notice of Allowance.
U.S. Appl. No. 12/955,432, Jan. 29, 2016 Response to Restriction Requirement.
U.S. Appl. No. 12/955,432, Jul. 31, 2015 Restriction Requirement.
U.S. Appl. No. 12/955,432, Apr. 8, 2015 Response to Restriction Requirement.
U.S. Appl. No. 12/955,432, Oct. 8, 2014 Restriction Requirement.
Supplementary Partial European Search Report dated Jan. 5, 2017 in Application No. EP 14763192.
U.S. Appl. No. 14/267,403, Nov. 11, 2016 Response to Non-Final Office Action.
U.S. Appl. No. 14/267,403, Aug. 11, 2016 Non-Final Office Action.
U.S. Appl. No. 14/267,403, Mar. 17, 2016 Response to Non-Final Office Action.
EPO: Extended Search Report, European Patent Application No. 12845196.0, dated Sep. 5, 2016, pp. 1-9.
Jabra-Rizk et al., "Effect of Farnesol on *Staphylococcus aureus* Biofilm Formation and Antimicrobial Susceptibility," Antimicrobial Agents and Chemotherapy, 50(4):1463-1469 (2006).
O'Neil, Maryadele J. Editor, Entry for 'citral' in The Merck Index, 14th edition, pp. 388-389, Nov. 3, 2006, Publisher: Merck & Co., Published in: Whitehouse Station/Rahway, NJ.

* cited by examiner

BIO-FILM RESISTANT SURFACES

PRIORITY CLAIM

This application is a continuation in part of U.S. application Ser. No. 12/134,911 filed Jun. 6, 2008, which claims priority to U.S. Provisional Application Ser. No. 60/945,288, filed Jun. 20, 2007; and is a continuation in part of U.S. application Ser. No. 14/194,381, filed Feb. 28, 2014, which is a continuation of International Application No. PCT/US2012/052793, filed Aug. 29, 2012, which claims priority to U.S. Provisional Application Ser. No. 61/529,661, filed Aug. 31, 2011, and to U.S. Provisional Application Ser. No. 61/529,703, filed Aug. 31, 2011; the contents of each of which are hereby incorporated in their entireties herein, and priority to each of which is claimed.

1. INTRODUCTION

The present invention relates to methods and compositions for rendering a surface resistant to bio-film formation by a combination of an alkanediol and an antimicrobial agent (and, optionally, an organic hydroxy acid).

The present invention also relates to methods and compositions for rendering a surface resistant to bio-film formation by a combination of an antimicrobial agent, an organic acid releasing agent, and a lubricious biomedical polymer. In certain embodiments, the composition may further comprise an alkanediol.

2. BACKGROUND OF THE INVENTION

Whenever a medical article comes in contact with a patient, a risk of infection is created. Thus, a contaminated examination glove, tongue depressor, or stethoscope could transmit infection. The risk of infection dramatically increases for invasive medical articles, such as intravenous catheters, arterial grafts, endotracheal or intracerebral shunts and prosthetic devices, which not only are, themselves, in intimate contact with body tissues and fluids, but also create a portal of entry for pathogens.

A number of methods for reducing the risk of infection have been developed which incorporate anti-infective compounds into medical articles. Ideally, such articles provide effective levels of an anti-infective compound during the entire period that the article is being used. This sustained release may be problematic to achieve, in that a mechanism for dispersing an anti-infective compound over a prolonged period of time may be required, and the incorporation of sufficient amounts of anti-infective compound may adversely affect the surface characteristics of the article. The difficulties encountered in providing effective anti-microbial protection increase with the development of drug-resistant pathogens.

Two well known anti-infective compounds are chlorhexidine and triclosan. The following patents and patent applications relate to the use of anti-microbial compounds in medical articles.

U.S. Pat. No. 4,723,950 by Lee relates to a microbicidal tube which may be incorporated into the outlet tube of a urine drainage bag. The microbicidal tube is manufactured from polymeric materials capable of absorbing and releasing antimicrobial substances in a controllable, sustained, time-release mechanism, activated upon contact with droplets of urine, thereby preventing the retrograde migration of infectious organisms into the drainage bag. The microbicidal tube may be produced by one of three processes: (1) a porous material, such as poly-propylene, is impregnated with at least one microbicidal compound, and then coated with a hydrophilic polymer which swells upon contact with urine, causing the leaching-out of the microbicidal compound; (2) a porous material, such as high density polyethylene, is impregnated with a hydrophilic polymer and at least one microbicidal compound; and (3) a polymer, such as silicone, is compounded and co-extruded with at least one microbicidal compound, and then coated with a hydrophilic polymer. A broad range of microbicidal compounds are disclosed, including chlorhexidine and triclosan, and combinations thereof. The purpose of Lee's device is to allow the leaching out of microbicidal compounds into urine contained in the drainage bag; similar leaching of microbicidal compounds into the bloodstream of a patient may be undesirable.

U.S. Pat. No. 5,091,442 by Milner relates to tubular articles, such as condoms and catheters, which are rendered antimicrobially effective by the incorporation of a non-ionic sparingly soluble antimicrobial compound, such as triclosan. The tubular articles are made of materials which include natural rubber, polyvinyl chloride and polyurethane. Antimicrobial compound may be distributed throughout the article, or in a coating thereon. A condom prepared from natural rubber latex containing 1% by weight of triclosan, then dipped in an aqueous solution of chlorhexidine, is disclosed. U.S. Pat. Nos. 5,180,605 and 5,261,421, both by Milner, relate to similar technology applied to gloves.

U.S. Pat. Nos. 5,033,488 and 5,209,251, both by Curtis et al, relate to dental floss prepared from expanded polytetrafluoroethylene (PTFE) and coated with microcrystalline wax. Antimicrobial compounds such as chlorhexidine or triclosan may be incorporated into the coated floss.

U.S. Pat. No. 5,200,194 by Edgren et al. relates to an oral osmotic device comprising a thin semipermeable membrane wall surrounding a compartment housing a "beneficial agent" (that is at least somewhat soluble in saliva) and a fibrous support material composed of hydrophilic water-insoluble fibers. The patent lists a wide variety of "beneficial agents" which may be incorporated into the oral osmotic device, including chlorhexidine and triclosan.

International Patent Application No. PCT/GB92/01481, Publication No. WO 93/02717, relates to an adhesive product comprising residues of a co-polymerizable emulsifier comprising a medicament, which may be povidone iodine, triclosan, or chlorhexidine.

U.S. Pat. Nos. 5,019,096 and 5,616,338, both by Fox, Jr. et al. relate to infection-resistant medical articles comprising a synergistic combination of a silver compound (such as silver sulfadiazine) and chlorhexidine and their methods of manufacture, respectively. U.S. Pat. No. 5,334,588 by Fox, Jr. et al. relates to methods of inhibiting transmission of Hepatitis B virus using compositions comprising silver sulfadiazine and preferably further comprising a biguanide such as chlorhexidine and/or a detergent such as sodium deoxycholate.

U.S. Pat. Nos. 5,567,495, 5,772,640, 6,083,208 and 6,106,505 and U.S. patent publication Ser. Nos. 2001/0010016, 2001/0024661, 2002/0122876 and 2002/0173775, all by Modak et al., provide for, inter alia, anti-infective medical devices, either hydrophobic or hydrophilic, impregnated, coated, or impregnated and coated with various combinations of chlorhexidine, a silver salt such as silver sulfadiazine, silver oxide, silver carbonate or silver nitrate among others, a bismuth salt such as bismuth nitrate, bismuth citrate or bismuth salicylate among others, a zinc salt, a cerium salt, triclosan, combinations of chlorhexidine free base and chlorhexidine acetate, benzalkonium chloride, citrate, povidone iodine, parachlorometaxylene, gramicidin, polymixin, norfloxacin, tobramycin, sulfamylon, polyhexamethylene biguanide, alexidine, iodine, rifampicin, miconazole, bacitracin, and minocycline.

United States Patent Application Publication No. US 20060099237 A1 relates to combinations of octoxyglycerin and anti-infective compounds that synergistically increase the anti-infective properties of medical articles impregnated and/or coated with various combinations of octoxyglycerin and anti-infective compounds relative to the anti-infective properties of medical articles impregnated and/or coated with the same anti-infective compounds without octoxyglycerin.

Salicylic acid, an organic β-hydroxy acid, traditionally used as an antithrombogenic agent, has been recently shown to affect bacterial infection and virulence. In endocarditis, *Staphylococcus aureus* causes endovascular infections, damaging endothelial cells of valvular tissue. Salicylic acid appears to mitigate the virulent effects, reducing growth and cellular density of *S. aureus*-induced infective endocarditis in an animal model (Kupferwasser et al., 1999 "Acetylsalicylic Acid Reduces Vegetation Bacterial Density, Hematogenous Bacterial Dissemination, and Frequency of Embolic Events in Experimental *Staphylococcus aureus* Endocarditis Through Antiplatelet and Antibacterial Effects," Circulation, 99:2791-2797; Kupferwasser et al., "Salicylic acid attenuates virulence in endovascular infections by targeting global regulatory pathways in *Staphylococcus aureus*," J Clin Invest. 2003; 112(2):222-33). In fact, salicylic acid modulates virulence by suppressing expression of adherence factors (Kupferwasser et al., "Salicylic acid attenuates virulence in endovascular infections by targeting global regulatory pathways in *Staphylococcus aureus*," J Clin Invest. 2003; 112(2):222-33).

U.S. Pat. No. 6,582,719, International Patent Application No. PCT/US02/03087, and pending U.S. patent application Ser. No. 10/633,204, filed Jul. 30, 2003, all of which are incorporated by reference, disclose antimicrobial compositions comprising antiseptics, such as chlorhexidine, triclosan, and benzalkonium chloride, and antibiotics, such as minocycline, which may be particularly useful against antibiotic-resistant microorganisms. It has been discovered, however, that although certain of the chlorhexidine-containing solutions exhibited a broad spectrum of activity against many organisms, the solutions became unstable, forming precipitates after a few days at room temperature. Having a short shelf life limits the application of these compositions in coating and impregnating medical devices.

Alkanediols are emollient solvents used in various applications, including in the cosmetics industry. Alkanediols are reported to have anti-fungal activity (Gershon, 2006, J. Pharm. Sci. 69(4):381-384).

3. SUMMARY OF THE INVENTION

The present invention relates to methods and compositions for rendering a surface resistant to bio-film formation by a combination of an alkanediol and an antimicrobial agent (and, optionally, an organic hydroxy acid). It is based, at least in part, on the discovery that a combination of octanediol, chlorhexidine, and lactic acid was observed to inhibit the adherence of certain bacteria and yeast to a catheter surface.

The present invention also relates to methods and compositions for rendering a surface resistant to bio-film formation by a combination of an antimicrobial agent, an organic acid releasing agent, and a lubricious biomedical polymer. In certain embodiments, the composition may further comprise an alkanediol. In certain embodiments, the composition does not comprise an alkanediol. In certain embodiments, the composition does not comprise an anti-inflammatory agent. The present invention is based, at least in part, on the discovery that chlorhexidine free base was soluble in solvents such as tetrahydrofuran (THF) or alcohol, when the chlorhexidine was combined with an organic acid and a lubricious biomedical polymer, such that the chlorhexidine composition prevents adherence of bacteria and biofilm formation on a device surface, but does not release therapeutic amount of antimicrobials to prevent systemic infection.

In one set of non-limiting embodiments, the present invention provides for compositions which may be used to render a surface resistant to bio-film formation. Such compositions may be solutions for impregnating or coating an article, or wipes comprising such solutions.

In another set of non-limiting embodiments, the present invention provides for methods of rendering a surface resistant to bio-film formation which utilize the aforementioned solutions or wipes.

In yet another set of non-limiting embodiments, the present invention provides for articles having a bio-film resistant surface created according to the invention.

The present invention may be used in the context of surfaces of medical articles or other surfaces which are desirably protected from microbe adherence, such as surfaces in an environment associated with child care, food preparation, etc.

4. DETAILED DESCRIPTION OF THE INVENTION

For clarity of description and not by way of limitation, the detailed description of the invention is divided into the following subsections:

(i) antimicrobial agents;
(ii) organic acid releasing agents;
(iii) lubricious polymeric matrix;
(iv) alkanediols;
(v) hydroxy acids;
(vi) primer coating compositions
(vii) one-step coating methods;
(viii) two-step coating methods;
(ix) compositions for preparing a bio-film resistant surface;
(x) methods for producing a bio-film resistant surface; and
(xi) articles having a bio-film resistant surface.

"Bio-film resistant" as that term is used herein means that adherence of a microbe to the surface is inhibited.

4.1 Antimicrobial Agents

The present invention utilizes one or more biguanide, including, but not limited to, chlorhexidine, either as a free base, or a salt thereof, or a combination of free base and a chlorhexidine salt, poplyhexanide, and alexidine. Non-limiting examples include chlorhexidine diphosphanilate, chlorhexidine digluconate, chlorhexidine diacetate (also known as chlorhexidine acetate or CHA), chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluoro-phosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-.alpha.-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynaphthoate, and chlorhexidine embonate and combinations thereof. Other examples of biguanides are polyhexamethylene biguanide and alexidine biguanide.

Other antimicrobial agents which may, in addition to a biguanide, be used according to the invention include, but are not limited to, phenoxyethanol, a tetracycline compound such as minocycline, polymixin, octoxyglycerin, a chlorinated phenol such as parachlorometaxylenol (PCMX) or triclosan, silver salts, benzyl benzoate, povidone iodine, nitrofurazone, berberine, alkanediols, and a quaternary ammonium compound such as benzalkonium chloride or benzethonium chloride. Combinations of such agents may also be used.

In preferred non-limiting embodiments, an antimicrobial agent to be used together with a biguanide is a silver compound. The term silver compound, as used herein, refers to a compound comprising silver, either in the form of a silver atom or a silver ion unlinked or linked to another molecule via a covalent or noncovalent (e.g. ionic) linkage, including but not limited to covalent compounds such as silver sulfadiazine ("AgSD") and silver salts such as silver oxide ("$Ag_2O$"), silver carbonate ("$Ag_2CO_3$"), silver deoxycholate, silver salicylate, silver iodide, silver nitrate ("$AgNO_3$"), silver paraaminobenzoate, silver paraaminosalicylate, silver acetylsalicylate, silver ethylenediaminetetraacetic acid ("AgEDTA"), silver picrate, silver protein, silver citrate, silver lactate and silver laurate and combinations thereof.

In certain embodiments, the antimicrobial is present in the composition of the present application at a concentration of between about 0.01 and 10.0% w/v; or between about 0.05 and 7.0% w/v; or between about 0.05 and 5.0% w/v; or between about 0.1 and 2% w/v; or between about 0.1 and 1% w/v; or between about 0.1 and 0.5% w/v. In certain embodiments, the antimicrobial is present in the composition of the present application at a concentration between about 0.05 and 5.0% w/w.

In certain embodiments, the antimicrobial comprises chlorhexidine, for example, chlorhexidine base (CHX), chlorhexidine acetate (CHA) or CHA+CHX, at a concentration of between about 0.05 and 7.0% w/v. In certain embodiments the composition further comprises a second or more antimicrobial, wherein the second or more antimicrobials are present at a concentration of between about 0.02 and 3.0% w/w, or between about 0.05 and 3.0% w/v. In certain embodiments the second or more antimicrobial is selected from the group consisting of silver salt and/or chlorinated phenol, for example, PCMX.

4.2 Organic Acid Releasing Agents

The term "releasing agent" as used herein refers to an agent that promotes the release of antimicrobial agent(s), or other bioactive agent(s), from a lubricious polymer matrix. In certain embodiments, the antimicrobial agent is released in an amount such that the antimicrobial agent prevents adherence of bacteria and biofilm formation on a device surface, but is not released in an amount to prevent systemic infection. In certain embodiments, once all of the releasing agent has been released from the lubricious polymer matrix (e.g., after 2-3 days following insertion of a device coated with the lubricious polymer matrix into a subject), no further detectable release of antimicrobials from the lubricious polymer matrix occurs.

In certain embodiments, the releasing agent comprises one or more organic or fruit acid selected from citric acid, lactic acid, glycolic acid, mandelic acid, benzoic acid, salicylic acid, acetyl salicylic acid, ascorbic acid, and combinations thereof. In certain embodiments, the organic acid is present at a concentration of between about 0.01 and 7% w/v, or between about 0.05 and 5.0% w/v, or between about 0.05 and 4.0% w/v, or between about 0.1 and 5.0% w/v, or between about 0.1 and 2% w/v, or between about 0.1 and 1% w/v, or between about 0.1 and 0.5% w/v, or between about 0.2 and 5.0% w/v; or between about 0.1 and 5.0% w/v of the coating solution. In other non-limiting embodiments, the ratio of releasing agent to antimicrobial agent is between 1:0.5 and 1:10 and the ratio of releasing agent to the total amount of antimicrobial agent and/or additional bioactive agent is between 1:0.5 and 1:30.

In certain embodiments, the organic acid is present at a concentration of between about 0.2 and 2.05 w/w.

4.3 Lubricious Polymeric Matrix

A lubricious polymeric matrix as disclosed herein comprises a lubricious matrix system that comprises one or more biomedical polymer. "Lubricious" means that the matrix system provides a smooth and slippery surface which resists adherence of substances on the surface. In certain embodiments, the lubricious polymeric matrix described herein comprises hydrophilic-hydrophobic polymers that are used to as a matrix system to incorporate antimicrobials onto the surface of a device which renders the surface highly lubricious and avoids the need for an overcoat with hydrogels to improve surface lubricity.

In certain embodiments, the lubricious polymeric matrix does not comprise an anti-inflammatory agent.

Non-limiting examples of suitable biomedical polymers include one or more of biomedical polyurethane, for example, hydrophilic polyurethane, hydrophobic polyurethane, Tecoflex (aliphatic polyether-based polyurethanes), Pellethane or Estane polyurethane (thermoplastic polyurethanes) having Shore hardness of, for example, 70A, 80A, 93A, 100A, 50D, 55D, 60D, 65D, 70D, 70A to 70D durometer, 70A to 100A durometer and a 55D to 70D durometer. In certain embodiments the polyurethane is present at a concentration of between about 0.05 and 50% w/v, or between about 0.2 and 30% w/v, or between about 0.2 and 10.0% w/v, or between about 0.5 and 10% w/v, or between about 1 and 20% w/v, or between about 1 and 10% w/v.

Additional non-limiting examples of suitable biomedical polymers include one or more urethane adhesive. The urethane adhesive used can be from the medium to high viscosity Loctite Hysol® medical adhesive products, e.g. M-06FL, M-04FL, M-05 FL, M-09FL, M-31Cl, M-121HP, M-4981. In certain embodiments the urethane adhesive is present at a concentration of between about 0.2 and 30.0% w/v. In certain embodiments the urethane adhesive is Loctite Hysol® M-06FL.

Additional non-limiting examples of suitable biomedical polymers include one or more silicone polymer, such as a hydrophobic silicone polymer or silicone adhesive. The silicone adhesive can be silastic medical adhesive silicone type A (Dow corning), medical adhesive A-100 (Factor II, Inc.), silicone adhesive MDT7-4502 (Dow corning), and/or any other silicone polymer(s). In certain embodiments the silicone adhesive is present at a concentration of between about 0.05 and 50% w/v, or between about 0.2 and 30% w/v, or between about 0.2 and 10.0% w/v, or between about 1 and 10% w/v.

Additional non-limiting examples of suitable biomedical polymers include one or more water insoluble and/or matrix forming decanediol; biodegradable polymer such as polylactic acid, polyglycolic acid, PLA, PGA, Polycaprolactone (PCL); cellulose polymers such as hydrophilic, hydrophobic or hydrophilic-hydrophobic polymer (e.g., hydroxypropyl methyl-cellulose stearoxy ether (Sangelose)) either alone or in combination thereof, and hydrophobic matrix forming decanediol.

In certain embodiments, the biomedical polymer is present at a concentration of between about 0.01 and 6.0% w/v, or between about 0.01 and 5.0% w/v, or between about 0.2 and 30.0% w/v, or between about 0.3 and 20% w/v.

In certain embodiments, the biomedical polymer is present at a concentration of between about 0.2 and 5.0% w/w.

In particular non-limiting embodiments, the ratio of weight of total biomedical polymer to weight of antimicrobial agent(s) and any other bioactive agent(s), or combination thereof, is between 1:1 to 10:1.

In a non-limiting embodiment, a mixture of biomedical polymers is used to produce the lubricious matrix, said mixture comprising at least 5%, at least 10%, at least 20%, at least 50%, at least 60%, at least 70%, at least 80%, or at least 90% w/w of the biomedical polymers present.

In certain embodiments, the lubricious polymeric matrix further includes one or more solvents such as an alcohol (e.g. methanol, ethanol, isopropanol, and mixtures thereof), methyl-ethyl-ketone, acetone or tetrahydrofuran. In certain embodiments, the one or more solvent is present at a concentration of between about 10 and 70% v/v, or between about 2 and 20% v/v, or between about 10 and 50% v/v, or between about 20 an 70% v/v. In certain embodiments, the solvents described herein can be combined with other ingredients, such as an antimicrobial, in the absence of a biomedical polymer.

4.4 Alkanediols

Examples of alkanediols which may be used, according to the invention, include alkanediols having between about five and twenty-five carbon atoms in the backbone, including but not limited to pentanediol, hexanediol, heptanediol, octanediol, nonanediol, decanediol, undecanediol, dodecanediol, cyclodecanediol, tridecanediol tetradecanediol, pentanedecanediol, hexadecanediol, heptadecanediol, octadecanediol, nonadecanediokl, eicosanediol, heneicosanediol, docosanediol, tricosanediol, and pentacosanediol, where the preferred alkanediols include 1,2 decanediol, 1,10 decanediol, 1,2 dodecanediol, 1,12 dodecanediol, cyclododecanediol, 1, 13 tridecanediol, 1,2 tetradecanediol, 1,14 tetradecanediol, and especially preferred are 1,2 decanediol, 1,2 dodecanediol, 1,12 dodecanediol, and 1,2 tetradecanediol.

4.5 Hydroxy Acids

Organic hydroxy acids which may be used according to the invention include α-hydroxy acids as well as β-hydroxy acids. Non-limiting examples of such hydroxyacids include α-hydroxy acids such as lactic acid, glycolic acid, and citric acid and β-hydroxy acids such as salicylic acid, betahydroxybutanoic acid, tropic acid, and trethocanic acid.

4.6 Primer Coating Compositions

Also disclosed herein is a "primer" coating composition that may be applied to a device or surface that under usual conditions does not adhere well to standard coatings, for example that shows poor adherence to biomedical polyurethane coatings (for example, where the coating is not sufficiently adherent either in the initial application or under standard testing or clinical use conditions), where the primer coating renders the device or surface capable of being coated with either a standard coating or a lubricious coating as disclosed herein. In particular non-limiting embodiments, devices and surfaces in this category comprise (that is to say, at least a portion is fabricated from) a metal, for example titanium, stainless steel, or nitinol, or a silicone (e.g. a silicone polymer).

Specific non-limiting examples of urethane adhesives which may be used include from low to high viscosity Loctite Hysol® medical adhesive products, e.g. M-06FL, M-04FL, M-05 FL, M-09FL, M-11FL, M-31Cl, M-121HP, M-4981. Specific non-limiting examples of silicone adhesives which may be used include Dow Corning Silastic Medical Adhesive Type A, Medical Adhesive MD7-4502, and Medical Adhesive MD7-4602. Said "primer" coating may be used as a base coat to promote adherence of a second coating, e.g. a lubricious coating as disclosed herein, or may be used alone. Said primer coating, whether it underlies another coating layer or not, may optionally comprise one or more antimicrobial agent, one or more antiinflammatory agent, or one or more other bioactive agent, as described above.

The primer coating comprises a mixture of urethane and silicone adhesives, and optionally further comprises decanediol. The weight/weight ratio of urethane to silicone adhesive may be between about 1.25:1 to 125:1, or between about 2:1 and 20:1, or between about 2:1 and 6:1 or about 4:1, and the ratio of silicone adhesive to decanediol (if present) may be between about between 1:1 and 20:1 or between about 3:1 to 10:1 or about 5:1. In one non-limiting embodiment, the ratio of urethane adhesive:silicone adhesive:decanediol (if present) is about 20:5:1.

In one specific non-limiting embodiment a solution for creating the primer coating is as follows:

| Ingredient | % w/v | % w/v | Range (% w/v) |
| --- | --- | --- | --- |
| Hysol ® urethane adhesive | 20.0 | 20.0 | 5-30 |
| Silicone Medical Adhesive | 5.0 | 5.0 | 0.2-10 |
| Decanediol | 1.0 | 1.0 | 0.3-2.0 |
| Tetrahydrofuran | 74.0 | 74.0 | 60-90 |

After application, said coating may be allowed to dry (for example, until detectable solvent has evaporated or for at least about 2-3 hours) prior to use either as sole coating agent or as a base for subsequently applied coating(s). In a specific non-limiting embodiment the above solution may be used to coat a urinary catheter. Note that in this and similar tables, the column "% w/v" indicates a specific concentration and the column "Range (% w/v)" shows a range that may be used.

4.7 One-Step Coating Methods

The compositions described by the present application can be used as coatings that may be applied to a medical device or surface by a one-step method. Use of the term "one-step method" does not mean that it is not possible to apply one or more further coatings to the device or surface, but rather that a coating having the ingredients and properties set forth herein may be achieved in one step.

According to one embodiment, a one-step method comprises coating a device with a solution comprising and antimicrobial agent, alkanediol, and one or more releasing agents in a lubricious polymeric matrix system comprising biomedical polymers and solvents. In certain embodiments, the devices are dipped in the solution and dried at room temperature (e.g., 63-73 degrees Fahrenheit). In certain embodiments, the coating solution does not comprise alkanediol.

In certain embodiments, a one-step method of coating a surface of a device comprises coating the surface with a solution (e.g., by dipping the device in the solution), comprising (i) chlorhexidine base (0.5-5.0% w/v), (ii) releasing agent selected from lactic acid, mandelic acid, and a combination thereof (0.2-2.0% w/v), and (iii) decanediol (0.5-5.0% w/v), which are present in a lubricious matrix system comprising (i) Tecoflex polyurethane 93A, polyurethane 60D, or a combination thereof (0.5-5% w/v); (ii) a silicone medical adhesive selected from silicone medical adhesive Type A, medical adhesive MDT7-4502, and a combination thereof (1-5% w/v); optionally (iii) with or without urethane adhesive; in a solvent mixture comprising methanol (10-50% v/v) and/or THF (20-70% v/v). After coating a surface of the device, the coating is dried at room temperature.

In certain embodiments, the application provides the following non-limiting examples of formulations that may be used in a one-step coating method.

In certain non-limiting embodiments, a composition for coating a device is provided comprising the following ranges of ingredients:

Formulation-1

| Ingredients | Range (% w/v) |
| --- | --- |
| Chlorhexidine base | 0.1-5.0 |
| Decanediol | 0.1-5.0 |
| Mandelic acid | 0.1-5.0 |
| Lactic acid | 0-5.0 |
| Silver sulfadiazine | 0-2.0 |
| Silver carbonate | 0.0-1.0 |
| PU 93A | 0.2-5.0 |
| PU 60D | 0.1-2.0 |
| Silicone medical adhesive A-100 | 0.2-10.0 |
| Tetrahydrofuran (THF) | 50.0-80.0 |
| Methanol | 5.0-50.0 |

In certain embodiments, both latex and silicone catheters can be coated with this solution.

In certain non-limiting embodiments, a composition for coating a device is provided comprising the following concentrations of ingredients:

Formulation-1A

| Ingredients | % w/v |
| --- | --- |
| Chlorhexidine base | 2.0 |
| Decanediol | 2.0 |
| Mandelic acid | 2.0 |
| Lactic acid | 0.0 |
| Silver sulfadiazine | 0.0 |
| Silver carbonate | 0.0 |
| PU 93A | 2.66 |
| PU 60D | 0.66 |
| Silicone medical adhesive A-100 | 3.0 |
| Tetrahydrofuran (THF) | 72.68 |
| Methanol | 15.0 |

In certain embodiments, both latex and silicone catheters can be coated with this solution.

In certain non-limiting embodiments, a composition for coating a device is provided comprising the following concentrations of ingredients:

Formulation-2

| Ingredients | % w/v |
| --- | --- |
| Chlorhexidine base | 2.0 |
| Decanediol | 2.0 |
| Mandelic acid | 2.0 |
| Silver sulfadiazine | 0.75 |
| PU 93A | 2.66 |
| PU 60D | 0.66 |
| Silicone medical adhesive A-100 | 3.0 |
| Tetrahydrofuran (THF) | 71.93 |
| Methanol | 15.0 |

In certain non-limiting embodiments, a composition for coating a device is provided comprising the following concentrations of ingredients:

Formulation-3

| Ingredients | % w/v |
| --- | --- |
| Chlorhexidine base | 2.0 |
| Decanediol | 2.0 |
| Mandelic acid | 1.0 |
| Lactic acid | 1.0 |
| Silver sulfadiazine | 0.75 |
| PU 93A | 2.66 |
| PU 60D | 0.66 |
| Silicone medical adhesive A-100 | 3.0 |
| Tetrahydrofuran (THF) | 71.93 |
| Methanol | 15.0 |

In certain non-limiting embodiments, a composition for coating a device is provided comprising the following concentrations of ingredients:

Formulation-4

| Ingredients | % w/v |
| --- | --- |
| Chlorhexidine base | 2.0 |
| Decanediol | 2.0 |
| Mandelic acid | 2.0 |
| Silver carbonate | 0.3 |
| PU 93A | 2.66 |
| PU 60D | 0.66 |
| Silicone medical adhesive A-100 | 3.0 |
| Tetrahydrofuran (THF) | 72.38 |
| Methanol | 15.0 |

In certain non-limiting embodiments, a composition for coating a device is provided comprising the following concentrations of ingredients:

Formulation-5

| Ingredient | % w/v |
| --- | --- |
| Chlorhexidine base | 2.0 |
| Decanediol | 2.0 |
| Mandelic acid | 1.0 |
| Lactic acid | 1.0 |
| Silver carbonate | 0.3 |
| PU 93A | 2.66 |
| PU 60D | 0.66 |
| Silicone medical adhesive A-100 | 3.0 |
| Tetrahydrofuran (THF) | 72.38 |
| Methanol | 15.0 |

In certain non-limiting embodiments, a composition for coating a device is provided comprising the following concentrations of ingredients:
Formulation-6

| Ingredients | % w/v |
| --- | --- |
| Chlorhexidine base | 2.0 |
| Mandelic acid | 2.0 |
| Silver sulfadiazine | 0.75 |
| PU 93A | 2.66 |
| PU 60D | 0.66 |
| Silicone medical adhesive A-100 | 3.0 |
| Tetrahydrofuran (THF) | 73.93 |
| Methanol | 15.0 |

In certain non-limiting embodiments, a composition for coating a device is provided comprising the following ranges of ingredients:
Formulation-5 CVC

| Ingredients | Range (% w/v) |
| --- | --- |
| Chlorhexidine base | 0.1-5.0 |
| Decanediol | 0.1-5.0 |
| Mandelic acid | 0.1-3.0 |
| Lactic acid | 0.1-3.0 |
| Silver sulfadiazine | 0.0-2.0 |
| PU 93A | 0.2-8.0 |
| PU 60D | 0.1-3.0 |
| Silicone adhesive MDT7- 4502 | 0.2-5.0 |
| Tetrahydrofuran (THF) | 50.0-80.0 |
| Methanol | 5.0-50.0 |

In certain non-limiting embodiments, a composition for coating a device is provided comprising the following concentrations of ingredients:
Formulation-5 CVC A

| Ingredients | % w/v |
| --- | --- |
| Chlorhexidine base | 3.0 |
| Decanediol | 1.0 |
| Mandelic acid | 1.0 |
| Lactic acid | 1.0 |
| Silver sulfadiazine | 0.0 |
| PU 93A | 4.33 |
| PU 60D | 1.09 |
| Silicone adhesive MDT7- 4502 | 1.0 |
| Tetrahydrofuran (THF) | 71.33 |
| Methanol | 16.25 |

In certain non-limiting embodiments, a composition for coating a device is provided comprising the following concentrations of ingredients:
Formulation-6 CVC

| Ingredients | % w/v |
| --- | --- |
| Chlorhexidine base | 3.0 |
| Decanediol | 1.0 |
| Mandelic acid | 1.0 |
| Lactic acid | 1.0 |
| Silver sulfadiazine | 0.75 |
| PU 93A | 4.33 |
| PU 60D | 1.09 |
| Silicone adhesive MDT7- 4502 | 1.0 |
| Tetrahydrofuran (THF) | 70.58 |
| Methanol | 16.25 |

In certain non-limiting embodiments, a composition for coating a device is provided comprising the following ranges of ingredients:

| Ineredients | Range (% w/v) |
| --- | --- |
| Chlorhexidine base | 0.1-5.0 |
| Mandelic acid | 0.0-5.0 |
| Lactic acid | 0.1-5.0 |
| Ethanol | 50.0-90.0 |
| Tetrahydrofuran(THF) | 10.0-50.0 |

In certain non-limiting embodiments, a composition for coating a device is provided comprising the following concentrations of ingredients:
Formulation 1 CVC:

| Ingredients | % w/v |
| --- | --- |
| Chlorhexidine base | 2.0 |
| Mandelic acid | 1.0 |
| Lactic acid | 1.0 |
| Ethanol | 76.0 |
| Tetrahydrofuran | 20.0 |

*Ethanol and THF are % volume by volume

In certain non-limiting embodiments, a composition for coating a device is provided comprising the following concentrations of ingredients:
Formulation 2 CVC:

| Ingredients | % w/v |
| --- | --- |
| Chlorhexidine base | 2.0 |
| Lactic acid | 2.0 |
| Ethanol | 76.0 |
| Tetrahydrofuran | 20.0 |

*Ethanol and THF are % volume by volume

In certain non-limiting embodiments, a composition for coating a device is provided comprising the following ranges of ingredients:

| Ingredients | Range (% w/v) |
| --- | --- |
| Decanediol | 0.01-5.0 |
| PU 93A | 0.1-7.0 |
| PU 60D | 0.1-3.0 |
| Silicone medical adhesive A-100 | 0.2-10.0 |
| Tetrahydrofuran (THF) | 50.0-98.0 |

In certain embodiments, both latex and silicone catheters can be coated with the solution described above solution.

In certain non-limiting embodiments, a composition for coating a device is provided comprising the following concentrations of ingredients:

| Ingredients | % w/v |
| --- | --- |
| Decanediol | 2.0 |
| PU 93A | 2.66 |
| PU 60D | 0.66 |
| Silicone medical adhesive A-100 | 3.0 |
| Tetrahydrofuran (THF) | 91.68 |

In certain embodiments, both latex and silicone catheters can be coated with the solution described above solution.

Specific examples of coating solutions and methods set forth in the working example sections below are incorporated by reference into this section.

4.8 Two-Step Coating Methods

The compositions described by the present application can be used as coatings that may be applied to a medical device or surface by a two-step method. Use of the term "two-step method" does not mean that it is not possible to apply one or more further coatings to the device or surface, but rather that a coating having the ingredients and properties set forth herein may be achieved in two steps. The methods described in this section may be used to apply, to a device or surface, a first layer of coating which is a primer coating and a second layer of coating (over at least a portion of the first layer) which is a lubricious coating. In certain non-limiting embodiments, the methods may be used to coat devices that are fabricated from silicone or metal or that comprise one or more silicone or metal surface or area, among other substrates to which conventional biomedical polyurethane does not adequately adhere, although the scope of the disclosure also extends to coating devices or surfaces that could be satisfactorily coated with conventional biomedical polyurethane.

According to one embodiment, a two-step method comprises first coating a device with a primer coating comprising a lubricious polymeric matrix. In certain embodiments, the lubricious polymeric matrix primer coating comprises a combination of a urethane adhesive (e.g., at a concentration of between about 0.5 and 50% w/v, or between about 5 and 30% w/v, or between about 10 and 20% w/v), and a silicone adhesive (e.g., at a concentration of between about 0.05 and 50% w/v, or 0.1 and 20% w/v, or between about 0.2 and 10% w/v, or between about 0.2 and 5% w/v) dissolved in a solvent, for example, THF. In certain embodiments, the primer coating comprises an alkanediol, for example, decanediol, (e.g., at a concentration of between about 0.05 and 10% w/v, between about 0.01 and 5.0% w/v, or between about 0.1 and 1% w/v). In certain embodiments, the primer coating does not comprise an alkanediol. In certain embodiments, the primer coating is allowed to dry, for example, at room temperature for 3 hours, or until no detectable solvent is remaining.

In certain embodiments, the device treated with the primer coating is then coated with a second coating solution, wherein the second coating solution is applied over at least a portion of the primer coating layer, and comprises an antimicrobial and a releasing agent in a lubricious polymeric matrix comprising a combination of biomedical polymer and silicone adhesive. In certain embodiments, the coating is dried at room temperature. In certain embodiments, the second coating composition comprises one or more alkanediol. In certain embodiments, the second coating does not comprise an alkanediol.

In certain embodiments, a two-step method of coating a surface of a device comprises (i) coating a surface of a device with a primer coating comprising a combination of a urethane adhesive (e.g., Loctite Hysol® M-06FL) (5-50% (w/v), a silicone adhesive (e.g., silicone medical adhesive A) (1-10% w/v), and optionally with or without decanediol (0.01-5.0% w/v), which is dissolved in solvent (e.g., THF), and then dried at room temperature for 3 hours, or until no detectable solvent is remaining. The method further comprises (ii) coating the device with a second coating solution (e.g., by dipping the device in the second coating solution), wherein the second coating solution is applied over at least a portion of the primer coating layer, and wherein the second coating solution comprises chlorhexidine base (0.5-5.0% w/v); releasing agent (e.g., citric acid, lactic acid, mandelic acid, or a combination thereof) (0.2-2.0% w/v); decanediol (0.5-2.0% w/v); and a lubricious polymer matrix system comprising a biomedical polymer comprising polyurethane (e.g., Tecoflex polyurethane 93A, 60D) (1-5% w/v), silicone medical adhesive (silicone medical adhesive Type A, silicone medical adhesive MDT7-4502, or a combination thereof) ((1-5% w/v); optionally with or without urethane adhesive; in a solvent mixture comprising for example, methanol (10-50% v/v) and THF (20-70% v/v). The coated device is then dried at room temperature for 24-48 hours or at 40-50° C. for 3 hours, or until no detectable solvent is remaining.

In certain embodiments, the application provides the following non-limiting examples of formulations that may be used in a two-step coating method.

In certain non-limiting embodiments, compositions for coating a device using a two-step method are provided comprising the following ranges of ingredients:

Formulation-7
First Primer Coating:

| Ingredients | Range (% w/w) |
| --- | --- |
| Hysol ® urethane adhesive | 5-30 |
| Silicone medical adhesive | 0.2-10 |
| Decanediol | 0.3-2.0 |
| Tetrahydrofuran | 60-90 |

In certain embodiments, the catheters are dipped in the above mentioned first coating solution and dried at room temperature for 3 hours.

In certain embodiments, the catheters are then dipped in the following second coating solution and dried for 24-48 hours.

Second Coating:

| Ingredients | Range (% w/v) |
| --- | --- |
| Chlorhexidine base | 0.1-5.0 |
| Decanediol | 0.1-5.0 |
| Mandelic acid | 0.1-5.0 |
| Lactic acid | 0-5.0 |
| Silver sulfadiazine | 0-2.0 |
| Silver carbonate | 0.0-2.0 |
| PU 93A | 0.2-5.0 |
| PU 60D | 0.1-2.0 |
| Silicone medical adhesive A-100 | 0.2-10.0 |
| Tetrahydrofuran (THF) | 50.0-80.0 |
| Methanol | 5.0-50.0 |

In certain non-limiting embodiments, compositions for coating a device using a two-step method are provided comprising the following concentrations of ingredients:
Formulation-7A
First Coating:

| Ingredients | % w/w |
|---|---|
| Hysol ® urethane adhesive | 20.0 |
| Silicone medical adhesive | 5.0 |
| Decanediol | 1.0 |
| Tetrahydrofuran | 74.0 |

In certain embodiments, the catheters are dipped in the above mentioned first coating solution and dried at room temperature for 3 hours.

In certain embodiments, the catheters are then dipped in the following second coating solution and dried for 24-48 hours.
Second Coating:

| Ingredients | % w/v |
|---|---|
| Chlorhexidine base | 2.0 |
| Decanediol | 2.0 |
| Mandelic acid | 2.0 |
| Lactic acid | 0.0 |
| Silver sulfadiazine | 0.0 |
| Silver carbonate | 0.0 |
| PU 93A | 3.33 |
| PU 60D | 0.83 |
| Silicone medical adhesive A-100 | 3.0 |
| Tetrahydrofuran (THF) | 71.84 |
| Methanol | 15.0 |

In certain non-limiting embodiments, compositions for coating a device using a two-step method are provided comprising the following concentrations of ingredients:
Formulation-8
First Coating:

| Ingredients | % w/w |
|---|---|
| Hysol ® urethane adhesive | 20.0 |
| Silicone medical adhesive | 5.0 |
| Decanediol | 1.0 |
| Tetrahydrofuran | 74.0 |

In certain embodiments, the catheters are dipped in the above mentioned first coating solution and dried at room temperature for 3 hours.

In certain embodiments, the catheters are then dipped in the following second coating solution and dried for 24-48 hours.
Second Coating:

| Ingredients | % w/v |
|---|---|
| Chlorhexidine base | 2.0 |
| Decanediol | 2.0 |
| Mandelic acid | 2.0 |
| Silver sulfadiazine | 0.75 |
| PU 93A | 3.33 |
| PU 60D | 0.83 |
| Silicone medical adhesive A-100 | 3.0 |
| Tetrahydrofuran (THF) | 71.09 |
| Methanol | 15.0 |

In certain embodiments, the two-step method for coating a surface comprises the following method:
(a) exposing the surface to a first composition comprising
(i) one or more urethane adhesive present at a concentration of between about 5 and 50% w/v;
(ii) one or more silicone adhesive present at a concentration of between about 1 and 10% w/v;
(iii) one or more solvent;
(b) allowing the first solution to dry; and
(c) exposing the surface to a second composition comprising
(i) one or more antimicrobial agent present at a concentration of between about 0.05 and 7.0% w/v;
(ii) one or more releasing agent present at a concentration of between about 0.05 and 5.0% w/v; and
(iii) a lubricious biomedical polymeric matrix comprising
(1) one or more biomedical polymer present at a concentration of between about 0.2 and 30% w/v;
(2) decanediol present at a concentration of between about 0.01 and 5.0% w/v; and
(3) one or more solvent present at a concentration of between about 10 and 70% volume/volume (v/v).

Specific examples of coating solutions and methods set forth in the working example sections below are incorporated by reference into this section.

4.9 Compositions for Preparing a Bio-Film Resistant Surface

The present invention provides for compositions that may be used to prepare a bio-film resistant surface.

In a particular set of non-limiting embodiments, the present invention provides for a composition for preparing a bio-film resistant surface comprising a biguanide, an alkanediol, and a solvent, where the biguanide is present at between about 0.1 and 5 percent (weight/volume), or between about 2.5 and 4 percent (weight/volume), or between about 0.5 and 3 percent (weight/volume), and the alkanediol is present at between about 0.5 and 5 percent (volume/volume), and the solvent is selected from the group consisting of an alcohol (e.g. methanol, ethanol, isopropanol, and mixtures thereof) and tetrahydrofuran. In preferred non-limiting embodiments of the invention, the biguanide is chlorhexidine, such as chlorhexidine free base, chlorhexidine diacetate, chlorhexidine gluconate, or a mixture thereof, and the alkanediol is octanediol. Such compositions may further comprise one or more additional antimicrobial agent (in an amount between about 0.05 and 3 percent, preferably between about 0.2 and 1.5 percent (weight/volume), one or more hydroxy acid (in an amount between about 0.5 and 3 percent, preferably between about 0.2 and 2 percent (volume/volume), and/or one or more polymer (in an amount between about 1 and 3 percent or between about 1 and 20 percent or between about 1 and 10 percent, or between about 3 and 6 percent (weight/volume). In preferred non-limiting embodiments, the additional antimicrobial agent may be a silver compound, such as, but not limited to, silver sulfadiazine, the hydroxy acid may be lactic acid, and/or the polymer may be 93A polyurethane, 60D polyurethane, silastic medical adhesive type A, or a mixture thereof.

The term "about", as used throughout this document, means plus or minus 20 percent of the recited value.

The term "percent (weight/volume)" means the [weight of the referenced substance divided by the volume of the composition] multiplied by 100, or, in other words, the number of grams of the referenced substance in 100 milliliters of the composition.

As a specific non-limiting example, 100 ml of a composition comprising A percent biguanide (weight/volume), B percent alkanediol (volume/volume), C percent organic acid (volume/volume), D percent polymer (weight/volume) and E percent non-biguanide antimicrobial (weight/volume), in a solvent (which can be a mixed solvent), may be prepared by providing A grams of biguanide, D grams of polymer, E grams of non-biguanide antimicrobial, B mls of liquid form (e.g. melted) of alkanediol, and C mls of organic acid, adding each of these to solvent to form a solution and then solvent may be used to bring the total volume of the composition to 100 ml.

In non-limiting embodiments of the invention, a composition may be prepared by (i) dissolving biguanide, alkanediol, and optionally organic acid in an alcohol such as ethanol or methanol; (ii) dissolving polymer in tetrahydrofuran or equivalent solvent; and then (iii) mixing the solutions prepared in (i) and (ii).

In specific, non-limiting examples, the present invention provides for the following impregnation solutions, which may be used, not by way of limitation, to impregnate catheters such as polyurethane catheters, and also provides for medical articles, such as catheters (e.g. polyurethane catheters) impregnated therewith:

2% CHX+1.5% CHA+0.75% AgSD+1% Lactic acid+3% 93A PU+1% 60D PU+30% Methanol+60.75% THF ("CHX-CHA-AgSD-L");

2% CHX+1.5% CHA+0.75% AgSD+1% 1,2 Decanediol+1% Lactic acid+3% 93A PU+1% 60D PU+30% Methanol+59.75% THF ("CHX-CHA-AgSD-L-D");

2% CHX+1.5% CHA+0.75% AgSD+1% 1,12 Dodecanediol+1% Lactic acid+3% 93A PU+1% 60D PU+30% Methanol+59.75% THF ("CHX-CHA-AgSD-L-1,2 Dod");

2% CHX+1.5% CHA+0.75% AgSD+1% 1,12 Dodecanediol+1% Lactic acid+3% 93A PU+1% 60D PU+30% Methanol+59.75% THF ("CHX-CHA-AgSD-L-1,12 Dod");

2% CHX+1.5% CHA+0.75% AgSD+1% 1,2 Tetradecanediol+1% Lactic acid+3% 93A PU+1% 60D PU+30% Methanol+59.75% THF ("CHX-CHA-AgSD-L-1,14 TD");

2% CHX+1.5% CHA+0.75% AgSD+1% 1,2 Octanediol+1% Lactic acid+3% 93A PU+1% 60D PU+30% Methanol+59.75% THF ("CHX-CHA-AgSD-L-O");

3.5% CHX+0.75% AgSD+1% 1,2 Octanediol+1% Lactic acid+3% 93A PU+1% 60D PU+30% Methanol+59.75% THF ("CHX-AgSD-L-O"); and 3.5% CHA+0.75% AgSD+1% 1,2 Octanediol+1% Lactic acid+3% 93A PU+1% 60D PU+30% Methanol+59.75% THF ("CHA-AgSD-L-O").

In specific, non-limiting examples, the present invention provides for the following impregnation solutions, which may be used, not by way of limitation, for the impregnation of soft tissue patches (e.g., polytetrafluoroethylene ("PTFE") soft tissue patches ("STPs"), and also provides for medical articles, such as STPs (e.g. PTFE STPs) impregnated therewith:

0.1% Silver carbonate+0.2% CHX+0.15% CA+1% O ("S-CHX-CHA-O");

0.1% Silver carbonate+0.2% CHX+0.15% CHA+1% D ("S1-CHX-CHA-D"); and 0.05% Silver carbonate+0.2% CHX+0.15% CHA+1% D (S2-CHX-CHA-D), where S=Silver carbonate, D=1,2 Decanediol, and O=1,2 Octanediol.

In specific, non-limiting embodiments, the present invention provides for the following impregnation solutions which may be applied to silicone articles, e.g., urinary catheters, for example but not limited to as part of a two-step method, and also provides for medical articles, such as catheters, e.g. urinary catheters, e.g. silicone urinary catheters, impregnated therewith:

CHX-O: 2% (w/v) CHX+1% O+15% (w/v) Silastic Medical Adhesive Type A+1% glycerin+81% (v/v) THF;

CHX-D: 2% (w/v) CHX+1% D+15% (w/v) Silastic Medical Adhesive Type A+1% glycerin+81% (v/v) THF;

CHX-1,2Dod: 2% (w/v) CHX+1% 1,2 Dodecandiol+15% (w/v) Silastic Medical Adhesive Type A+1% glycerin+81% (v/v) THF;

CHX-1,12Dod: 2% (w/v) CHX+1% 1,12 Dodecanediol+15% (w/v) Silastic Medical Adhesive Type A+1% glycerin+81% (v/v) THF; OR CHX-TD: 2% (w/v) CHX+1% TD+15% (w/v) Silastic Medical Adhesive Type A+1% glycerin+81% (v/v) THF In specific, non-limiting embodiments, the present invention provides for the following impregnation solutions which may be applied to wound coatings, and also provides for wound coverings impregnated therewith:

Antimicrobial Composition 1

| Ingredients | (% w/w) |
| --- | --- |
| CHA | 0.15 |
| CHX | 0.15 |
| AgSD | 0.30 |
| Lactic Acid | 0.50 |
| 1,2 Decanediol | 0.50 |
| Polyurethane 93A | 0.40 |
| Polyurethane 60D | 0.10 |
| Methanol | 30.00 |
| Tetrahydrofuran | 67.90 |

Antimicrobial Composition 2

| Ingredients | (% w/w) |
| --- | --- |
| CHA | 0.15 |
| CHX | 0.15 |
| AgSD | 0.30 |
| Lactic Acid | 0.50 |
| 1,12 Dodecanediol | 0.50 |
| Polyurethane 93A | 0.40 |
| Polyurethane 60D | 0.10 |
| Methanol | 30.00 |
| Tetrahydrofuran | 67.90 |

Antimicrobial Composition 3

| Ingredients | (% w/w) |
| --- | --- |
| CHA | 0.15 |
| CHX | 0.15 |
| Silver Carbonate | 0.30 |
| Lactic Acid | 0.50 |
| 1,2 Decanediol | 0.50 |
| Polyurethane 93A | 0.40 |
| Polyurethane 60D | 0.10 |
| Methanol | 30.00 |
| Tetrahydrofuran | 67.90 |

Antimicrobial Composition 4

| Ingredients | (% w/w) |
|---|---|
| Polyhexamethylene biguanide | 0.30 |
| Silver Carbonate | 0.30 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 67.90 |

Antimicrobial Composition 5

| Ingredients | (% w/w) |
|---|---|
| CHA | 0.15 |
| CHX | 0.15 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 68.20 |

Antimicrobial Composition 6

| Ingredients | (% w/w) |
|---|---|
| Polyhexamethylene biguanide | 0.30 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 68.20 |

In a particular, non-limiting set of embodiments, a composition described in this section may be comprised in a wipe or a wound dressing.

In certain embodiments, the composition for use in coating a surface according to a one or two-step method as described herein includes the following:

(a) one or more antimicrobial agent present at a concentration of between about 0.05 and 7.0% weight/volume (w/v);

(b) one or more releasing agent present at a concentration of between about 0.05 and 5.0% w/v; and (c) a lubricious biomedical polymeric matrix comprising (i) one or more biomedical polymer present at a concentration of between about 0.2 and 30% w/v;

(ii) decanediol present at a concentration of between about 0.01 and 5.0% w/v; and (iii) one or more solvent present at a concentration of between about 10 and 70% volume/volume (v/v).

In certain embodiments, the composition for use in coating a surface according to a one or two-step method as described herein includes the following:

(a) one or more biomedical polymer present at a concentration of between about 0.2 and 30% w/v, wherein the;

(b) decanediol present at a concentration of between about 0.01 and 5.0% w/v; and (c) one or more solvent present at a concentration of between about 10 and 70% volume/volume (v/v).

In certain embodiments, the composition for use in coating a surface according to a one or two-step method as described herein includes the following:

(a) one or more antimicrobial present at a concentration of between about 0.05 and 7.0% w/v selected from the group consisting of chlorhexidine base, chlorhexidine acetate, and a combination of chlorhexidine base and chlorhexidine acetate; and (b) one or more solvent present at a concentration of between about 2 and 20% v/v selected from the group consisting of methyl-ethyl-ketone, methanol, ethanol, isopropanol, acetone, tetrahydrofuran, and combinations thereof; and (c) optionally a fruit acid present at a concentration between about 0.1 and 5.0% w/v selected from the group consisting of lactic acid, mandelic acid, and combinations thereof.

4.10 Methods for Producing a Bio-Film Resistant Surface

The present invention provides for methods of producing a bio-film resistant surface, comprising exposing the surface to a composition comprising a biguanide, an alkanediol, and a solvent, where the biguanide is present at between about 0.1 and 5 percent (weight/volume), or between about 2.5 and 4 percent (weight/volume) (where the article is to be "dipped" in the composition for a period of between about 5 seconds and 5 minutes or between about 5 seconds and 1 minute) or between about 0.5 and 3 percent (weight/volume), and the alkanediol is present at between about 0.5 and 5 percent (volume/volume) (Note that octanediol, for example, is a waxy solid but may be melted prior to adding to the solvent), and the solvent is selected from the group consisting of an alcohol (e.g. methanol, ethanol, isopropanol, and mixtures thereof), tetrahydrofuran and mixtures thereof. In preferred non-limiting embodiments of the invention, the biguanide is chlorhexidine, such as chlorhexidine free base, chlorhexidine diacetate, chlorhexidine gluconate, or a mixture thereof, and the alkanediol is octanediol. Such compositions may further comprise one or more additional antimicrobial agent (in an amount between about 0.05 and 3 percent, preferably between about 0.2 and 1.5 percent (weight/volume), one or more hydroxy acid (in an amount between about 0.5 and 3 percent, preferably between about 0.2 and 2 percent (volume/volume), and/or one or more polymer (in an amount between about 1 and 20 percent or between 1 and 30 percent or between about 1 and 10 percent, or between about 3 and 6 percent (weight/volume). In preferred non-limiting embodiments, the additional antimicrobial agent may be a silver compound, such as, but not limited to, silver sulfadiazine, the hydroxy acid may be lactic acid, and/or the polymer may be 93A polyurethane, 60D polyurethane, silastic medical adhesive type A, or a mixture thereof.

The surface may be exposed to the composition by immersing the surface in the composition or by applying the composition to the surface, for example by a spray, a stream, or a wipe.

In non-limiting embodiments of the invention, the composition may be exposed to the surface for a period of time such that the biguanide impregnates the surface.

In non-limiting embodiments of the invention, the composition may be exposed to the surface for a period of time such that the physical properties of the surface are altered, for example, where there is swelling of the surface; such alteration should not be such that the surface is damaged with regard to its intended use.

For example, where the surface is a surface of a catheter fabricated from a polymer, the catheter may be immersed in the composition and/or the composition may be introduced into the interior of the catheter. In one non-limiting embodiment, the ends of the catheter are sealed to prevent entry of the composition into the lumen. In another non-limiting embodiment, the composition is introduced into the interior of the catheter. In another non-limiting embodiment, the catheter may be briefly dipped into the composition. In non-limiting embodiments, a catheter surface is exposed to the composition for a period of between about 5 seconds and 5 hours, or between about 1 minute and 2 hours, or between about 5 seconds and 5 minutes, or between about 5 seconds and 1 minute.

In one particular set of embodiments, the present invention provides for a two-step method for providing a bio-film resistant surface. In the first step, an additional antimicrobial agent as set forth above, (for example, but not limited to, triclosan or a silver compound such as silver sulfadiazine), may be applied as a first solution comprising the antimicrobial agent at a concentration between about 0.05 and 3 percent (weight/volume), said solution optionally further comprising a hydroxy acid at a concentration between about 0.5 and 3 percent (volume/volume), in a solvent selected from the group consisting of an alcohol (e.g. methanol, ethanol, isopropanol, and mixtures thereof), tetrahydrofuran and mixtures thereof (preferably methanol). Biguanide, alkanediol, polymer and optionally hydroxy acid are applied in the second step, comprised in a solution wherein biguanide is present at between about 0.1 and 5 percent (weight/volume), or between about 0.5 and 3 percent (weight/volume), alkanediol is present at between about 0.5 and 5 percent (volume/volume), polymer is present at a concentration between about 1 and 20 percent or between about 1 and 10 percent or between about 3 and 6 percent (weight/weight) and the solvent is selected from the group consisting of an alcohol (e.g. methanol, ethanol, isopropanol, and mixtures thereof), tetrahydrofuran and mixtures thereof; hydroxy acid, where present, is in an amount of between about 0.5 and 3 percent (volume/volume). In each step, soaking may be for time intervals between about 5 seconds and 5 hours, or between about 1 minute and 2 hours, or between about 5 seconds and 5 minutes, or between about 5 seconds and 1 minute.

In a specific, non-limiting embodiment of the two-step method, in the first step, a solution containing about 30 percent THF (volume/volume), about 65 percent methanol (volume/volume), about 3 percent triclosan (TC) (weight/volume), and about 2 percent lactic acid (L) (volume/volume), may be used, into which a polyurethane catheter may be dipped for a time period of at least about 30 seconds or at least about one minute, and then allowed to dry, for example (but not by way of limitation) 48 hours (or however long drying requires). For the second step, a solution may be prepared containing about 30 percent methanol (volume/volume), about 63 percent THF (volume/volume), about 2 percent octanediol (O) (volume/volume), about 1 percent lactic acid (L)(volume/volume), about 4 percent chlorhexidine free base (CHX)(weight/volume), about 4 percent 93A polyurethane (weight/volume), and about 1 percent 60D polyurethane (weight/volume). (The polyurethanes may be first dissolved in THF and the other components may be dissolved in methanol and then the two resulting solutions may be mixed). The catheter resulting from the first step may be dipped into this solution for at least about 5 seconds, and then allowed to dry.

In another specific, non-limiting embodiment of the two-step method, in step 1, a silicone article (e.g. a catheter) or portion thereof may be soaked for 1 hour in a solution comprising about 0.3 percent triclosan (weight/volume) and about 1.0 percent lactic acid (volume/volume) in about 30 percent methanol (volume/volume)/about 67 percent THF (volume/volume). The catheter may be removed, dried, rinsed in water and dried again. In step 2, the catheter resulting from step 1 may be dipped in a solution comprising about 2 percent chlorhexidine free base (weight/volume), about 10 percent Silastic Medical Adhesive Type A (weight/volume), about 2 percent octanediol (volume/volume) and about 88 percent THF (volume/volume) (where THF is used to bring the volume to 100 percent) and dried.

In yet further specific non-limiting examples of the invention, silicone catheters, for example urinary catheters, may be impregnated by a two-step method as follows. Step 1: Catheters may be soaked for 1 hour in 0.3% Triclosan (T) (w/v)+1.0% L (Lactic Acid) (v/v) in 30% Methanol (v/v)+68.7% (v/v) THF. The catheters may be removed, dried for 1 hour, rinsed in water and dried for another hour. Step 2: Catheters may be dipped in the following solutions and dried for 24 hours and then used for testing:

CHX-O: 2% (w/v) CHX+1% O+15% (w/v) Silastic Medical Adhesive Type A+1% glycerin+81% (v/v) THF;

CHX-D: 2% (w/v) CHX+1% D+15% (w/v) Silastic Medical Adhesive Type A+1% glycerin+81% (v/v) THF;

CHX-1,2Dod: 2% (w/v) CHX+1% 1,2 Dodecandiol 15% (w/v) Silastic Medical Adhesive Type A+1% glycerin+81% (v/v) THF;

CHX-1,12Dod: 2% (w/v) CHX+1% 1,12 Dodecanediol+15% (w/v) Silastic Medical Adhesive Type A+1% glycerin+81% (v/v) THF; OR CHX-TD: 2% (w/v) CHX+1% TD+15% (w/v) Silastic Medical Adhesive Type A+1% glycerin+81% (v/v) THF.

4.11 Articles Having a Bio-Film Resistant Surface

The present invention provides for an article having at least one surface which is rendered bio-film resistant using the compositions and methods set forth above.

In non-limiting embodiments, the present invention provides for an article having at least one surface comprising, as active agents, a biguanide (e.g. chlorhexidine free base or a chlorhexidine salt) at between about 250 and 5000 $\mu g/cm^2$ of surface or between about 500 and 1000 $\mu g/cm^2$ of surface and an alkanediol (e.g. octanediol) at between about 200 and 1500 $\mu g/cm^2$ of surface, and optionally a hydroxy acid (e.g. lactic acid) at between about 100 and 800 $\mu g/cm^2$ of surface, and/or optionally a silver compound (e.g. AgSD) at between about 0-200 $\mu g/cm^2$ of surface.

In other non-limiting embodiments, the present invention provides for an article having at least one surface comprising, a biguanide (e.g. chlorhexidine free base), an organic acid releasing agent (e.g., citric acid, lactic acid, mandelic acid, or a combination thereof), and a lubricious polymer matrix. The surface may also optionally comprise one or more alkanediol, urethane adhesive and/or silicone adhesive.

Medical articles that may be treated according to the invention are either fabricated from or coated (e.g., to the entire device or a portion thereof) or treated with biomedical polymer and include, but are not limited to, indwelling medical devices such as catheters including urinary catheters and vascular catheters (e.g. peripheral and central vascular arterial and venous catheters), wound drainage tubes, arterial grafts, soft tissue patches, gloves, shunts, stents, tracheal catheters, wound dressings, bandages, drapes, intrauterine devices, intravaginal devices, sutures, staples, guide wires and prosthetic devices (e.g. heart valves and LVADs), contact lenses, needleless connectors, endotracheal tubes, mechanical heart valves, pacemakers, peritoneal dialysis catheters, prosthetic joints, tympanostomy tubes and voice prostheses. Vascular catheters that may be prepared according to the present invention include, but are not limited to, single and multiple lumen central venous catheters, peripherally inserted central venous catheters, emergency infusion catheters, percutaneous sheath introducer systems and thermodilution catheters, including the hubs and ports of such vascular catheters.

In non-limiting embodiments, articles made of substrates such as polyurethane, silicone rubber, natural rubber latex, polyvinyl chloride, as well as cotton, silk (wound dressings) can be treated with a composition of the invention.

In certain embodiments, devices coated with the compositions of the present application have a unique drug release pattern ideal for a biofilm resistant antimicrobial medical device, wherein the device prevents adherence of bacteria and biofilm formation on the device surface, but does not release a therapeutic amount of antimicrobials to prevent systemic infection.

In certain embodiments, devices prepared according to the methods described herein release about 30% of the antimicrobials present on a surface of the device, which inactivates microbes introduced at the insertion site of the device into a subject. As such, medical devices prepared according to the present application lower the potential for microbial colonization on the surface of device. The remaining antimicrobials persist on the surface of the device for a prolonged period of time, thus preventing subsequent microbial adherence and biofilm formation. Furthermore, devices coated according to the present application show higher antifungal activity.

In certain embodiments, the medical device substrates comprise: (i) polymers such as polyurethane, polyvinyl chloride (PVC), acrylonitrile butadiene styrene (ABS), acetals, polycarbonates, pebax, blends and alloys thereof, block Polymers, and Polytetrafluoroethylene (PTFE); (ii) rubber substrates such as silicone rubber, natural rubber latex, neoprene, isoprene, santoprene, and blends thereof; (iii) cotton, rayon, dacron, spandex, woven and non-woven materials; and (iv) metals such as titanium, stainless steel, nitinol, and combinations and alloys thereof.

Below are a series of working examples. The compositions, methods and articles described in the below working examples are hereby incorporated into this detailed description.

5. EXAMPLE 1: EFFECT ON ZONE OF INHIBITION

Polyurethane (PU) 7 Fr. central venous catheters (CVC) were treated with octanediol ("O"), lactic acid ("L") and chlorhexidine ("C")-containing solutions, in the presence or absence of other active agent.

Preparation of Coating Solution.

Two separate solutions were prepared, Solution A and Solution B, as follows:

Solution A: Chlorhexidine, octanediol, with or without lactic acid, in methanol; and Solution B: 93A polyurethane and 60D polyurethane in THF, and then the two solutions were mixed thoroughly prior to treatment. The amounts of active agents are set forth in Table 1, below, and the amount of polymer in the final solution, which was about 65 percent THF (volume/volume ("v/v")) and about 30 percent methanol (v/v) was 4 percent (weight/volume ("w/v")) 93A polyurethane and 1 percent (w/v) 60D polyurethane.

Impregnation of Catheters.

Catheters (6 cm in length, both ends sealed) were dipped in coating solutions prepared as above, containing active ingredients as indicated in Table 1. The catheters were dipped for 5 seconds in the solution and dried at room temperature for 24 hours and then used for testing.

TABLE 1

| Group | Composition |
|---|---|
| 1) | 4% CHX |
| 2) | 4% CHX + 3% L |
| 3) | 4% CHX + 3% O |
| 4) | 4% CHX + 2% O + 1% L |
| 5) | 3% CHX + 1% TC |
| 6) | 3% CHX + 1% TC + 2% O + 1% L |
| 7) | 3% CHX + 1% AgSD |
| 8) | 3% CHX + 1% AgSD + 2% O + 1% L |

NOTE:
CHX = Chlorhexidine free base

Zone of Inhibition (ZOI) Test.

Three 0.5 cm segments of each group of catheters, prepared as described above, were embedded vertically in modified trypticase soy agar (TSA) media seeded on the surface with 0.3 ml of $10^8$ colony forming units (CFU) per ml of bacteria or $10^5$ cfu/ml of yeast and the plates were incubated at 37° C. for 24 hours. The diameters of zones of inhibition of bacterial growth around the catheter segments were measured. The results are presented in Table 2.

TABLE 2

| | | Zone of Inhibition (mm) | | |
|---|---|---|---|---|
| Group | Active Agents | P. aeruginosa | S. aureus | C. albicans |
| 1) | 4% CHX | 11.0 | 13.0 | 12.0 |
| 2) | 4% CHX + 3% O | 11.5 | 13.0 | 12.0 |
| 3) | 4% CHX + 3% L | 11.0 | 13.0 | 12.0 |
| 4) | 4% CHX + 2% O + 1% L | 11.0 | 13.5 | 12.0 |
| 5) | 3% CHX + 1% TC* | 9.5 | 14.0 | 12.0 |
| 6) | 3% CHX + 1% TC + 2% O + 1% L | 11.0 | 15.0 | 12.0 |
| 7) | 3% CHX + 1% AgSD | 9.5 | 12.0 | 11.0 |
| 8) | 3% CHX + 1% AgSD + 2% O + 1% L | 11.5 | 13.5 | 13.0 |
| 9) | 5% O + 3% L | 0 | 8.0 | 0 |

*TC is triclosan.

Conclusion:

The zone-inhibiting activity was not significantly different between the group containing O+L and the group without O+L.

6. EXAMPLE 2: EFFECT ON MICROORGANISM ADHERENCE

Bacterial adherence on Polyurethane (PU) 7 Fr. (white) central venous catheters (CVC) treated with O+L+C and other antiseptics, as set forth in the preceding section, was evaluated using an in vitro agar track model.

Agar Tract Model.

The medium used was 0.5% agar (w/v) 20% bovine adult serum (BAS) (v/v)+0.5% milk (v/v)+0.03% trypticase soy broth medium powder (TSB) (w/v) in phosphate buffered saline (PBS). First, agar and TSB was dissolved in PBS, and a magnetic stirring rod was included in the flask. The medium was sterilized by autoclaving at 121° C. for 20 min. After autoclaving, it was allowed to cool down to 45-48° C. in a water bath put on a magnetic stirrer. Then, BAS and milk were warmed to room temperature, and 5 ml of milk were mixed with 5 ml BAS in a sterile culture tube and added to the agar/TSB-containing flask with gentle stirring. Then the remaining amount of BAS was added to the flask. The medium was maintained at 45-48° C. 12.5 ml aliquots of medium were dispensed into different culture tubes and allowed to solidify at room temperature.

Evaluation of Bacterial Adherence.

Catheter segments, 4 cm long and sealed at both ends, were inserted vertically into the center of the medium in each tube with 0.5 cm of the catheter protruding out of the medium. The caps of each tube were sealed with parafilm to prevent dessication. 5 catheter segments were used for each test. Untreated catheter segments were used as the control.

After 30 minutes, each catheter segment was lifted up (approximately 0.5 cm) and 25 µl of the culture (1-3×10$^8$ cfu/ml of *P. aeruginosa* or 1-3×10$^6$ cfu/ml *C. albicans*) was added on the catheter just near the surface of the medium so that the inoculum was also spread on medium surface. The catheter was then placed back to its original position and incubated at 37° C. for 7 days.

Then, the catheter segments were removed from the tubes and blotted on tissue. They were rinsed twice in 10 ml saline (6 segments/10 ml saline) and blotted dry. 0.5 cm was then cut off from both the ends of each catheter segment. Each catheter segment was then put in 4 ml LTSB (drug inactivating medium) in a culture tube and sonicated for 20 min. 0.5 ml aliquot from each tube was then plated out on TSA plates and incubated for 24-48 h. The results are shown in Table 3 (adherence of *P. aeruginosa*) and Table 4 (adherence of *C. albicans*).

TABLE 3

*P. aeruginosa* adherence (infected 30 minutes after implantation)

| | | Adherence of *P. aeruginosa* | |
|---|---|---|---|
| Group | Active agents | CFU/cm | Log10 Reduction from control counts |
| Control | (uncoated) | 1.1 × 10$^4$ | — |
| 1) | 4% CHX | 1.8 × 10$^3$ | 0.78 |
| 2) | 4% CHX + 3% L | 8.3 × 10$^2$ | 1.14 |
| 3) | 4% CHX + 3% O | 1.8 × 10$^2$ | 1.78 |
| 4) | 4% CHX + 2% O + 1% L | 92 | 2.08 |
| 5) | 3% CHX + 1% TC | 8.9 × 10$^2$ | 1.04 |
| 6) | 3% CHX + 1% TC + 2% O + 1% L | 1.1 × 10$^2$ | 2.0 |
| 7) | 3% CHX + 1% AgSD | 5.8 × 10$^2$ | 1.28 |
| 8) | 3% CHX + 1% AgSD + 2% O + 1% L | 4 | 3.44 |
| 9) | 3% O + 3% L | 9 × 10$^3$ | 0.1 |

TABLE 4

*C. albicans* adherence (infected 30 minutes after implantation)

| | | Adherence of *C. albicans* | |
|---|---|---|---|
| Group | Active agents | CFU/cm | Log10 Reduction from control counts |
| Control | (uncoated) | 2.9 × 10$^3$ | — |
| 1) | 4% CHX | 1.0 × 10$^3$ | 0.5 |
| 2) | 4% CHX + 3% L | 1.1 × 10$^3$ | 0.46 |

TABLE 4-continued

*C. albicans* adherence (infected 30 minutes after implantation)

| | | Adherence of *C. albicans* | |
|---|---|---|---|
| Group | Active agents | CFU/cm | Log10 Reduction from control counts |
| 3) | 4% CHX + 3% O | 1.9 × 10$^2$ | 1.2 |
| 4) | 4% CHX + 2% O + 1% L | 4 | 2.9 |
| 5) | 3% CHX + 1% TC | 90 | 1.5 |
| 6) | 3% CHX + 1% TC + 2% O + 1% L | 0 | 3.5 |
| 7) | 3% CHX + 1% AgSD | 44 | 1.9 |
| 8) | 3% CHX + 1% AgSD + 2% O + 1% L | 0 | 3.5 |

Conclusions.

As regards *P. aeruginosa* adherence, catheters having surfaces treated with C+O and C+O+L showed lower adherence. Of all the groups C and AgSD with O and L had significantly lower adherence. This result indicates that biofilm formation and bacterial adherence on medical devices can be significantly reduced by treating the device with an antimicrobial solution containing C+O+L.

As regards *C. albicans* adherence, the group of catheters having surfaces treated with O and L showed significantly lower adherence.

7. EXAMPLE 3: TWO-STEP COATING METHOD

In the preceding sections, catheters were coated with CHX+T+O+L along with a polymer by a dip method. With dipping, the percent of CHX in the solution is preferably in the range of 2.5-4%, for the catheter to be effective especially against *P. aeruginosa* (ZOI more than 10 mm) and *C. albicans* (ZOI more than 13 mm). For long term efficacy against *S. aureus*, a ZOI greater than 15 mm is most preferred. The catheters coated by the one step dipping method show effective ZOI against *P. aeruginosa* and *C. albicans*. However the ZOI against *S. aureus* is about 15 mm when CHX+Triclosan is 3%+1% (w/v) in the coating solution. Increasing the Triclosan in the coating solution can increase the efficacy against *S. aureus*. However, Triclosan has essentially no activity against *P. aeruginosa*. Furthermore, coating catheters with solutions containing higher concentrations of Triclosan may lower the amount of CHX uptake by the catheter (since the ratio of CHX to Triclosan will be lower) which results in lower efficacy against *P. aeruginosa*.

In order to provide a catheter which is effective, for extended periods, against *P. aeruginosa*, *C. albicans* and *S. aureus*, a two step method was developed by which higher concentrations of both triclosan and chlorhexidine could be incorporated along with octanediol and lactic acid.

According to the two-step method, triclosan and lactic acid is applied to the surface in the first step, and chlorhexidine, octanediol, lactic acid and polymer is applied in the second step.

For the first step, a solution containing about 30 percent THF (v/v), about 65 percent methanol (v/v), about 3 percent triclosan (TC) (w/v), and about 2 percent lactic acid (L) (v/v), was prepared. For example, for each about 100 ml of solution to be prepared, 30 ml THF, 65 ml Methanol, 3 g Triclosan, and 2 ml Lactic acid are mixed. A portion of a polyurethane 7 fr. blue catheter, with the top end sealed to prevent entry of liquid into the catheter, was soaked in this solution for 1 minute and then allowed to dry for 48 hours.

For the second step, a solution was prepared containing about 30 percent methanol (v/v), about 63 percent THF (v/v), about 2 percent octanediol (O) (v/v), about 1 percent lactic acid (L)(v/v), about 4 percent chlorhexidine free base (CHX)(w/v), about 4 percent 93A polyurethane (w/v), and about 1 percent 60D polyurethane (w/v). This solution was first prepared by dissolving the chlorhexidine, lactic acid and octanediol in the methanol, dissolving the polyurethanes in the THF, and then mixing the solutions together. For example, for each about 100 ml of solution to be prepared, 2 ml octanediol, 1 ml lactic acid, and 4 mg chlorhexidine are dissolved in 30 ml methanol, and 4 g 93A polyurethane and 1 g 60D polyurethane are dissolved in 63 ml THF, and then the methanol and THF solutions are mixed. Then, the catheter from Step 1 was dipped into this solution for 5 seconds and dried at room temperature overnight.

Control (uncoated) catheters, catheters treated by a one-step method, or by the two-step method described above, were prepared, as follows:

1) Control (uncoated catheter)
2) Catheter by 2 steps (Step 1 3% T+2% L) and Step 2 (4% CHX+1% L+2% O)
3) Catheter by 1 step (3% CHX+1.0% T+2% O+1% L)

The zones of inhibition for each of these catheters were then determined, using methods as set forth in Example 1, above. The results are presented in Table 5.

TABLE 5

| Group | Zone of Inhibition (mm) | | |
|---|---|---|---|
| | P. aeruginosa | S. aureus | C. albicans |
| 1 (control) | 0 | 0 | 0 |
| 2 (2-step) | 12.5 | 17.0 | 14.5 |
| 3 (1-step) | 11.0 | 15.0 | 12.0 |

Conclusion: The two-step method produced a catheter which showed higher activity against all the organisms tested.

Bacterial adherence to the three catheters tested above was also determined, using methods described in Example 2. The results are shown in Table 6.

TABLE 6

| Group | P. aeruginosa adherence (cfu/cm) |
|---|---|
| 1 (control) | $6.4 \times 10^3$ |
| 2 (2-step) | $1.7 \times 10^2$ |
| 3 (1 step) | $1.0 \times 10^3$ |

Conclusion Catheters prepared by the two-step method showed lower adherence of P. aeruginosa.

8. EXAMPLE 4: FURTHER BACTERIAL ADHERENCE STUDIES

Further studies evaluated bacterial adherence on polyurethane (PU) 4 Fr. peripherally inserted central venous catheters treated with O+L+C and other antiseptics using an in vitro agar tract model. Preparation of catheters, and the agar tract model, were as described in Examples 1 and 2 above, respectively. The results are shown in Table 7.

TABLE 7

P. aeruginosa adherence (infected 30 minutes after implantation)

| Group | Adherence of P. aeruginosa (cfu/cm) |
|---|---|
| Control(uncoated catheters) | $1 \times 10^3$ |
| 2.5% CHX + 1% TC | 96 |
| 2.5% CHX + 1% TC + 2% L | 92 |
| 2.5% CHX + 1% TC + 3% O | 23 |
| 2.5% CHX + 1% TC + 2% O + 1% L | 0 |

Conclusion: Catheters treated with C+O and C+O+L showed significantly lower adherence.

9. EXAMPLE 5: CATHETERS TREATED WITH TWO FORMS OF CHLORHEXIDINE

Studies were performed to evaluate adherence of P. aeruginosa on catheters treated with solutions containing chlorhexidine acetate (CHA)+chlorhexidine free base (CHX)

The method of coating and testing of adherence were the same as described in Examples 1 and 2 above, respectively. The results are shown in Table 8.

TABLE 8

P. aeruginosa adherence (infected 30 minutes after implantation)

| Group | Adherence of P. aeruginosa (cfu/cm) |
|---|---|
| Control(uncoated catheters) | $3.1 \times 10^3$ |
| 2% CHA + 1.5% CHX | $3.7 \times 10^2$ |
| 2% CHA + 1.5% CHX + 3% O | 58 |
| 2% CHA + 1.5% CHX + 0.5% TC | $1 \times 10^2$ |
| 2% CHA + 1.5% CHX + 0.5% TC + 3% O | 23 |

Conclusion: Catheters Coated with solutions containing CHA+CHX+O or with CHA+CHX+T C+O showed significantly lower adherence.

10. EXAMPLE 6: COMPARISON OF OCTOXYGLYCERINE AND OCTANEDIOL

Studies were performed to evaluate adherence of P aeruginosa on central venous catheters (CVC) impregnated with chlorhexidine, with or without either octoxyglycerine ("OCG") or octanediol. The catheters were prepared essentially as described in Example 1 and adherence was measured using the agar tract model as set forth in Example 2. Results, measured 7 days post-infection, are shown in Table 9.

TABLE 9

P. aeruginosa adherence (infected 30 minutes after implantation)

| Group | (cfu/cm) |
|---|---|
| Control(uncoated catheters) | $4.1 \times 10^3$ |
| 3% CHX | $3.8 \times 10^2$ |
| 3% CHX + 3% O | 8 |
| 3% CHX + 3% OCG | $1 \times 10^2$ |

Conclusion The adherence was significantly lower in the Octanediol group 7 days post infection. Without being bound by any particular theory, it is believed these results may be caused by octoxyglycerin, which is viscous fluid, remaining on the surface of the catheter as an oily coating which has diffused into the agar by the 7th day. In contrast, octanediol, which is a waxy powder, remains on the catheter surface and does not diffuse into the agar, so that bacteria which comes in contact with the surface of an octanediol coated catheter gets killed.

11. EXAMPLE 7: EVALUATION OF S. AUREUS ADHERENCE

Studies were performed to evaluate adherence of S. aureus to polyurethane (PU) 4 Fr. central venous catheters (CVC) treated with C+T+O+L (prepared as in Example 1), using an in vitro agar track model (as described below).

Catheter segments, 4 cm long and sealed at both ends, were inserted vertically into the center of medium in each tube with 0.5 cm of the catheter protruding out of the medium (as in Example 2). The caps of each tube were sealed with parafilm to prevent dessication. 5 catheter segments were used for each test. Untreated catheter segments were used as the control.

After 21 days, the catheters were transferred to fresh agar tracts and after 30 minutes each catheter segment was lifted up (approximately 0.5 cm) and 25 ul of the culture ($1-3\times10^8$ cfu/ml of S. aureus) was added on the catheter just near the surface of the medium so that the inoculum was also spread on medium surface. The catheter was then placed back into its original position and incubated at 37° C. for 7 days The catheter segments were removed from the tubes and blotted on tissue. They were rinsed twice in 10 ml saline (6 segments/10 ml saline) and blotted dry. 0.5 cm was then cut off from both the ends of each catheter segment. Each catheter segment was then put in 4 ml LTSB (drug inactivating medium) in a culture tube and sonicated for 20 min. 0.5 ml aliquot from each tube was then plated out on TSA plates and incubated for 24-48 h. The results are shown in Table 10.

TABLE 10

S. aureus adherence (infected 21 day post implantation)

| Group | Adherence of S. aureus (cfu/cm) |
|---|---|
| Control(uncoated catheters) | $1.0 \times 10^4$ |
| 2.5% CHX + 1% TC | $2.8 \times 10^2$ |
| 2.5% CHX + 1% TC + 2% O + 1% L | 0 |

Conclusion: Group containing O+L showed no adherence even after infected 21 days post implantation.

12. EXAMPLE 8: TREATED SILICONE CATHETERS

Studies were performed to evaluate the antimicrobial efficacy of silicone urinary catheters impregnated with chlorhexidine, triclosan, octanediol and lactic acid.

One set of catheter portions was treated by a one-step method, as follows. Catheters were soaked in solutions comprising active agents dissolved in about 60 percent THF (v/v)+about 30 percent methanol (v/v) and the total volume was made up to 100% with THF. The catheters were soaked for 1 hour, dried at room temperature for 1 hour, rinsed in water and then dried for another hour and used for testing.

Another set of catheter portions was treated by a two-step method, as follows. In step 1, portions of silicone urinary catheters were soaked for 1 hour in 0.3% TC (w/v)+1.0% L (v/v) in 30% Methanol (v/v)+67% (v/v) THF. The catheters were removed, dried for 1 hour, rinsed in water and dried for another hour. In step 2, catheters were dipped in 2% CHX (w/v)+2% O (v/v)+10% (w/v) Silastic Medical Adhesive Type A THF (THF used to bring the volume to 100%) and air dried at room temperature for 24 hours and then used for testing.

Bacterial adherence was evaluated using an in vitro urinary tract model, as follows. The model consists of two tubes one of which was an open cylindrical tube with one end capped and the other end sealed with a rubber cork with a hole in the center (Tube 1). The tube was crimped from both the sides at the center. The second tube was open at one end and was used for collection of urine (Tube 2). Both the tubes were sterilized with ethylene dioxide. Catheter segments of 6 cm in length, with both the ends sealed with silicone to prevent intraluminal contamination with bacteria, were sterilized and were inserted from top end of Tube 1 after lifting the cap aseptically and placed in the hole of the rubber cork at the end.

The sterile modified Trypticase Soya Agar was cooled to 40° C. and then poured along the sides of the tube around the catheter leaving the upper 1 cm of the catheter protruding out in the space above the agar tract, which represented the bladder. When the medium solidified in the tube, the cork at the bottom of the tube was removed gently without disturbing the agar column on the top thus exposing the lower end of the catheter. This lower end of the agar column with the catheter protruding represented the meatus and the agar surrounding the catheter simulated the urethra. This tube was then fixed on "Tube 2" to collect small amount of urine that flowed down the agar tract.

The "meatus" was inoculated daily with 20 μl of $10^6$ cfu/ml of C. albicans after dismantling the collection tube (Tube 2). The "bladder" was filled daily with fresh sterile urine. The "bladder" and the "meatus" were cultured daily on TSA to determine the presence of bacterial growth. On the day a positive "bladder" culture was found, the catheter segment was also processed for determination of bacterial colonization on the catheter surface. This was done by removing the catheter segment from the "bladder" end of the model, rinsing with saline and rolling it on a D/E agar plate followed by incubation for 24 hours at 37° C. to semi-quantitatively determine the bacterial growth on the surface of the catheter.

The results are shown in Table 11.

TABLE 11

Duration of activity against C. albicans for

| | 1-step vs 2-step Preparation Method (Days) | |
|---|---|---|
| Active agents | 1-step | 2-step |
| Control | 1 | 1 |
| 2% CHX + 0.3% TC | 3 | 8 |
| 2% CHX + 0.3% TC + 1.% L + 2% O | 10 | 30 |

Conclusion: Silicone urinary catheters treated with C+TC+O+L showed longer activity.

Catheters prepared by the two step method where the CHX was coated on the outer surface along with a silicone matrix showed superior activity. The two-step method was found to be better for releasing CHX from silicone rubber catheters. Incorporation of chlorhexidine on the outer coating of the silicone matrix appears to release an effective amount of chlorhexidine.

13. EXAMPLE 9: TREATMENT OF PTFE PATCHES

Studies were performed to evaluate the antimicrobial effect of surface treatment of polytetrafluoroethylene ("PTFE") soft tissue patches. In particular, such patches were impregnated with CHX+Silver Carbonate (AgC) and CHX+AgC+O+L.

1 cm$^2$ pieces were soaked in solutions comprising about 60 percent THF (v/v), about 20 percent Methanol (v/v) and about 20 percent ammonium hydroxide (v/v) as well as the active agents indicated below, then suctioned using a vacuum pump and left for 5 minutes. The pieces were removed, dried and rinsed in water. After 24 hours the patches were tested.

The following Adherence Testing Method was used. 4 pieces of PTFE tissue patch, each 1 cm$^2$, were soaked in medium containing 50% TSB+50% BAS (v/v) (1 ml per 1 cm$^2$ of each piece) and placed on an orbital shaker at 37° C. for 7 days. The pieces were removed, and transferred to a fresh media containing 10$^5$ cfu of *S. aureus*/ml (1 ml/1 cm$^2$) and incubated for 24 hours at 37° C. The pieces were removed and rinsed twice in (2 ml/1 cm$^2$) saline) by vortexing at low speed, blotted dry and suspended in drug inactivating media (4. ml/1 piece) and sonicated. 0.5 ml. aliqouts were plated. The results are shown in Table 12.

TABLE 12

| Group | Adherence(Cfu/cm$^2$) |
|---|---|
| Control (untreated Patch) | >105 |
| 0.3% CHX + 0.1% AgC | 66 |
| 0.3% CHX + 0.1% AgC + 1% L + 2% + O | 5 |

Conclusion: The Group containing O+L showed lower adherence.

14. EXAMPLE 10: AGENTS AT CATHETER SURFACE

Pre-weighed 7 Fr catheters having an outer diameter measured to be 0.092" or 0.234 cm diameter were dipped in coating solution comprising 1) 4% CHX+2% Octanediol+1% Lactic acid, in about 30% methanol, about 63% THF and 2) 3.5% CHX+0.75% AgSD+2% Octanediol+1% Lactic acid in about 30% methanol, about 62.75% THE The catheters were dipped and immediately wrapped in pre-weighed aluminum foil to prevent any solvent evaporation and the weight of the coating solution on the catheter was determined.

The coating weights were found to be:
1) 0.022 grams total coating per cm$^2$
2) 0.021 grams total coating per cm$^2$ Based on these weights and the percentages of active agents present, the following amounts of active agents were calculated to be present:
(1) LA=1%=>220 micrograms/cm$^2$ Surface
    CHX=4%=>880 micrograms/cm$^2$ Surface
    1,2-Octanediol=2%=>440 micrograms/cm$^2$ Surface
(2) LA=1%=>210 micrograms/cm$^2$ Surface
    CHX=3.5%=>735 micrograms/cm$^2$ Surface
    1,2-Octanediol=2%=>420 micrograms/cm$^2$ Surface
    AgSD=0.75%=>158 micrograms/cm$^2$ Surface

15. EXAMPLE 11: ZONES OF INHIBITION

Zones of inhibition associated with catheters treated with the active agents indicated in Table 13 were measured. The methods of preparing the catheters and for measuring zones of inhibition were essentially as set forth in Example 1 (for the particular combinations of active agents tested).

TABLE 13

| | Zone of Inhibition (mm) | | |
|---|---|---|---|
| Active Agents | P. aeruginosa | S. aureus | C. albicans |
| 3.5% CHX + 2% O + 1% L | 11.0 | 12.5 | 11.5. |
| 3.5% CHX + 2% O + 1% Salicylic acid | 11.0 | 13.0 | 13.5. |
| 3.5% CHX + 2% OCG + 1% L | 11.0 | 12.5 | 11.5 |
| 3.5% CHX + 1% O + 1% OCG + 1% L | 11.5 | 13.0 | 13.0 |

Conclusion: The activity of catheters with O+OCG was slightly higher than that with O or OCG alone against *C. albicans*.

16. EXAMPLE 12: BACTERIAL ADHERENCE TO IMPREGNATED CATHETERS

Polyurethane catheter segments were impregnated with the following solutions.

1) 2% CHX+1.5% CHA+0.75% AgSD+1% Lactic acid+3% 93A PU+1% 60D PU+30% Methanol+60.75% THF (CHX-CHA-AgSD-L)
2) 2% CHX+1.5% CHA+0.75% AgSD+1% 1,2 Decanediol+1% Lactic acid+3% 93A PU+1% 60D PU+30% Methanol+59.75% THF (CHX-CHA-AgSD-L-D)
3) 2% CHX+1.5% CHA+0.75% AgSD+1% 1,12 Dodecanediol+1% Lactic acid+3% 93A PU+1% 60D PU+30% Methanol+59.75% THF (CHX-CHA-AgSD-L-1,2 Dod)
4) 2% CHX+1.5% CHA+0.75% AgSD+1% 1,12 Dodecanediol+1% Lactic acid+3% 93A PU+1% 60D PU+30% Methanol+59.75% THF (CHX-CHA-AgSD-L-1,12 Dod)
5) 2% CHX+1.5% CHA+0.75% AgSD+1% 1,2 Tetradecanediol+1% Lactic acid+3% 93A PU+1% 60D PU+30% Methanol+59.75% THF (CHX-CHA-AgSD-L-1,14 TD)
6) 2% CHX+1.5% CHA+0.75% AgSD+1% 1,2 Octanediol+1% Lactic acid+3% 93A PU+1% 60D PU+30% Methanol+59.75% THF (CHX-CHA-AgSD-L-O)
7) 3.5% CHX+0.75% AgSD+1% 1,2 Octanediol+1% Lactic acid+3% 93A PU+1% 60D PU+30% Methanol+59.75% THF (CHX-AgSD-L-O)
8) 3.5% CHA+0.75% AgSD+1% 1,2 Octanediol+1% Lactic acid+3% 93A PU+1% 60D PU+30% Methanol+59.75% THF (CHA-AgSD-L-O)
9) 3.5% CHA+0.75% AgSD+3% 93A PU+1% 60D PU+30% Methanol+61.75% THF (CHA-AgSD)

To test bacterial adherence, the following experiments were performed.

Preparation of Agar Tract Model:

0.5% agar+20% bovine adult serum (BAS)+0.5% milk+0.03% trypticase soy broth (TSB) in phosphate buffered saline (PBS). The necessary amounts of agar and TSB were weighed and suspended in PBS with a magnetic stirring bar in the flask. The medium was sterilized by autoclaving at 121° C. for 20 min. After autoclaving, the medium was allowed to cool down to 45-48° C. in a water bath put on a magnetic stirrer. BAS and milk were warmed to room temperature. 5 ml of milk was mixed with 5 ml BAS in a sterile culture tube and added to the flask with gentle stirring. The remaining amount of BAS was added to the flask. The medium was maintained at 45-48° C. 2.5 ml aliquots of medium were dispensed in different culture tubes and allowed to solidify at room temperature.

Evaluation of Bacterial Adherence

Catheter segments, 4 cm long and sealed at both ends, were inserted vertically into the center of the medium in each tube with 0.5 cm of the catheter protruding out of the medium. The caps of each tube were sealed with Parafilm to prevent dessication. 5 catheter segments were used for each test. Untreated catheter segments were used as the control. After 30 minutes, each catheter segment was lifted up (approximately 0.5 cm) and 25 ul of the bacterial culture ($1-3 \times 10^8$ cfu/ml) was added on the catheter just near the surface of the medium so that the inoculum was also spread on medium surface. The catheter was then placed back to its original position and incubated at 37° C. for 7 days. The catheter segments were removed from the tubes and blotted on tissue. They were rinsed twice in 10 ml saline (6 segments/10 ml saline) and blotted dry. 0.5 cm was then cut off from both the ends of each catheter segment. Each catheter segment was then put in 4 nil LTSB (drug inactivating medium) in a culture tube and sonicated for 20 min. 0.5 ml aliquot from each tube was then plated out on TSA plates and incubated for 24-48 hours.

MRSA adherence On central venous catheter coated with various salts of Chlorhexidine along with silver salt and Octanediol was tested, using materials prepared as set forth above. To determine which Chlorhexidine salt would show better efficacy, catheters were coated with CHA, CHX, and a combination of CHA+CHX along with a silver salt and Octanediol and lactic acid was evaluated. Using MRSA as the test organism and adherence was evaluated 21 days post infection. The results are shown in TABLE 14.

TABLE 14

MRSA adherence (21 days after implantation and infection)

| Group | Adherence (Cfu/cm) | $Log_{10}$ Reduction from Control Counts |
|---|---|---|
| Control (uncoated catheters) | $3.8 \times 10^4$ | — |
| CHX- AgSD-L-O | 77 | 2.7 |
| CHX-CHA- AgSD-L-O | 38 | 3.0 |
| CHA-AgSD-L-O | $3.9 \times 10^2$ | 2.0 |
| CHA-AgSD-L | $6.1 \times 102$ | 1.8 |

These data indicate that the groups containing CHX or CHX+CHA showed higher activity than the groups with CHA alone.

To evaluate bacterial adherence to central venous catheter (CVC) segments coated with various alkanediols along with CHX-CHA-AgSD-L, experiments were performed using the impregnation solutions set forth in TABLE 15, below, which also shows the results of these experiments.

TABLE 15

P. aeruginosa adherence (10 days after implantation and infection)

| Group | Cfu/cm | $Log_{10}$ Reduction from Control Counts |
|---|---|---|
| Control (uncoated catheters) | $1.0 \times 10^4$ | — |
| CHA-AgSD | $3.4 \times 10^3$ | 0.52 |
| CHX-CHA-AgSD-L-O | $1.5 \times 10^2$ | 1.80 |
| CHX-CHA-AgSD-L-D | 20 | 3.20 |
| CHX-CHA-AgSD-L-1,2 Dod | 15 | 2.80 |
| CHX-CHA-AgSD-L-1,12 Dod | 18 | 2.70 |
| CHX-CHA-AgSD-L-TD | 32 | 2.50 |

These data indicate that each of the alkanediols tested enhanced the efficacy when used along with CHX-CHA-AgSD-L.

17. EXAMPLE 13: BACTERIAL ADHERENCE TO IMPREGNATE SOFT TISSUE PTFE PATCHES

The following impregnation solutions were prepared:
0.1% Silver carbonate+0.3% CHA (S-CHA)
0.1% Silver carbonate+0.2% CHX+0.15% CHA (S-CHX-CHA)
0.1% Silver carbonate+0.2% CHX+0.15% CA (S-CHX-CHA)
0.1% Silver carbonate+0.2% CHX+0.15% CA+1% O (S-CHX-CHA-O)
0.1% Silver carbonate+0.2% CHX+0.15% CHA+1% D (S1-CHX-CHA-D)
0.05% Silver carbonate+0.2% CHX+0.15% CHA+1% D (S2-CHX-CHA-D)
(all of them contain 1% Lactic acid)
(S=Silver carbonate, D=1,2 Decanediol, O=1,2 Octanediol)

$1 \text{ cm}^2$ pieces of PTFE soft tissue patches ("STPs") were soaked in solutions comprising about 60 percent THF (v/v), about 20 percent Methanol (v/v) and about 20 percent ammonium hydroxide (v/v) as well as the active agents indicated above, then suctioned using a vacuum pump and left for 5 minutes. The pieces were removed, dried and rinsed in water. After 24 hours the patches were tested.

To evaluate bacterial adherence to the STPs, the following experiments were performed. Several 3 piece sets of PTFE tissue patch from each group and unimpregnated control, each $1 \text{ cm}^2$, were soaked in medium containing 50% TSB+ 50% BAS (1 ml per $1 \text{ cm}^2$ of each piece) and placed on an orbital shaker at 37° C. Adherence was tested after seven days as follows: one set from each group was removed, and transferred to a fresh media containing $10^5$ cfu of organisms (1 ml/1 $\text{cm}^2$) and incubated for 24 hours at 37° C. The pieces were then removed and rinsed twice in saline at the rate of 2 ml/cm² by vortexing at low speed, blotted dry and suspended in drug inactivating media (4. ml/1 piece) and sonicated. 0.5 ml. aliquots were plated. Adherence after 14 days was tested as follows. patches were transferred to fresh media on the 7th day and continued orbital shaking for 14 days and then transferred to fresh media containing bacteria and processed as before. Adherence after 21 days was tested as follows: patches were transferred to fresh media on the 7th and 14th days with continuous shaking. On the 21st day, they were transferred to fresh media containing bacteria and processed as before.

The results obtained using different test organisms and after different periods of time are shown in TABLES 16-18, below.

TABLE 16

P. aeruginosa adherence (cfu/cm²) on STPs 7 days after soaking in S.TSB

| Group | Adherence (cfu/cm²) |
|---|---|
| Control | $2.0 \times 10^5$ |
| S-CHA | $6.0 \times 10^4$ |
| S-CHX-CHA | $5.0 \times 10^4$ |
| S-CHX-CHA-O | 630 |
| S-CHX-CHA-D | 43 |

TABLE 17

S. aureus adherence (cfu/cm²) on STPs various days after soaking in S.TSB

| Group | Chlorhexidine level (ug/cm²) | Bacterial Adherence (cfu/cm²) | | |
|---|---|---|---|---|
| | | 7 day | 14 day | 21 day |
| Control | — | $2.3 \times 10^5$ | $1.9 \times 10^5$ | $3.6 \times 10^5$ |
| S-CHA | 86 | 0 | $1.2 \times 10^5$ | $2.6 \times 10^5$ |
| S-CHX-CHA | 94 | 0 | $1.2 \times 10^5$ | N.D |
| S1-CHX-CHA-D | 96 | 0 | 0 | $6.3 \times 10^1$ |
| S2-CHX-CHA-D | 94 | 0 | 73 | $3.4 \times 10^2$ |

ND = Not Determined

TABLE 18

P. aeruginosa adherence (cfu/cm²) on STPs, various days after soaking in S.TSB

| Group | 7 day | 14 day |
|---|---|---|
| Control | $2.0 \times 10^5$ | $1.5 \times 10^6$ |
| S-CA | $6.0 \times 10^4$ | $3.7 \times 10^5$ |
| S-CX-CA | $5.0 \times 10^4$ | $3.0 \times 105$ |
| S1-CX-CA-D | 43 | $3.0 \times 10^4$ |
| S2-CX-CA-D | 101 | $3.1 \times 10^4$ |

18. EXAMPLE 14: BACTERIAL ADHERENCE TO SILICONE URINARY CATHETER SEGMENTS

Bacterial adherence to silicone urinary catheters impregnated using a two-step method with various alkanediols along with Chlorhexidine, Silver carbonate and Lactic Acid was evaluated.

Catheter segments were impregnated as follows.

Step 1: Catheters were soaked for 1 hour in 0.3% Triclosan (T) (w/v)+1.0% L (Lactic Acid) (v/v) in 30% Methanol (v/v)+68.7% (v/v) THF. The catheters were removed, dried for 1 hour, rinsed in water and dried for another hour.

Step 2: Catheters were dipped in the following solutions and dried for 24 hours and then used for testing.

CHX: 2% (w/v) CHX+15% (w/v) Silastic Medical Adhesive Type A+1% glycerin+82% (v/v) THF CHX-O: 2% (w/v) CHX+1% O+15% (w/v) Silastic Medical Adhesive Type A+1% glycerin+81% (v/v) THF CHX-D: 2% (w/v) CHX+1% D+15% (w/v) Silastic Medical Adhesive Type A+1% glycerin+81% (v/v) THF CHX-1,2Dod: 2% (w/v) CHX+1% 1,2 Dodecandiol+15% (w/v) Silastic Medical Adhesive Type A+1% glycerin+81% (v/v) THF CHX-1,12Dod: 2% (w/v) CHX+1% 1,12 Dodecanediol+15% (w/v) Silastic Medical Adhesive Type A+1% glycerin+81% (v/v) THF CHX-TD: 2% (w/v) CHX+1% TD+15% (w/v) Silastic Medical Adhesive Type A+1% glycerin+81% (v/v) THF Duration of resistance of adherence of bacteria on the catheters was tested in the in vitro urinary tract model described above in Section 12. The results are shown in TABLE 19.

TABLE 19

Duration of activity against S. aureus

| Group * | (Days) |
|---|---|
| Control | 1 |
| T-CHX-L | 8 |
| T-CHX-L-O | 30 |
| T-CHX-L-D | >50 |
| T-CHX-L-1,2 Dod | >50 |
| T-CHX-L-1,12 Dod | >50 |
| T-CHX-L-TD | >50 |

* The letters for each catheter group denote the anti-infectives in the catheter These data indicate that silicone urinary catheters containing alkanediols along with T+CHX+L showed longer activity than T+CHX+L.

19. EXAMPLE 15: BACTERIAL ADHERENCE TO IMPREGNATED WOUND DRESSINGS

Wound dressings were impregnated with the following solutions:

Antimicrobial Composition 1

| Ingredients | (% w/w) |
|---|---|
| CHA | 0.15 |
| CHX | 0.15 |
| AgSD | 0.30 |
| Lactic Acid | 0.50 |
| 1,2 Decanediol | 0.50 |
| Polyurethane 93A | 0.40 |
| Polyurethane 60D | 0.10 |
| Methanol | 30.00 |
| Tetrahydrofuran | 67.90 |

Antimicrobial Composition 2

| Ingredients | (% w/w) |
|---|---|
| CHA | 0.15 |
| CHX | 0.15 |
| AgSD | 0.30 |
| Lactic Acid | 0.50 |
| 1,12 Dodecanediol | 0.50 |
| Polyurethane 93A | 0.40 |
| Polyurethane 60D | 0.10 |
| Methanol | 30.00 |
| Tetrahydrofuran | 67.90 |

Antimicrobial Composition 3

| Ingredients | (% w/w) |
|---|---|
| CHA | 0.15 |
| CHX | 0.15 |
| Silver Carbonate | 0.30 |
| Lactic Acid | 0.50 |
| 1,2 Decanediol | 0.50 |
| Polyurethane 93A | 0.40 |
| Polyurethane 60D | 0.10 |
| Methanol | 30.00 |
| Tetrahydrofuran | 67.90 |

Antimicrobial Composition 4

| Ingredients | (% w/w) |
| --- | --- |
| Polyhexamethylene biguanide | 0.30 |
| Silver Carbonate | 0.30 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 67.90 |

Antimicrobial Composition 5

| Ingredients | (% w/w) |
| --- | --- |
| CHA | 0.15 |
| CHX | 0.15 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 68.20 |

Antimicrobial Composition 6

| Ingredients | (% w/w) |
| --- | --- |
| Polyhexamethylene biguanide | 0.30 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 68.20 |

Wound dressings (Dukal Non-Adherent Pad) were dipped into the antimicrobial impregnation solution and dried for 24 hours. The dressings were cut into 1 cm² pieces and the Zones of Inhibition against various bacteria were determined. For the Zones of Inhibition Test, 1 cm² piece of each dressing was placed on a Trypticase Soy Agar plate seeded on the surface with 0.3 mL of $10^8$ colony forming units (CFU)/mL of the test organism. The plates were incubated at 37° C. for 24 hours. The Zone of Inhibition around the dressing was measured. The results are shown in TABLE 20, below.

TABLE 20

Zone of Inhibition (mm) testing of Dressings treated with Antimicrobial Composition (AC) 1, 2, 5 and 6

| Organism | AC 1 | | AC 2 | | AC 5 | | AC 6 | |
| --- | --- | --- | --- | --- | --- | --- | --- | --- |
| | Day 1 | Day 2 | Day 1 | Day 2 | Day 1 | Day 2 | Day 1 | Day 2 |
| S. aureus | 15.0 | 15.0 | 15.0 | 15.0 | 14.5 | 11.0 | 13.5 | 6.5 |
| MRSA | 15.5 | 14.0 | 15.0 | 12.5 | 14.5 | 10.5 | 13.0 | 6.5 |
| P aeruginosa | 14.0 | 14.0 | 15.0 | 15.0 | 13.0 | 5.5 | 8.5 | 5.5 |
| C. albicans | 16.0 | 13.0 | 16.0 | 13.0 | 15.5 | 9.0 | 12.0 | 7.0 |

These data indicate that dressings impregnated with antibacterial agents and alkanediols exhibit broad spectrum antimicrobial activity.

20. EXAMPLE 16: COATING OF URINARY CATHETER BY A ONE-STEP METHOD

The following formulations were used to coat urinary catheters using a one-step method, wherein catheters were coated by dipping a catheter in a solution comprising one of the formulations listed below, and then allowed to dry.

Formulation-1

| Ingredients | % w/v | Range (% w/v) |
| --- | --- | --- |
| Chlorhexidine base | 2.0 | 0.1-5.0 |
| Decanediol | 2.0 | 0.1-5.0 |
| Mandelic acid | 2.0 | 0.1-5.0 |
| Lactic acid | 0.0 | 0-5.0 |
| Silver sulfadiazine | 0.0 | 0-2.0 |
| Silver carbonate | 0.0 | 0.0-1.0 |
| PU 93A | 2.66 | 0.2-5.0 |
| PU 60D | 0.66 | 0.1-2.0 |
| Silicone medical adhesive A-100 | 3.0 | 0.2-10.0 |
| Tetrahydrofuran (THF) | 72.68 | 50.0-80.0 |
| Methanol | 15.0 | 5.0-50.0 |

(Both latex and silicone catheters can be coated with this solution)

Formulation-2

| Ingredients | % w/v |
| --- | --- |
| Chlorhexidine base | 2.0 |
| Decanediol | 2.0 |
| Mandelic acid | 2.0 |
| Silver sulfadiazine | 0.75 |
| PU 93A | 2.66 |
| PU 60D | 0.66 |
| Silicone medical adhesive A-100 | 3.0 |
| Tetrahydrofuran (THF) | 71.93 |
| Methanol | 15.0 |

Formulation-3

| Ingredients | % w/v |
| --- | --- |
| Chlorhexidine base | 2.0 |
| Decanediol | 2.0 |
| Mandelic acid | 1.0 |
| Lactic acid | 1.0 |
| Silver sulfadiazine | 0.75 |
| PU 93A | 2.66 |
| PU 60D | 0.66 |
| Silicone medical adhesive A-100 | 3.0 |

-continued

| Ingredients | % w/v |
|---|---|
| Tetrahydrofuran (THF) | 71.93 |
| Methanol | 15.0 |

Formulation-4

| Ingredients | % w/v |
|---|---|
| Chlorhexidine base | 2.0 |
| Decanediol | 2.0 |
| Mandelic acid | 2.0 |
| Silver carbonate | 0.3 |
| PU 93A | 2.66 |
| PU 60D | 0.66 |
| Silicone medical adhesive A-100 | 3.0 |
| Tetrahydrofuran (THF) | 72.38 |
| Methanol | 15.0 |

Formulation-5

| Ingredient | % w/v |
|---|---|
| Chlorhexidine base | 2.0 |
| Decanediol | 2.0 |
| Mandelic acid | 1.0 |
| Lactic acid | 1.0 |
| Silver carbonate | 0.3 |
| PU 93A | 2.66 |
| PU 60D | 0.66 |
| Silicone medical adhesive A-100 | 3.0 |
| Tetrahydrofuran (THF) | 72.38 |
| Methanol | 15.0 |

Formulation-6

| Ingredients | % w/v |
|---|---|
| Chlorhexidine base | 2.0 |
| Mandelic acid | 2.0 |
| Silver sulfadiazine | 0.75 |
| PU 93A | 2.66 |
| PU 60D | 0.66 |
| Silicone medical adhesive A-100 | 3.0 |
| Tetrahydrofuran (THF) | 73.93 |
| Methanol | 15.0 |

Test 1:
Zone of Inhibition Test: Evaluation of the efficacy of latex urinary catheters coated by the one step method.
Method:
Three 0.5 cm segments of each group of catheters were embedded vertically in modified trypticase soy agar (TSA) media seeded on the surface with 0.3 ml of $10^8$ colony forming units (CFU) per ml of bacteria and $10^6$ cfu/ml of fungi and the plates were incubated at 37° C. for 24 hours. The diameters of zones of inhibition of bacterial growth around the catheter segments were measured, and are shown in Table 1.

TABLE 1

Latex Urinary Catheter: Testing of Zone of inhibition against
S. aureus, E. coli, P. auregonosa, C. albicans

| | Zone of inhibition (mm) | | | |
|---|---|---|---|---|
| Groups | S. aureus | E. coli | P. auregonosa | C. albicans |
| Chlorhexidine (CHX) + Decanediol (D) [Formulation-1] | 16 | 12 | 16 | 18 |
| CHX + D + AgSD [Formulation-2] | 17 | 14 | 17 | 20 |
| CHX + D + Ag$_2$CO$_3$ [Formulation-4] | 16 | 13 | 18 | 18 |

Test 2:
Evaluation of the efficacy of antimicrobial latex urinary catheter coated by the one step method in preventing bacterial adherence when exposed to contaminated urine (Semi-quantitative method).
Method:
Latex catheter segments (1 cm) sealed at both ends were soaked in a culture tube containing 2 ml of artificial urine contaminated with $10^5$ CFU/mL of E. coli. The culture tube was kept in a shaker at 37° C. for overnight. The catheters were transferred daily to fresh artificial urine contaminated with $10^5$ CFU/mL of E. coli. At different time intervals ($1^{st}$, $3^{rd}$, $6^{th}$ and $10^{th}$ day), the catheters were removed, rinsed with saline and rolled on drug neutralizing media (D/E agar). The plates were incubated at 37° C. for 24 hours to semi-quantitatively determine the bacterial adherence on the surface of catheter. Uncoated catheter segments were used as the control. Results are shown in Table 2.

TABLE 2

Adherence of E. Coli on latex urinary catheter and bacterial growth in urine culture after exposed to contaminated urine in various days

| | CFU/cm catheter* (bacterial growth in urine) | | | |
|---|---|---|---|---|
| Number of days | Control | Chlorhexidine (CHX) + Decanediol (D) [Formulation-1] | CHX + D + AgSD [Formulation-2] | CHX + D + Ag$_2$CO$_3$ [Formulation-4] |
| 1 | >10,000 (Heavy) | 0 (No growth) | 0 (No growth) | 0 (No growth) |
| 3 | >10,000 (Heavy) | 0 (Medium) | 0 (No growth) | 0 (No growth) |
| 6 | >10,000 (Heavy) | 0 (Medium) | 0 (Medium) | 0 (Medium) |
| 10 | >10,000 (Heavy) | 27 (Heavy) | 15 (Heavy) | 16 (Heavy) |

*Mean of three samples

Conclusion:

CHX and silver sulfadiazine released initially to inactivate bacteria in the artificial urine. Subsequently, antimicrobials are not released sufficiently to inactivate bacteria in the urine. As a result, urine culture exhibits bacterial growth. However, the antimicrobial impregnated catheter which is surrounded by heavily contaminated urine showed very negligible count of bacterial adherence on its surface after 10 days soaking in contaminated urine.

Test 3:

Zone of Inhibition Test: Evaluation of the efficacy of latex urinary catheters coated by the one step method.

The method for zone of inhibition test is the same as described in Test 1. Results are shown in Table 3.

TABLE 3

Latex Urinary Catheter: Testing of Zone of inhibition against
S. aureus, E. coli, P. auregonosa, C. albicans

| Groups | Zone of inhibition (mm) | | | |
|---|---|---|---|---|
| | S. aureus | E. coli | P. auregonosa | C. albicans |
| CHX + D + AgSD [Formulation-2] | 17 | 14 | 17 | 20 |
| CHX + AgSD [Formulation-6] | 16 | 14 | 16 | 17 |

Test 4:

Evaluation of the efficacy of an antimicrobial latex urinary catheter coated by the one step method in preventing bacterial adherence when exposed to contaminated urine (Quantitative method)

Method:

Latex urinary catheter segments (1 cm) sealed at both ends, were placed in a sterile culture tube individually and suspended in 2 ml of artificial urine contaminated with E. coli ($10^5$ cfu/ml). The tubes were kept at 37° C. incubator in a shaker at low speed for overnight. Uncoated catheter segments were used as the control. Then the catheters were suspended into fresh artificial urine contaminated with E. coli ($10^5$ cfu/ml) and incubated at 37° C. incubator shaker for overnight. Likewise, catheter segments were kept on transferring into fresh artificial urine contaminated with E. coli ($10^5$ cfu/l) every day. After 10 days, the catheter segments were removed from the tubes and blotted on tissue paper to drain out the residual artificial urine. They were rinsed twice in 10 ml sterile normal saline and blotted dry. Each catheter segment was then put in 4 ml DNF (drug neutralizing fluid) in a culture tube and sonicated for 20 min. 0.5 ml aliquot from each tube was then plated out on TSA plate and incubated for 24h. Results are shown in table 4.

TABLE 4

Bacterial adherence on the surface latex urinary catheter and bacterial growth in urine after 10 days soaking in artificial urine

| Groups | $Log_{10}$ growth/cm catheter* (bacterial growth in urine) |
|---|---|
| Control | 9.88 (Heavy growth) |
| CHX + AgSD [Formulation-6] | 1.6 (Heavy growth) |
| CHX + AgSD + D [Formulation-2] | 0.0 (Heavy growth) |

*Mean of three samples

Conclusion:

Latex urinary catheter coated with CHX+AgSD+D is more effective than CHX+AgSD in preventing E. coli adherence.

21. EXAMPLE 17: COATING OF CENTRAL VENOUS CATHETER: BY A ONE STEP METHOD

The following formulations were used to coat central venous catheters using a one-step method, wherein catheters were coated by dipping a catheter in a solution comprising one of the formulations listed below, and then allowed to dry.

Formulation-5

| Ingredients | % w/v | Range (% w/v) |
|---|---|---|
| Chlorhexidine base | 3.0 | 0.1-5.0 |
| Decanediol | 1.0 | 0.1-5.0 |
| Mandelic acid | 1.0 | 0.1-3.0 |
| Lactic acid | 1.0 | 0.1-3.0 |
| Silver sulfadiazine | 0.0 | 0.0-2.0 |
| PU 93A | 4.33 | 0.2-8.0 |
| PU 60D | 1.09 | 0.1-3.0 |
| Silicone adhesive MDT7- 4502 | 1.0 | 0.2-5.0 |
| Tetrahydrofuran (THF) | 71.33 | 50.0-80.0 |
| Methanol | 16.25 | 5.0-50.0 |

Formulation-6

| Ingredients | % w/v |
|---|---|
| Chlorhexidine base | 3.0 |
| Decanediol | 1.0 |
| Mandelic acid | 1.0 |
| Lactic acid | 1.0 |
| Silver sulfadiazine | 0.75 |
| PU 93A | 4.33 |
| PU 60D | 1.09 |
| Silicone adhesive MDT7- 4502 | 1.0 |
| Tetrahydrofuran (THF) | 70.58 |
| Methanol | 16.25 |

Test 5:

Zone of Inhibition Test: Evaluation of the efficacy of polyurethane central venous catheters coated by one step method The method for zone of inhibition test is the same as described in Example 16, Test 1. Results are shown in Table 5.

TABLE 5

Central venous catheters: Testing of Zone of inhibition against S. aureus, E. coli, P. auregonosa, C. albicans (ONE-STEP METHOD)

| Groups | Zone of inhibition (mm) | | | |
|---|---|---|---|---|
| | S. aureus | E. coli | P. auregonosa | C. albicans |
| Chlorhexidine (CHX) + Decanediol (D) [Formulation-5] | 13 | 8 | 12 | 14 |
| CHX + D + AgSD [Formulation-6] | 14 | 9 | 12 | 14 |

Test 6:

Evaluation of bacterial adherence on antimicrobial impregnated polyurethane (PU) 7 Fr. central venous catheters (CVC) using an in vitro agar track model:

Method:

Agar Tract Model:

The medium used was 1.0% bacto agar (W/V)+20% bovine adult serum (BAS) (V/V)+0.5% Parmalat milk (V/V)+0.03% trypticase soy broth medium powder (TSB) (W/V) in phosphate buffered saline (PBS). First, 10 g bacto agar and 0.3 g TSB was dissolved in 795 ml of PBS, and a magnetic stirring rod was included in the flask. The medium was sterilized by autoclaving at 121° C. for 20 min. After autoclaving, it was allowed to cool down to 45-48° C. in water bath. Then, BAS and milk were warmed to room temperature, and 5 ml of Parmalat milk were mixed with 5 ml BAS in a sterile culture tube and added to the agar/TSB-containing flask with gentle stirring. Then the remaining 195 ml of BAS was added to the flask. The medium was maintained at 45-48° C. Finally, 12.5 ml aliquots of medium was dispensed into different culture tubes and allowed to solidify at room temperature.

Evaluation of Bacterial Adherence:

Catheter segments, 4 cm long and sealed at both ends, were inserted vertically into the center of the medium in each tube with 0.5 cm of the catheter protruding out of the medium. The caps of each tube were sealed with parafilm to prevent desiccation. Three catheter segments were used for each test. Uncoated catheter segments were used as the control. The catheter segments were removed after 4 hrs and transferred to a fresh media. Each catheter segment was lifted up (approximately 0.5 cm) and inoculated with 25 µl of the microbial culture ($10^7$ cfu/ml for *S. aureus, P. aeruginosa* and *C. albicans*). The inoculum was added on the catheter just near the surface of the medium, so that the inoculum was also spread on medium surface. The catheter was then placed back to its original position and incubated at 37° C. for 10 days. Then, the catheter segments were removed from the tubes and blotted on tissue paper. They were rinsed twice in 10 ml saline (3 segments/10 ml saline) and blotted dry. 0.5 cm was then cut off from both the ends of each catheter segment. Each catheter segment was then put in 4 ml of drug inactivating medium in a culture tube and sonicated for 20 min. 0.5 ml aliquot from each tube was then plated out on TSA plates and incubated for 24h. The bacterial adherence to the control and test catheter segments are shown in table 6.

TABLE 6

Reduction in microbial adherence on antimicrobial impregnated central venous catheter surface 10 days post implantation in subcutaneous agar tract model

| | $Log_{10}$ growth/cm catheter* | | |
|---|---|---|---|
| Organisms | Control | Chlorhexidine (CHX) + Decanediol (D) [Formulation-5] | CHX + D + AgSD [Formulation-6] |
| S. aureus | 4.8 | 0 | 0 |
| P. aeruginosa | 4 | 1.4 | 0.17 |
| C. albicans | 4 | 1.5 | 0.4 |

*Mean of three samples

Conclusion:

Central venous catheter coated with CHX+D+AgSD is more effective than CHX+AgSD in preventing microbial adherence.

22. EXAMPLE 18: COATING OF THE INNER SURFACE OF A CENTRAL VENOUS CATHETER BY A ONE-STEP METHOD

The following formulations were used to coat the inner lumen of central venous catheters using a one-step method.

Composition of Coating Solution for Inner Lumen of Central Venous Catheter (CVC):

| Ingredients | Range (% w/v) |
|---|---|
| Chlorhexidine base | 0.1-5.0 |
| Mandelic acid | 0.0-5.0 |
| Lactic acid | 0.1-5.0 |
| Ethanol | 50.0-90.0 |
| Tetrahydrofuran(THF) | 10.0-50.0 |

Formulation 1:

| Ingredients | % w/v |
|---|---|
| Chlorhexidine base | 2.0 |
| Mandelic acid | 1.0 |
| Lactic acid | 1.0 |
| Ethanol | 76.0 |
| Tetrahydrofuran | 20.0 |

Formulation 2:

| Ingredients | % w/v |
|---|---|
| Chlorhexidine base | 2.0 |
| Lactic acid | 2.0 |
| Ethanol | 76.0 |
| Tetrahydrofuran | 20.0 |

Ethanol and THF are % volume by volume

Method of Evaluation:

The antimicrobial coating solution was exposed to the inner lumen of the central venous catheter (CVC) for 100 sec. Then the coating solution was flushed out from the CVC inner lumen and the catheter was dried. 1 cm segments from both ends of the catheter was cut and removed. The coated inner lumen of the CVC was filled with *S. aureus* ($10^7$ cfu/ml) and both of the open ends of the CVC were locked with a clip, so that the bacterial culture remained inside the lumen. The outer surface of the catheter was wiped with 70% ethanol, and kept in a shaker for overnight at 37° C. After 24 hrs, the bacterial culture was collected from inside the lumen through a syringe. CVC's were refilled with fresh bacterial culture. This procedure was repeated daily for 10 days Cultures were collected daily up to 10 days from the lumen and were diluted with drug neutralization fluid and plated on trypticase soy agar. Lumen of a control uncoated catheter was also exposed to bacterial culture and processed similar to the coated catheter lumen. All the plates were kept at 37° C. and the colony counts were enumerated.

Results:

Efficacy of Coated Luminal Surface of CVC on Reducing Bacterial Counts of Culture in the Lumen:

| | $Log_{10}$ growth/5 cm CVC catheter* | | | | | |
|---|---|---|---|---|---|---|
| Groups | $1^{st}$ day | $2^{nd}$ day | $3^{rd}$ Day | 5th Day | $7^{th}$ Day | $10^{th}$ Day |
| Control (uncoated) | 8.45 | 8.62 | 8.98 | 8.43 | 8.75 | 8.31 |
| Formulation-1 | 1.26 | 1.53 | 1.91 | 2.05 | 2.1 | 2.23 |
| Formulation-2 | 0.8 | 1.0 | 1.0 | N.D | N.D | 1.0 |

*Mean of three samples
N.D Not done.

Conclusion. Catheter lumens treated with the formulations 1 and 2 exhibit significant antibacterial activity.

23. EXAMPLE 19: COATING OF SILICONE URINARY CATHETER: TWO STEP METHOD

The following formulations were used to coat silicone urinary catheters using a two-step method.

Formulation-7
First Coating:

| Ingredients | % w/w | Range (% w/w) |
|---|---|---|
| Hysol ® urethane adhesive | 20.0 | 5-30 |
| Silicone medical adhesive | 5.0 | 0.2-10 |
| Decanediol | 1.0 | 0.3-2.0 |
| Tetrahydrofuran | 74.0 | 60-90 |

Dip catheters in the above mentioned first coating solution and leave at room temperature for 3 hours.
Then dip in the following second coating solution and dry for 24-48 hours.
Second Coating:

| Ingredients | % w/v | Range (% w/v) |
|---|---|---|
| Chlorhexidine base | 2.0 | 0.1-5.0 |
| Decanediol | 2.0 | 0.1-5.0 |
| Mandelic acid | 2.0 | 0.1-5.0 |
| Lactic acid | 0.0 | 0-5.0 |
| Silver sulfadiazine | 0.0 | 0-2.0 |
| Silver carbonate | 0.0 | 0.0-2.0 |
| PU 93A | 3.33 | 0.2-5.0 |
| PU 60D | 0.83 | 0.1-2.0 |
| Silicone medical adhesive A-100 | 3.0 | 0.2-10.0 |
| Tetrahydrofuran (THF) | 71.84 | 50.0-80.0 |
| Methanol | 15.0 | 5.0-50.0 |

Formulation-8
First Coating:

| Ingredients | % w/w |
|---|---|
| Hysol ® urethane adhesive | 20.0 |
| Silicone medical adhesive | 5.0 |
| Decanediol | 1.0 |
| Tetrahydrofuran | 74.0 |

Dip catheters and leave at room temperature for 3 hours
Then dip in second coating solution and dry for 24-48 hours
Second Coating:

| Ingredients | % w/v |
|---|---|
| Chlorhexidine base | 2.0 |
| Decanediol | 2.0 |
| Mandelic acid | 2.0 |
| Silver sulfadiazine | 0.75 |
| PU 93A | 3.33 |
| PU 60D | 0.83 |
| Silicone medical adhesive A-100 | 3.0 |
| Tetrahydrofuran (THF) | 71.09 |
| Methanol | 15.0 |

Test 7:
Zone of Inhibition Test: Evaluation of the efficacy of silicone urinary catheters coated by a two-step method The method for zone of inhibition test is the same as described in Example 16, Test 1. Results are shown in table 7.

TABLE 7

Silicone Urinary Catheter: Testing of Zone of inhibition against *S. aureus*, *E. coli*, *P. auregonosa*, *C. albicans* (TWO-STEP METHOD)

| | Zone of inhibition (mm) | | | |
|---|---|---|---|---|
| Groups | *S. aureus* | *E. coli* | *P. auregonosa* | *C. albicans* |
| Chlorhexidine (CHX) + Decanediol (D) [Formulation-7] | 13 | 8 | 12 | 14 |
| CHX + D + AgSD [Formulation-8] | 14 | 9 | 12 | 14 |

Test 8:
Evaluation of the efficacy of antimicrobial silicone urinary catheter prepared using a two-step method in preventing bacterial adherence when exposed to contaminated urine (semi-quantitative method):

Method:
Silicone urinary catheter segments (1 cm) were soaked in 4 ml of artificial urine contaminated with *E. coli* and kept in a rotary shaker at 37° C. For the control, uncoated catheter segments were used. The catheters were transferred daily to fresh artificial urine contaminated with *E. coli*. The urine was also sub-cultured daily to determine the effect of drug diffused out of the catheter into the contaminated urine. At different time intervals ($3^{rd}$, $6^{th}$, $9^{th}$ and $12^{th}$ day) the catheters were removed, rinsed in saline and rolled on drug neutralizing media (D/E agar). The plates were incubated at 37° C. for 24 hours to semi-quantitatively determine the bacterial adherence on the surface of the catheter. Results are shown in tables 8 and 9.

TABLE 8

Bacterial growth (*E. coli*) in artificial urine sub-cultured on TSA plate

| Days | Uncoated | CHX + Decanediol (D) [Formulation-7] | CHX + D + AgSD [Formulation-8] |
|---|---|---|---|
| 1 | +++ | − | − |
| 2 | +++ | − | − |
| 3 | +++ | + | − |
| 4 | +++ | + | + |
| 5 | +++ | ++ | + |
| 6 | +++ | ++ | ++ |
| 7 | +++ | ++ | ++ |
| 8 | +++ | ++ | ++ |
| 9 | +++ | ++ | ++ |
| 10 | +++ | ++ | +++ |
| 11 | +++ | +++ | +++ |
| 12 | +++ | +++ | +++ |

− = No growth
+ = Light growth
++ = Medium growth
+++ = Heavy growth

TABLE 9

Reduction in bacterial adherence on silicone catheter surface at different time intervals of soaking in artificial urine

| Groups | $Log_{10}$ growth/cm catheter* | | | |
|---|---|---|---|---|
| | $3^{rd}$ day | $6^{th}$ day | $9^{th}$ Day | 12th Day |
| Control (uncoated) | 5 | 5 | 5 | 5 |
| Chlorhexidine (CHX) + Decanediol (D) [Formulation-7] | 0 | 0 | 0.9 | 1.54 |
| CHX + D + AgSD [Formulation-8] | 0 | 0 | 0.3 | 1.08 |

*Mean of three samples

Conclusion:

In spite of the medium/heavy bacterial growth in the surrounding urine culture medium of the CHX+D+AgSD catheter on the $9^{th}$ and $12^{th}$ days post soaking, the CHX+D+AgSD catheter is more effective than the CHX+D catheter in preventing the adherence of *E. coli* on the $9^{th}$ and $12^{th}$ days post exposure to contaminated urine. As CHX+D+AgSD catheter showed higher efficacy than CHX+D catheter against *E. coli* adherence on catheter surface, the bacterial adherence on the surface of CHX+D+AgSD catheter was re-evaluated by Urinary tract model (see Test 9, below).

Test 9:

Bacterial adherence on CHX+D+AgSD [Formulation-8] silicone urinary catheter implanted in Urinary tract model Method:

In vitro urinary tract model consisted of two tubes, one of which was an open cylindrical tube with one end capped and the other end sealed with a rubber cork with a hole in the center (Tube 1). The tube was crimped from both the sides at the center. The second tube was open at one end and was used for collection of urine (Tube 2). Both the tubes were sterilized with ethylene dioxide. Catheter segments of 6 cm in length, with both the ends sealed with silicone to prevent intraluminal contamination with bacteria, were sterilized and were inserted from top end of "Tube 1" after lifting the cap aseptically and placed in the hole of the rubber cork at the end.

The sterile modified Trypticase Soy Agar was cooled to 40° C. and then poured along the sides of the tube around the catheter leaving the upper 1 cm of the catheter protruding out in the space above the agar tract, which represented the bladder. When the medium solidified in the tube, the cork at the bottom of the tube was removed gently without disturbing the agar column on the top thus exposing the lower end of the catheter. This lower end of the agar column with the catheter protruding represented the meatus and the agar surrounding the catheter simulated the urethra. This tube was then fixed on "Tube 2" to collect small amount of urine that flowed down the agar tract.

Inoculation of the meatus and determination of bacterial growth in the bladder was performed as follows. The "meatus" was inoculated daily with 20 µl of $10^5$ cfu/ml of *P. aeruginosa* after dismantling the collection tube (Tube 2). The "bladder" was filled daily with fresh sterile urine. The "bladder" and the "meatus" were cultured daily on TSA to determine the presence of bacterial growth.

On the day a positive "bladder" culture was found, the catheter segment was also processed for determination of bacterial colonization on the catheter surface. This was done by removing the catheter segment from the "bladder" end of the model, rinsing with saline and rolling it on a DIE agar plate followed by incubation for 24 hours at 37° C. to semi-quantitatively determine the bacterial growth on the surface of the catheter.

TABLE 10

Duration (Days) of antimicrobial efficacy of urinary catheters in Urinary tract model
Duration of antimicrobial efficacy against various uropathogens (Days bladder culture was sterile and no bacterial adherence on catheter surface)

| Organism | Control 1 (Days) | Control 2 (Days) | CHX + D + AgSD (Days) |
|---|---|---|---|
| S. aureus | 1 | 1 | >20 |
| P. aeruginosa | 0 | 0 | 6 |
| E. coli | 0 | 0 | 25 |
| P. mirabilis | 0 | 0 | >30 |
| E. aerogenes | 0 | 1 | 19 |
| K. pneumoniae | 0 | 0 | >30 |

Control 1: Uncoated catheter
Control 2: Coated only with polymers

24. EXAMPLE 20: METHOD OF RENDERING A URINARY CATHETER SURFACE LUBRICIOUS FOR PATIENT COMFORT DURING INSERTION

A one step method of rendering the surface of a urinary catheter highly lubricious for easier insertion and comfort to the patient by dipping the catheter in a coating solution comprising biomedical polymers. The biomedical polymers comprised a combination of hydrophilic polymers selected from polyurethane polymers, and hydrophobic polymers selected from silicone polymers (0.2-30% w/v) and decanediol (0.01-5.0% w/v) dissolved in tetrahydrofuran (50-98% v/v).

Method for Preparing Lubricious Coating on Medical Devices

One-Step Method:

The medical device is dipped in a lubricious matrix system containing hydrophilic polymers (Tecoflex polyurethane 93A, polyurethane 60D, or a combination thereof) (0.2-10% w/v); decanediol (0.01-5.0% w/v); hydrophobic polymers (silicone medical adhesive selected from silicone medical adhesive Type A and medical adhesive MDT7-4502) (0.2-10% w/v); optionally with or without urethane adhesive; in a solvent system containing tetrahydrofuran (50-98% v/v) and dried at room temperature.

Method 1: Coating of Urinary Catheter: By One-Step Method

| Ingredients | % w/v | Range (% w/v) |
|---|---|---|
| Decanediol | 2.0 | 0.01-5.0 |
| PU 93A | 2.66 | 0.1-7.0 |
| PU 60D | 0.66 | 0.1-3.0 |
| Silicone medical adhesive A-100 | 3.0 | 0.2-10.0 |
| Tetrahydrofuran (THF) | 91.68 | 50.0-98.0 |

(Both latex and silicone catheters can be coated with this solution)

The catheter segment coated with above mentioned lubricious polymeric matrix system was dipped in water. After three days, it was observed that the degree of lubricity on the catheter surface appears to be the same as that of the lubricity obtained immediately after coating.

Balloon inflation test was carried out to evaluate the integrity of the lubricious polymeric coating composition on the urinary catheter surface. The balloon segment of the urinary catheter coated with lubricious coating composition was filled with water. Then the balloon was immersed in water. It was found that the integrity of the coating composition remains intact on the catheter surface even after three days in water.

Various publications are cited herein, the contents of which are incorporated by reference in their entireties.

What is claimed:

1. A composition for preparing a bio-film resistant surface comprising
   (a) one or more antimicrobial agent present at a concentration of between about 0.05 and 5.0% weight/volume (w/v);
   (b) one or more releasing agent present at a concentration of between about 0.05 and 5.0% w/v; and
   (c) a lubricious biomedical polymeric matrix comprising
       (i) one or more biomedical polymer present at a concentration of between about 0.2 and 30% w/v;
       (ii) decanediol present at a concentration of between about 0.01 and 5.0% w/v; and
       (iii) one or more solvent present at a concentration of between about 10 and 70% volume/volume (v/v).

2. The composition of claim 1, wherein the one or more antimicrobial agent is selected from the group consisting of biguanide, chlorinated phenol, silver salt, quaternary ammonium compound, povidone iodine, nitrofurazone, berberine, alkanediol, and combinations thereof.

3. The composition of claim 2, wherein the biguanide is selected from the group consisting of chlorhexidine base, chlorhexidine salt, a combination of chlorhexidine salt and base, polyhexanide, alexidine, and combinations thereof.

4. The composition of claim 2, wherein the chlorinated phenol is selected from the group consisting of triclosan, 4-chloro-3,5-dimethylphenol (PCMX), and combinations thereof.

5. The composition of claim 2, wherein the quaternary ammonium compound is selected from the group consisting of benzalkonium chloride, benzethonium chloride, and combinations thereof.

6. The composition of claim 1, wherein the one or more antimicrobial agent comprises chlorhexidine base, chlorhexidine salt, or a combination of chlorhexidine salt and base; and a silver salt.

7. The composition of claim 1, wherein the one or more releasing agent is selected from the group consisting of citric acid, lactic acid, glycolic acid, mandelic acid, benzoic acid, salicylic acid, acetyl salicylic acid, ascorbic acid, and combinations thereof.

8. The composition of claim 1, wherein the one or more biomedical polymer is selected from the group consisting of polyurethane, aliphatic polyether-based polyurethane, silicone polymer, silicone adhesive, hydrophilic cellulose polymer, hydrophobic cellulose polymer, hydrophilic-hydrophobic polymer, hydroxypropyl methyl-cellulose stearoxy ether, biodegradable polymer, polylactic acid, polyglycolic acid, and combinations thereof.

9. The composition of claim 8, wherein the one or more biomedical polymer comprises polyurethane and silicone adhesive.

10. The composition of claim 1, wherein
    (a) the one or more antimicrobial agent comprises chlorhexidine base and is present at a concentration of between about 0.5 and 5.0% w/v;
    (b) the one or more releasing agent is present at a concentration of between about 0.2 and 5.0% w/v and is selected from the group consisting of lactic acid, mandelic acid, and combinations thereof; and
    (c) the lubricious biomedical polymeric matrix comprises
        (i) polyurethane biomedical polymer present at a concentration of between about 1 and 20% w/v and silicone adhesive biomedical polymer present at a concentration of between about 1 and 10% w/v;
        (ii) decanediol present at a concentration of between about 0.01 and 5.0% w/v; and
        (iii) solvent comprising methanol present at a concentration of between about 10 and 50% v/v and tetrahydrofuran present at a concentration of between about 20 and 70% v/v.

11. A composition for preparing a lubricious surface comprising
    (a) one or more biomedical polymer present at a concentration of between about 0.2 and 30% w/v selected from the group consisting of hydrophilic polyurethane polymer, hydrophobic silicone polymer, and combinations thereof;
    (b) decanediol present at a concentration of between about 0.01 and 5.0% w/v; and
    (c) one or more solvent present at a concentration of between about 10 and 70% volume/volume (v/v).

12. The composition of claim 11, wherein the one or more solvent comprises methanol present at a concentration of between about 10 and 50% v/v and tetrahydrofuran present at a concentration of between about 20 and 70% v/v.

13. The composition of claim 12, wherein the hydrophilic polyurethane polymer is at a concentration of between about 0.5 and 10.0% w/v when present and the hydrophobic silicone polymer is at a concentration of between about 1 and 10% w/v when present.

14. A method of producing a bio-film resistant surface, comprising exposing the surface to a composition for preparing a bio-film resistant surface comprising
    (a) one or more antimicrobial agent present at a concentration of between about 0.05 and 7.0% w/v;
    (b) one or more releasing agent present at a concentration of between about 0.05 and 5.0% w/v; and
    (c) a lubricious biomedical polymeric matrix comprising
        (i) one or more biomedical polymer present at a concentration of between about 0.2 and 30% w/v;
        (ii) decanediol present at a concentration of between about 0.01 and 5.0% w/v; and
        (iii) one or more solvent present at a concentration of between about 10 and 70% volume/volume (v/v).

15. A method of rendering a surface of a medical article resistant to bio-film formation, comprising
    (a) exposing the surface to a first composition comprising
        (i) one or more urethane adhesive present at a concentration of between about 5 and 50% w/v;
        (ii) one or more silicone adhesive present at a concentration of between about 1 and 10% w/v;
        (iii) one or more solvent;
    (b) allowing the first solution to dry; and
    (c) exposing the surface to a second composition comprising
        (i) one or more antimicrobial agent present at a concentration of between about 0.05 and 7.0% w/v;
        (ii) one or more releasing agent present at a concentration of between about 0.05 and 5.0% w/v; and
        (iii) a lubricious biomedical polymeric matrix comprising
            (1) one or more biomedical polymer present at a concentration of between about 0.2 and 30% w/v;

(2) decanediol present at a concentration of between about 0.01 and 5.0% w/v; and
(3) one or more solvent present at a concentration of between about 10 and 70% volume/volume (v/v).

16. The method of claim 15, wherein the first composition further comprises decanediol present at a concentration of between about 0.01 and 5.0% w/v.

17. The method of claim 15, wherein the second composition comprises
(i) chlorhexidine base as the antimicrobial agent;
(ii) lactic acid, mandelic acid, or combinations thereof, as the one or more releasing agent; and
(iii) wherein the lubricious biomedical polymeric matrix comprises
   (1) polyurethane biomedical polymer present at a concentration of between about 1 and 20% w/v and silicone adhesive biomedical polymer present at a concentration of between about 1 and 10% w/v;
   (ii) decanediol present at a concentration of between about 0.01 and 5.0% w/v; and
   (iii) solvent comprising methanol present at a concentration of between about 10 and 50% v/v and tetrahydrofuran present at a concentration of between about 20 and 70% v/v.

18. A method of producing a bio-film resistant inner surface of a device comprising exposing an inner surface to a composition comprising
(a) one or more antimicrobial present at a concentration of between about 0.05 and 7.0% w/v selected from the group consisting of chlorhexidine base, chlorhexidine acetate, and a combination of chlorhexidine base and chlorhexidine acetate; and
(b) one or more solvent present at a concentration of between about 2 and 20% v/v selected from the group consisting of methyl-ethyl-ketone, methanol, ethanol, isopropanol, acetone, tetrahydrofuran, and combinations thereof,
wherein the inner surface is exposed to the composition for a time sufficient to impregnate the inner surface with an antimicrobially effective amount of the composition.

19. The method of claim 18, wherein the antimicrobial comprises chlorhexidine base at a concentration of between about 0.1 and 5.0% w/v, and wherein the composition further comprises a fruit acid present at a concentration between about 0.1 and 5.0% w/v selected from the group consisting of lactic acid, mandelic acid, and combinations thereof.

20. The method of claim 18, further comprising exposing an outer surface of the device to a composition comprising
(a) one or more antimicrobial agent present at a concentration of between about 0.05 and 7.0% weight/volume (w/v);
(b) one or more releasing agent present at a concentration of between about 0.05 and 5.0% w/v; and
(c) a lubricious biomedical polymeric matrix comprising
   (i) one or more biomedical polymer present at a concentration of between about 0.2 and 30% w/v;
   (ii) decanediol present at a concentration of between about 0.01 and 5.0% w/v; and
   (iii) one or more solvent present at a concentration of between about 10 and 70% volume/volume (v/v).

21. A medical device prepared according to the method of any one of claims 14, 15, and 18.

22. The composition of claim 1, wherein the surface is a catheter surface.

23. The composition of claim 11, wherein the surface is a catheter surface.

* * * * *